US012802804B2

(12) United States Patent
Kemler et al.

(10) Patent No.: US 12,802,804 B2
(45) Date of Patent: Nov. 17, 2026

(54) DIALYSIS SCHEDULING SYSTEM WITH INTEGRATED TELEMEDICINE AND MACHINE LEARNING OPTIMIZATION

(71) Applicant: Centient Software LLC, Traverse City, MI (US)

(72) Inventors: James E. Kemler, Glen Arbor, MI (US); John William Stanifer, Traverse City, MI (US); Jesse J. Raleigh, Petoskey, MI (US)

(73) Assignee: Centient Software LLC, Traverse City, MI (US)

( * ) Notice: Subject to any disclaimer, the term of this patent is extended or adjusted under 35 U.S.C. 154(b) by 0 days.

(21) Appl. No.: 19/414,264

(22) Filed: Dec. 9, 2025

(65) Prior Publication Data

US 2026/0094702 A1 Apr. 2, 2026

Related U.S. Application Data

(63) Continuation-in-part of application No. PCT/US2024/060339, filed on Dec. 16, 2024.

(Continued)

(51) Int. Cl.

*G16H 40/20* (2018.01)
*A61M 1/36* (2006.01)

(Continued)

(52) U.S. Cl.

CPC .......... *G16H 40/20* (2018.01); *A61M 1/3653* (2013.01); *G06Q 10/0635* (2013.01);

(Continued)

(58) Field of Classification Search

CPC ..... G16H 40/20; G16H 80/00; A61M 1/3653; A61M 2205/3306; A61M 2205/3334; A61M 2230/04; A61M 2230/207

See application file for complete search history.

(56) References Cited

U.S. PATENT DOCUMENTS

| | | | |
|---|---|---|---|
| 6,389,454 B1 | 5/2002 | Ralston et al. | |
| 10,881,347 B2 * | 1/2021 | Barrett | A61M 1/3609 |

(Continued)

FOREIGN PATENT DOCUMENTS

| | | |
|---|---|---|
| CN | 109411061 A | 3/2019 |
| JP | 6647500 B1 | 2/2020 |

OTHER PUBLICATIONS

"Book your dialysis online," printed Dec. 13, 2024.

(Continued)

*Primary Examiner* — Eyob Hagos

(74) *Attorney, Agent, or Firm* — Aurora Consulting LLC; Madison West; Kristen J. Hansen

(57) ABSTRACT

A dialysis system with integrated concurrent appointment and patient assessment capabilities, comprising: a dialysis machine; at least one camera and a video monitor communicatively coupled to the dialysis machine and configured to enable concurrent telemedicine communication between a patient undergoing a dialysis session and at least one healthcare provider remote from the dialysis machine; a handheld imaging device coupled to the dialysis machine, the handheld imaging device configured to capture high-resolution images of patient-specific conditions during the telemedicine session; a scheduling system communicatively coupled to the dialysis machine and configured to: automatically communicate dialysis machine availability to a healthcare scheduling system associated with the at least one healthcare provider, coordinate concurrent appointment confirmations amongst the patient, the dialysis machine availability, and the at least one healthcare provider, and automatically establish a telemedicine session during a portion of the dialysis session.

20 Claims, 20 Drawing Sheets

Related U.S. Application Data

(60) Provisional application No. 63/609,944, filed on Dec. 14, 2023.

(51) Int. Cl.

| | |
|---|---|
| ***G06Q 10/0635*** | (2023.01) |
| ***G06Q 10/109*** | (2023.01) |
| ***G16H 10/60*** | (2018.01) |
| ***G16H 40/63*** | (2018.01) |
| ***G16H 80/00*** | (2018.01) |

(52) U.S. Cl.

CPC ......... *G06Q 10/1097* (2013.01); *G16H 10/60* (2018.01); *G16H 40/63* (2018.01); *G16H 80/00* (2018.01); *A61M 2205/3306* (2013.01); *A61M 2205/3334* (2013.01); *A61M 2230/04* (2013.01); *A61M 2230/207* (2013.01)

(56) References Cited

U.S. PATENT DOCUMENTS

| | | | | |
|---|---|---|---|---|
| 10,937,004 | B2 | 3/2021 | Comerford et al. | |
| 11,282,153 | B1 | 3/2022 | Albro et al. | |
| 2002/0131572 | A1 | 9/2002 | Paradis | |
| 2004/0039628 | A1 | 2/2004 | Thompson et al. | |
| 2006/0143060 | A1 | 6/2006 | Conry et al. | |
| 2006/0161457 | A1 | 7/2006 | Rapaport et al. | |
| 2007/0226010 | A1 | 9/2007 | Larsen | |
| 2009/0177489 | A1 | 7/2009 | Martinez et al. | |
| 2011/0022441 | A1 | 1/2011 | Robertson et al. | |
| 2011/0071850 | A1 | 3/2011 | Nuthi | |
| 2016/0253462 | A1 | 9/2016 | Zhong et al. | |
| 2017/0032092 | A1* | 2/2017 | Mink ................ | G06Q 30/0241 |
| 2018/0043076 | A1 | 2/2018 | Gerber et al. | |
| 2018/0294056 | A1 | 10/2018 | Rothgang et al. | |
| 2018/0353670 | A1 | 12/2018 | Kommala et al. | |
| 2019/0217002 | A1* | 7/2019 | Urakabe ............. | A61M 1/3639 |
| 2020/0051674 | A1 | 2/2020 | Long et al. | |
| 2020/0090132 | A1 | 3/2020 | Bender et al. | |
| 2020/0411170 | A1 | 12/2020 | Brown et al. | |
| 2021/0077015 | A1* | 3/2021 | Barrett ................. | A61B 5/6866 |
| 2021/0193317 | A1* | 6/2021 | Kotanko ................. | A61M 1/14 |
| 2022/0051787 | A1 | 2/2022 | Sugai et al. | |
| 2022/0079516 | A1* | 3/2022 | Raju .................... | A61B 5/4836 |
| 2022/0080091 | A1* | 3/2022 | Plahey .................. | A61M 1/267 |
| 2022/0130508 | A1 | 4/2022 | Merchant et al. | |
| 2022/0192919 | A1* | 6/2022 | Wilson ............... | A61B 5/02028 |
| 2022/0198402 | A1 | 6/2022 | Sanderford et al. | |
| 2022/0378300 | A1* | 12/2022 | Drori ................... | A61B 5/0077 |
| 2022/0392621 | A1 | 12/2022 | George et al. | |
| 2023/0029639 | A1* | 2/2023 | Ghosh Roy .............. | A61B 5/01 |
| 2023/0065466 | A1 | 3/2023 | Callahan et al. | |
| 2023/0073347 | A1 | 3/2023 | Ginsburg et al. | |
| 2023/0282344 | A1* | 9/2023 | Wang ..................... | G16H 40/60 709/227 |
| 2023/0289886 | A1 | 9/2023 | Rat et al. | |
| 2024/0112790 | A1 | 4/2024 | Boonn et al. | |
| 2024/0120104 | A1 | 4/2024 | Kakkar et al. | |
| 2025/0058033 | A1 | 2/2025 | Kiljanek | |
| 2025/0121213 | A1* | 4/2025 | Yuds ..................... | A61M 1/285 |

OTHER PUBLICATIONS

"Renal Scheduling System," BookWise Renal, printed Dec. 13, 2024.

Gallo et al., "Artificial Intelligence to Solve Production Scheduling Problems in Real Industrial Settings: Systematic Literature Review," Electronics 2023, 12, 4732, 16 pages.

International Search Report and Written Opinion re PCT/US2024/060339 dated Feb. 10, 2025 (22 pages).

Reihaneh, et al., "Patient appointment scheduling at hemodialysis centers: An exact branch and price approach," European Journal of Operational Research 309 (2023), 18 pages.

* cited by examiner

200

202

| Time | Site | Patient | Staff | Physician | Equipment |
| --- | --- | --- | --- | --- | --- |
| **Day 1** | | | | | |
| 9:00 AM | Site 1 | P1 | S1_1 | P1_1 | Eq. A_1 |
| 12:00 PM | Site 1 | P2 | S2_1 | P2_1 | Eq. B_1 |
| 3:00 PM | Site 1 | P3 | S3_1 | P1_1 | Eq. C_1 |
| 6:00 PM | Site 2 | P4 | S4_2 | P2_2 | Eq. A_2 |
| 9:00 AM | Site 2 | P5 | S1_2 | P1_2 | Eq. B_2 |
| 12:00 PM | Site 2 | P6 | S2_2 | P2_2 | Eq. C_2 |
| **Day 2** | | | | | |
| 9:00 AM | Site 3 | P7 | S3_3 | P1_3 | Eq. A_3 |
| 12:00 PM | Site 3 | P8 | S4_3 | P2_3 | Eq. B_3 |
| 3:00 PM | Site 3 | P9 | S1_3 | P1_3 | Eq. C_3 |
| 6:00 PM | Site 4 | P10 | S2_4 | P2_4 | Eq. A_4 |
| 9:00 AM | Site 4 | P11 | S3_4 | P1_4 | Eq. B_4 |
| 12:00 PM | Site 4 | P12 | S4_4 | P2_4 | Eq. C_4 |
| **Day 3** | | | | | |
| 9:00 AM | Site 5 | P13 | S1_5 | P1_5 | Eq. A_5 |
| 12:00 PM | Site 5 | P14 | S2_5 | P2_5 | Eq. B_5 |
| 3:00 PM | Site 5 | P15 | S3_5 | P1_5 | Eq. C_5 |
| 6:00 PM | Site 6 | P16 | S4_6 | P2_6 | Eq. A_6 |
| 9:00 AM | Site 6 | P17 | S1_6 | P1_6 | Eq. B_6 |
| 12:00 PM | Site 6 | P18 | S2_6 | P2_6 | Eq. C_6 |
| **Day 4** | | | | | |
| 9:00 AM | Site 1 | P19 | S3_1 | P1_1 | Eq. A_1 |
| 12:00 PM | Site 2 | P20 | S4_2 | P2_2 | Eq. B_2 |

FIG. 2A

250

| Time | Site | Patient | Staff | Physician | Equipment |
|---|---|---|---|---|---|
| | | **Day 1** | | | |
| 9:00 AM | Site 1 | P1 | S1_1 | P1_1 | Eq. A_1 |
| 12:00 PM | Site 1 | P2 | S2_2 | P2_1 | Eq. B_1 |
| 3:00 PM | Site 1 | Open 252 | Open 254 | Open 256 | Open 258 |
| | | **Day 2** | | | |
| 9:00 AM | Site 2 | P3 | S4_2 | P2_2 | Eq. A_2 |
| 12:00 PM | Site 2 | P4 | S1_2 | P1_2 | Eq. B_2 |
| 3:00 PM | Site 2 | Open 260 | Open 262 | Open 264 | Open 266 |
| | | **Day 3** | | | |
| 9:00 AM | Site 3 | P5 | S3_3 | P1_3 | Eq. A_3 |
| 12:00 PM | Site 3 | P6 | S4_3 | P2_3 | Eq. B_3 |
| 3:00 PM | Site 3 | Open 268 | Open 270 | Open 272 | Open 274 |

⋰ ⋰

FIG. 2B

DIALYSIS SCHEDULING SYSTEM WITH INTEGRATED TELEMEDICINE AND MACHINE LEARNING OPTIMIZATION

CROSS-REFERENCE TO RELATED APPLICATIONS

This application is continuation-in-part of PCT/US2024/060339 filed Dec. 16, 2024, which claims the priority benefit of U.S. Provisional Application No. 63/609,944, filed on Dec. 14, 2023, the disclosures of which are herein incorporated by reference in their entirety.

TECHNICAL FIELD

This disclosure relates generally to the field of scheduling medical care, and more specifically, to assessing schedules for patients, care providers, and dialysis equipment and providing integrated telemedicine capabilities to enable concurrent specialist appointments and patient assessments during dialysis treatment sessions.

BACKGROUND

Conventional dialysis scheduling may include scheduling a user for a number of hours per week over a number of weeks. Such a schedule may be fixed to ensure that the patient receives time regulated treatment. The schedule is largely dictated by the needs of a treatment facility, regardless of the user's work schedule, life events, or personal preferences. As such, patients frequently miss dialysis appointments, leading to increased hospitalization and greater mortality.

SUMMARY

Described herein are systems, devices, and methods for analyzing and generating schedules for medical appointments that may include medical equipment, medical personnel, and patients. In some aspects, the techniques described herein relate to a dialysis system with integrated concurrent appointment and patient assessment capabilities, including: a dialysis machine; at least one camera and a video monitor communicatively coupled to the dialysis machine and configured to enable concurrent telemedicine communication between a patient undergoing a dialysis session and at least one healthcare provider remote from the dialysis machine; a handheld imaging device coupled to the dialysis machine, the handheld imaging device configured to capture high-resolution images of patient-specific conditions during the telemedicine session; a scheduling system communicatively coupled to the dialysis machine and configured to: automatically communicate dialysis machine availability to a healthcare scheduling system associated with the at least one healthcare provider, coordinate concurrent appointment confirmations amongst the patient, the dialysis machine availability, and the at least one healthcare provider, and automatically establish a telemedicine session during a portion of the dialysis session according to a respective confirmed time between the patient and the at least one healthcare provider; and a data transmission system configured to transmit, from the dialysis machine to the at least one healthcare provider and during the concurrent telemedicine session, one or more real time: dialysis parameters and the captured images.

In some aspects, the techniques described herein relate to a dialysis system, further including at least one processor configured to: receive, from a vascular access monitoring system, measurements of real-time blood flow parameters and machine pressures for the patient during the dialysis session; receive, from the vascular access monitoring system and based on the measurements, an assessment of arteriovenous fistula vascular access during the dialysis session; trigger scheduling of a vascular appointment when a predefined vascular access threshold is exceeded.

In some aspects, the techniques described herein relate to a dialysis system, further including at least one processor configured to: trigger an arteriovenous fistula maturation assessment system in communication with the dialysis system to monitor fistula development parameters during the dialysis session; in response to receiving, from the arteriovenous fistula maturation assessment system and based on the monitoring, an indication that the fistula is mature, coordinate with the scheduling system to schedule a vascular appointment with a vascular healthcare provider.

In some aspects, the techniques described herein relate to a dialysis system, further including at least one processor configured to: trigger a hematocrit detection device to monitor fluid levels of the patient in real-time during the dialysis session; analyze fluid removal patterns for at least a portion of the dialysis session; and trigger automatic adjustment of dialysis machine parameters to prevent or reduce cramping or nausea for the patient based on the monitored fluid levels and on patterns associated with the monitored fluid levels.

In some aspects, the techniques described herein relate to a dialysis system, wherein the dialysis machine is communicatively coupled to a spatial frequency domain imaging (SFDI) microvascular assessment system communicatively coupled and configured to: trigger the SFDI microvascular assessment system to perform non-contact, noninvasive microvascular assessment of a foot of the patient during the dialysis session; receive, from the SFDI microvascular assessment system, a plurality of hemoglobin biomarkers and a recommendation; and trigger, based on the recommendation, scheduling of concurrent specialist appointments including podiatry, vascular surgery, or endocrinology consultations when the plurality of hemoglobin biomarkers indicate compromised tissue oxygenation or perfusion.

In some aspects, the techniques described herein relate to a dialysis system, wherein the at least one healthcare provider includes one or more of: a nephrology provider, a cardiology provider, an endocrinology provider, a vascular surgery provider, and a podiatry provider.

In some aspects, the techniques described herein relate to a dialysis system, wherein the patient-specific conditions include at least one of: an arteriovenous fistula and a diabetic foot ulcer.

In some aspects, the techniques described herein relate to a dialysis system, wherein the dialysis parameters include blood pressure, heart rate, and oxygen saturation.

In some aspects, the techniques described herein relate to a dialysis system, further including: a blood sampling interface configured to collect blood samples during the dialysis session.

In some aspects, the techniques described herein relate to a dialysis system, wherein the blood sampling interface is communicatively coupled to a point-of-care diagnostic device configured to: perform real-time analysis of blood samples collected during the dialysis session; generate analyte results related to the concurrent telemedicine session; and transmit diagnostic results to the at least one healthcare provider during the telemedicine session.

In some aspects, the techniques described herein relate to a dialysis system, further including: a ranking engine communicatively coupled to the scheduling system, the ranking engine configured to prioritize concurrent telemedicine sessions based on a comparing of a predefined patient preference, clinician availability, and dialysis machine availability.

In some aspects, the techniques described herein relate to a dialysis system, wherein the handheld imaging device is an ultrasound device communicatively coupled to an interface configured to enable clinicians to annotate captured images with patient-specific observations and transmit the annotated images to the scheduling system for integration into a profile associated with the patient.

In some aspects, the techniques described herein relate to a dialysis system, further including: a message generator communicatively coupled to the scheduling system, the message generator configured to: notify the patient and the at least one healthcare provider of appointment confirmations, reschedule one or more appointments for the patient, and provide updates on dialysis machine availability.

In some aspects, the techniques described herein relate to a dialysis system, further including memory configured to store patient data, including fluid loads, weight, and lifestyle metrics, and to transmit the stored patient data to the scheduling system for analysis by the scheduling system.

In some aspects, the techniques described herein relate to a dialysis system, further including: a tactile feedback system including a smart glove interface configured to: provide tactile feedback to the at least one healthcare provider during remote tissue examination; enable remote manipulation and assessment of patient tissues; and enhance diagnostic capabilities during the concurrent telemedicine session.

In some aspects, the techniques described herein relate to a computer-implemented method for providing concurrent healthcare appointments during dialysis treatment, the method including: detecting a patient assignment to a dialysis machine for a scheduled dialysis session; automatically transmitting dialysis machine scheduling information to one or more healthcare scheduling systems associated with a plurality of healthcare providers remote to a dialysis clinic scheduled to provide the dialysis session; coordinating concurrent appointment scheduling between the scheduled dialysis session and at least one healthcare provider in the plurality of healthcare providers; automatically establishing a telemedicine session between the patient and the at least one healthcare provider according to the coordinated appointment scheduling at a time window within the dialysis session; controlling at least one imaging device coupled to the dialysis machine to enable concurrent telemedicine communication between the patient and the at least one healthcare provider during the dialysis session, the controlling including: causing capture of high resolution images from the at least one imaging device, the high resolution images captured during the telemedicine session and being associated with one or more patient-specific condition; causing transmission of the high resolution images to the at least one healthcare provider during the telemedicine session; and receiving, based on the high resolution images, one or more of: a fistula maturation assessment, a vascular access diagnosis, and a patient dialysis profile recommendation.

In some aspects, the techniques described herein relate to a computer-implemented method, wherein the received one or more of: a fistula maturation assessment, a vascular access diagnosis, and a patient dialysis profile recommendation are generated by a machine learning model and an input provided by the at least one healthcare provider, the machine learning model being configured to: analyze a plurality of dialysis parameters associated with the patient; predict, based on the plurality of dialysis parameters, patient complications; automatically generating a recommendation for adjusting dialysis machine parameters including ultrafiltration profiles to preemptively prevent the predicted complications; generating a customized treatment profile according to the adjusted dialysis machine parameters; and storing the customized treatment profile in a patient record.

In some aspects, the techniques described herein relate to a computer-implemented method, further including: transmitting a summary report of the telemedicine session, including the high resolution images and the plurality of dialysis parameters, to a secondary healthcare provider associated with the patient.

In some aspects, the techniques described herein relate to a computer-implemented method, wherein the patient complications include one or more of: muscle cramps, low blood pressure, and fluid overload.

In some aspects, the techniques described herein relate to a method of treatment including: scheduling a patient for a session of a dialysis treatment on a dialysis machine equipped with integrated telemedicine capabilities; coordinating concurrent therapeutic consultations between the session and a healthcare provider remote to a dialysis clinic housing the dialysis machine, the coordinating including automatically transmitting dialysis machine scheduling information to healthcare scheduling systems associated with the healthcare provider; providing concurrent telemedicine care by the healthcare provider during the dialysis session by: automatically establishing a telemedicine session between the patient and the healthcare provider at a predetermined time window within the dialysis session, enabling real-time clinical assessment through controlling at least one imaging device coupled to the dialysis machine to capture high resolution images of patient-specific conditions during the telemedicine session, transmitting the high resolution images to the healthcare provider for immediate clinical evaluation; receiving therapeutic assessments from the healthcare provider based on the high resolution images, the assessments including one or more of: a vascular access diagnosis with treatment recommendations, a fistula maturation assessment with management guidance, and a personalized dialysis profile recommendation; implementing therapeutic interventions based on the received therapeutic assessments to treat the patient.

In some aspects, the techniques described herein relate to a method 20, wherein implementing the therapeutic interventions includes: automatically adjusting dialysis machine parameters to optimize treatment delivery according to the received therapeutic assessments; generating a customized treatment profile according to the adjusted dialysis machine parameters; and storing the customized treatment profile in a patient record.

BRIEF DESCRIPTION OF THE DRAWINGS

The foregoing is a summary, and thus, necessarily limited in detail. The above-mentioned aspects, as well as other aspects, features, and advantages of the present technology are described below in connection with various implementations, with reference made to the accompanying drawings.

FIG. 2A is an example schedule generated by the system of FIGS. 1A-1B.

FIG. 2B is another example schedule generated by the system of FIGS. 1A-1B.

Figure 1A:
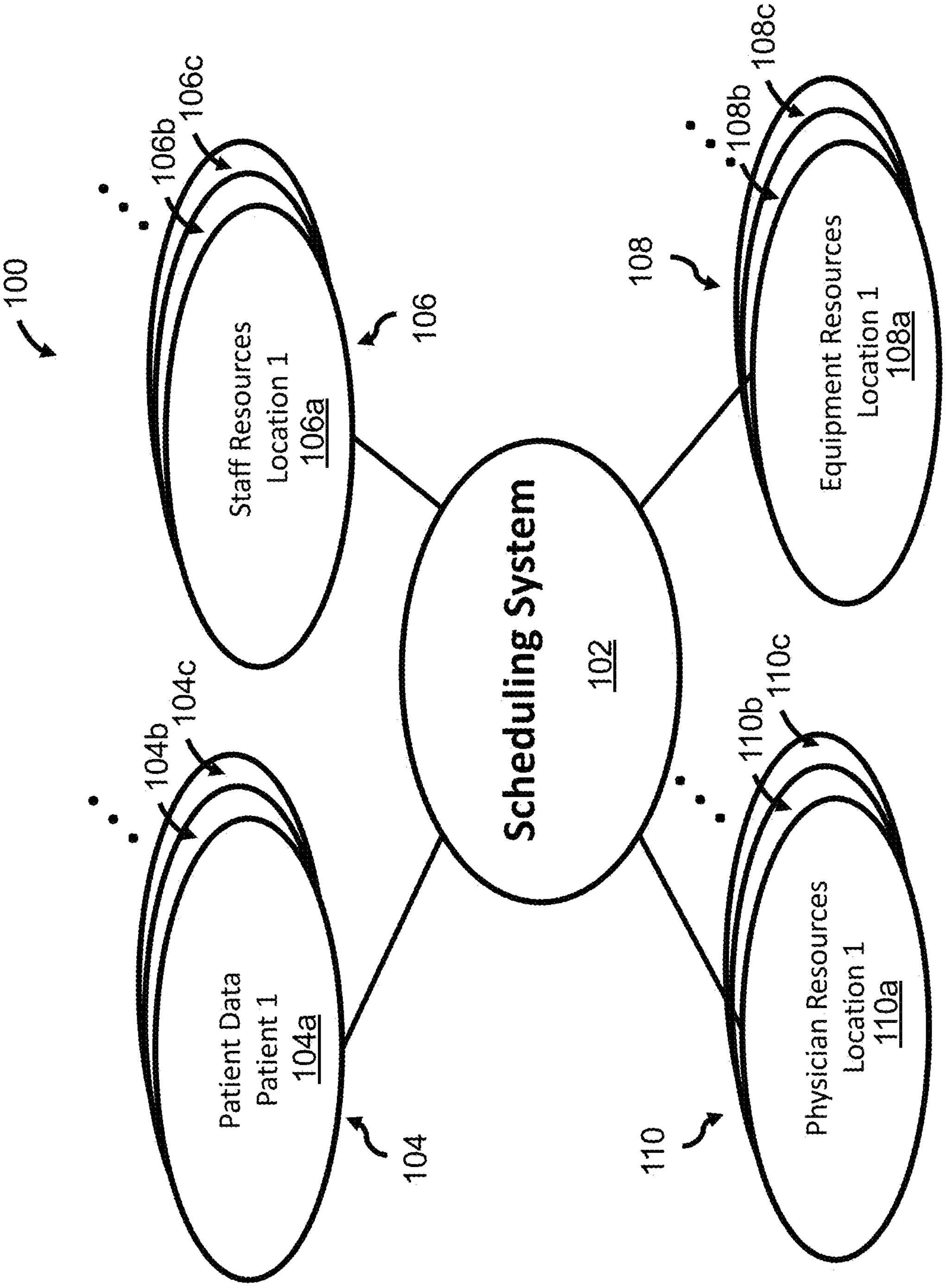
FIG. 1A illustrates an example high level system diagram for generating dynamically optimized schedules for dialysis management.

The illustrated implementations are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the claimed subject matter. Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

The systems described herein may include a scheduling system to provide patient-centric scheduling that may revolutionize medical appointment and resource scheduling. For example, patient-centric scheduling may increase patient satisfaction, patient compliance (e.g., fewer missed appointments and adherence to suggested fluid volume removal in a given week), and potential to avoid unnecessary hospitalizations and improve patient clinical outcomes. The systems and methods described herein may enable patient-centric scheduling for medical appointments and other services including, but not limited to clinical services, surgical services, or other treatment-based service. In addition, the systems and methods described herein may provide an advantage of lessening morbidity and/or mortality risks as compared to conventional scheduling systems and/or conventional scheduling techniques.

In some embodiments, the systems described herein may represent a telemedicine module that connects to existing dialysis machines. For example, the systems described herein may include a telemedicine module for retrofitting existing dialysis machines with advanced telemedicine capabilities. The module may include a self-contained housing unit that detachably couples to a dialysis machine frame without permanent modifications to the dialysis machine core functionality. This modular approach enables dialysis clinics to upgrade existing equipment fleets cost-effectively, avoiding the substantial expense of replacing entire dialysis machines. The housing unit includes integrated cameras, video monitors, and electronics for establishing and managing concurrent healthcare provider consultations during dialysis sessions.

Conventional dialysis machines may lack the integrated capabilities to facilitate concurrent telemedicine appointments during treatment sessions. Furthermore, existing systems may not provide real-time data sharing mechanisms that would enable remote clinicians to access treatment parameters and patient-specific diagnostic information during dialysis sessions. The absence of integrated imaging and diagnostic tools within dialysis machines may prevent specialists from conducting thorough evaluations remotely, thereby contributing to inefficiencies in patient care, increased healthcare costs, and suboptimal clinical outcomes for patients with complex, multisystem medical needs.

In addition, the increase of cardiovascular-kidney-metabolic (CKM) syndrome has highlighted the importance of coordinated care among multiple specialties. Patients with CKM syndrome may benefit from simultaneous consultation with nephrologists, cardiovascular specialists, endocrinologists, podiatrists, etc. to optimize treatment outcomes. However, coordinating such multidisciplinary appointments outside of dialysis sessions may present substantial scheduling and logistical barriers in conventional systems.

In some embodiments, the systems described herein may include a dialysis system that includes integrated concurrent appointment and patient assessment capabilities. The dialysis system may include or be coupled to a dialysis machine equipped with telemedicine infrastructure, including at least one camera and a video monitor communicatively coupled to the dialysis machine. The at least one camera and the video monitor may enable concurrent telemedicine communication between a patient undergoing a dialysis session and at least one healthcare provider who is remote from the dialysis machine. In some embodiments, the at least one healthcare provider may include one or more specialists from various medical disciplines, including but not limited to nephrology, cardiology, endocrinology, vascular surgery, and podiatry. This multidisciplinary approach may be beneficial for patients with CKM syndrome or other complex medical conditions that may benefit from coordinated care across multiple specialties.

The dialysis systems described herein may further include a handheld imaging device detachably coupled (or wirelessly coupled) to the dialysis machine. In some embodiments, the handheld imaging device may capture high-resolution images of patient-specific conditions during a telemedicine session. The patient-specific conditions may include, for example, an arteriovenous fistula or a diabetic foot ulcer. The handheld imaging device may be designed to provide sufficient image quality to enable remote healthcare specialists to conduct meaningful clinical assessments of these conditions without having the patient to travel to a separate appointment. In some embodiments, the handheld imaging device may include an ultrasound device communicatively coupled to an interface to enable clinicians to annotate captured images with patient-specific observations. These annotated images may be transmitted to a scheduling system for integration into a profile associated with the patient, thereby creating a longitudinal record of patient conditions over time.

In some embodiments, the dialysis system may further include a tactile feedback system including a smart glove interface. For example, the tactile feedback system may include a haptic glove worn by the healthcare provider at a remote location. The haptic glove may be communicatively coupled to a robotic palpation device or pressure-sensing interface positioned near the patient at the dialysis machine. In some embodiments, the smart glove interface may include an array of force sensors, actuators, and/or haptic feedback elements distributed across the palm and fingertips of the glove to simulate the sensation of physical touch. The system may further include a complementary patient-side device, such as a mechanized probe or sensor pad, which can be positioned against the skin of a patient at areas of clinical interest, such as an arteriovenous fistula site or a diabetic foot ulcer.

The smart glove interface may provide tactile feedback to the at least one healthcare provider during remote tissue examination. For example, when a vascular surgeon remotely examines an arteriovenous fistula during a concurrent telemedicine appointment, the smart glove may transmit tactile sensations indicating the strength and character of the thrill (e.g., vibration) present in the fistula, which may provide an indicator of adequate blood flow and fistula patency. In some embodiments, when a podiatrist evaluates a diabetic foot ulcer, the smart glove interface may convey information about tissue firmness, temperature variations, and the presence of induration or fluctuance surrounding the wound, enabling the specialist to assess for signs of infection or compromised healing. The tactile feedback may be calibrated to replicate the sensation of pressing on tissue with varying degrees of pressure, such as light touch (about 1-10 grams of force), moderate palpation (about 50-100 grams of force), or deep palpation (about 200-500 grams of force), thereby providing a remote clinician with a comprehensive tactile experience comparable to an in-person physical examination.

The smart glove interface may also enable remote manipulation and assessment of patient tissues. For example, during evaluation of an arteriovenous fistula, the remote vascular surgeon may use the smart glove interface to control a robotic probe that applies graduated pressure along the length of the fistula to detect areas of stenosis, where narrowing of the blood vessel may be indicated by altered flow characteristics or changes in the palpable thrill. In some embodiments, the smart glove may enable a cardiologist to remotely assess for peripheral edema by controlling a pressure-sensing device that compresses the patient's lower extremities and measures the depth and duration of tissue indentation (e.g., pitting), which provides diagnostic information about fluid retention status representing a parameter for dialysis patients with cardiovascular complications. Additionally, when examining a diabetic foot ulcer, the smart glove interface may allow a podiatrist to remotely probe the wound bed to assess tissue viability, detect undermining or tunneling beneath the skin surface, and evaluate for exposed bone or tendon, all of which may be indicated as factors in determining wound severity and treatment planning. The system may further enable the healthcare provider to perform monofilament testing by controlling a calibrated filament that applies a specific force (e.g., about 10 grams) to various locations on the patient's foot to assess protective sensation and identify areas of neuropathy.

The smart glove interface may further enhance diagnostic capabilities during the concurrent telemedicine session. For example, the combination of tactile feedback and high-resolution imaging from the handheld imaging device may enable a vascular surgeon or other practitioner to correlate visual appearance of an arteriovenous fistula with palpation findings to improve the accuracy of diagnosing complications such as aneurysm formation, stenosis, and/or thrombosis that may not be apparent through visual inspection alone. In some embodiments, the tactile feedback system may work in conjunction with a spatial frequency domain imaging (SFDI) microvascular assessment system to provide comprehensive evaluation of diabetic foot ulcers, where tactile assessment of tissue perfusion and turgor may be integrated with objective hemoglobin biomarker measurements to generate a complete picture of wound healing potential and tissue viability.

In some embodiments, the smart glove interface may also include integrated temperature sensors that detect localized areas of warmth that may indicate infection or inflammation, which information may be displayed to the healthcare provider as a color-coded thermal map overlaid on real-time video of the examination area. Furthermore, the tactile feedback system may record and quantify palpation findings, such as measuring the compressibility of edematous tissue in standardized units or documenting the precise location and extent of areas with diminished sensation, thereby creating objective, reproducible data that can be tracked over time and shared with other members of a healthcare team associated with a patient. In some embodiments, the diagnostic capabilities may be further enhanced by machine learning algorithms that analyze patterns in the tactile feedback data to identify changes that may be indicative of developing complications, such as progressive stenosis in an arteriovenous fistula or deteriorating tissue perfusion in a diabetic foot, thereby enabling earlier intervention and improved patient outcomes.

The dialysis system may include a scheduling system communicatively coupled to the dialysis machine. In some embodiments, the scheduling system may automatically communicate dialysis machine availability to a healthcare scheduling system associated with the at least one healthcare provider. The scheduling system may coordinate concurrent appointment confirmations amongst the patient, the dialysis machine availability, and the at least one healthcare provider. Upon confirmation, the scheduling system may automatically establish a telemedicine session during a portion of the dialysis session according to a respective confirmed time between the patient and the at least one healthcare provider.

In some embodiments, when a patient is assigned to a specific dialysis machine for a dialysis session (e.g., which may occur hours or even days in advance), the dialysis machine may communicate its availability to a list of providers who treat the specific dialysis patient. The system may then communicate the available time slot to the other provider for scheduling an appointment with the dialysis patient. The appointment may be confirmed from both the patient side and the provider side. When the dialysis session is initiated on the specific machine, the scheduling system on board the machine may make automatic contact with the various providers to establish the telemedicine session.

In some embodiments, the dialysis system may include a ranking engine communicatively coupled to the scheduling system. The ranking engine may prioritize concurrent telemedicine sessions based on a comparison of predefined patient preferences, clinician availability, and dialysis machine availability. This prioritization may help optimize scheduling efficiency and ensure that urgent consultations are addressed first. In some embodiments, the ranking engine 148 may implement a weighted scoring algorithm where each potential appointment slot receives a composite score calculated as Score=w1(availability score)+w2(patient_preference_score)+w3(clinical_urgency_score)+w4 (resource_optimization_score), where weights w1-w4 are configurable parameters (e.g., w1=0.3, w2=0.25, w3=0.30, w4=0.15) adjusted based on system priorities. Each component score is normalized to zero to one range. Appointments may be rank-ordered by descending score, with ties broken by earliest available time.

The dialysis system may also include a message generator communicatively coupled to the scheduling system. In some embodiments, the message generator may notify the patient and the at least one healthcare provider of appointment confirmations, reschedule one or more appointments for the patient, and provide updates on dialysis machine availability.

In some embodiments, the dialysis system may include a data transmission system that may transmit, from the dialysis machine to the at least one healthcare provider during the concurrent telemedicine session, one or more real-time parameters. In some embodiments, these parameters may include dialysis parameters and captured images from the handheld imaging device. The dialysis parameters may include, in some examples, blood pressure, heart rate, and oxygen saturation measured during the dialysis session.

In some embodiments, the dialysis system may further include memory configured to store patient data, including fluid loads, weight, and lifestyle metrics. The stored patient data may be transmitted to the scheduling system for analysis by the scheduling system, enabling healthcare providers to review historical trends and make informed treatment decisions.

In some embodiments, the dialysis system may include a blood sampling interface for collecting blood samples during the dialysis session. The blood sampling interface may be communicatively coupled to a point-of-care diagnostic device that may perform real-time analysis of blood samples collected during the dialysis session. The point-of-care diagnostic device may generate analyte results related to the concurrent telemedicine session and transmit diagnostic results to the at least one healthcare provider during the telemedicine session.

In some embodiments, the blood sampling interface may include a sterile sampling port integrated into the dialysis blood circuit (e.g., positioned on the arterial line pre-dialyzer) with a septum or valve mechanism allowing needle-free sample extraction. The interface may include a multi-position valve for directing blood flow to either the dialyzer or a sampling chamber, a measured volume chamber for collecting precise sample volumes, automated clamping mechanisms controlled by the dialysis machine processor, and direct fluidic connection to the point-of-care diagnostic device.

In some embodiments, the blood samples may be tested for analytes related to the concurrent appointments, such as calcium and phosphorus levels or other blood chemistry parameters relevant to the patient's condition and/or clinician evaluation. This capability may enable immediate clinical decision-making based on current laboratory values rather than relying on outdated test results.

In some embodiments, the dialysis system may include at least one processor to receive, from a vascular access monitoring system, measurements of real-time blood flow parameters and machine pressures for the patient during the dialysis session. The processor may receive, from the vascular access monitoring system and based on the measurements, an assessment of arteriovenous fistula vascular access during the dialysis session. The processor may trigger scheduling of a vascular appointment when a predefined vascular access threshold is exceeded.

In a non-limiting example, a first patient may be undergoing a dialysis session on a dialysis machine equipped with the integrated vascular access monitoring system. During the first thirty minutes of the dialysis session, the vascular access monitoring system may continuously measure and record blood flow parameters and machine pressures at 30 second intervals. The processor may receive and compare these real-time measurements to baseline values established during the first patient's previous dialysis sessions.

The vascular access monitoring system may analyze the measurements and identify any concerning trends. For example, the monitoring system may determine one or more of: (1) the arterial pressure has become increasingly negative, indicating increased resistance to blood withdrawal from the fistula, (2) the venous pressure has increased by approximately 20%, suggesting possible stenosis in the venous outflow tract, and/or (3) the blood flow rate has decreased by approximately 10% compared to baseline values. Based on these parameters, the vascular access monitoring system calculates a vascular access dysfunction score to determine a level of function or dysfunction to determine whether intervention is indicated. If the monitoring system determines that intervention is indicated, the system may trigger the processor to automatically schedule a vascular appointment.

The scheduling system, upon being triggered by the processor, accesses the dialysis machine's scheduling component and identifies whether the first patient is scheduled for additional upcoming dialysis sessions. The scheduling system then communicates with the healthcare scheduling systems associated with first patient's vascular surgeon, and identifies available appointment slots within the next 7 days. The scheduling system may identify that the surgeon is available at an upcoming appointment of the patient and may schedule the vascular appointment to occur during the scheduled upcoming dialysis session. In some embodiments, if the scheduling system determines that a telemedicine visit is sufficient, the scheduling system may schedule the first patient sooner with the surgeon.

The message generator within the communication engine may generate and transmit a notification message to the first patient's mobile device, indicating, for example, "Important: Your dialysis access monitoring has detected changes that would benefit from evaluation by your vascular surgeon. We have tentatively scheduled a telemedicine consultation with Dr. Smith during your Friday dialysis session at 3:30 PM. Please confirm this appointment or select the alternative Thursday 10:00 AM in-person appointment option." A corresponding notification is sent to the surgeon's office with the vascular access monitoring data, including trend graphs showing the progressive increase in venous pressure and decrease in blood flow rate over the past two weeks, the current dysfunction score, and the proposed appointment times. Upon confirmation of the Friday 3:30 PM appointment, the scheduling system coordinates the concurrent appointment to occur during first patient's dialysis session. When a dialysis session commences before the upcoming scheduled surgeon appointment, the dialysis machine may continue to monitor vascular access parameters and transmit updated measurements to the surgeon's office in preparation for the scheduled telemedicine consultation. At 3:30 PM, the scheduling system may automatically establish the telemedicine connection, and the surgeon may be able to review the real-time dialysis parameters, including the current arterial pressure, venous pressure, and blood flow rate of, confirming a presence or absence of access dysfunction.

In some embodiments during a telemedicine session, a dialysis technician may use a handheld ultrasound imaging device to capture high-resolution images of first patient's arteriovenous fistula, focusing on the anastomosis site and the venous outflow tract. The surgeon or other clinician may use an annotation interface to mark an area about 2.5 centimeters to about 4 centimeters downstream from an anastomosis where the ultrasound images reveal turbulent flow patterns and vessel wall thickening suggestive of stenosis. Based on the combination of the vascular access monitoring data showing elevated venous pressures, reduced blood flow, and the ultrasound findings demonstrating anatomical stenosis, the surgeon or other clinician may provide an assessment recommending fistula angioplasty within a future time period to prevent access failure, for example. The scheduling system may then coordinate an in-person appointment at the vascular surgery center in the future time period for the patient to undergo an angioplasty procedure. This example demonstrates how the integration of real-time vascular access monitoring, automated threshold detection, intelligent scheduling coordination, and concurrent telemedicine capabilities enables early identification of access dysfunction and timely intervention, potentially preventing complete fistula thrombosis that would conventionally involve emergency access procedures and temporary catheter placement, thereby improving patient outcomes and reducing healthcare costs associated with vascular access complications.

In some embodiments, the processor may trigger an arteriovenous fistula maturation assessment system in communication with the dialysis system to monitor fistula development parameters during the dialysis session. In response to receiving (or detecting), from the arteriovenous fistula maturation assessment system and based on the monitoring, an indication that the fistula is mature, the processor may coordinate with the scheduling system to schedule a vascular appointment with a vascular healthcare provider.

In some embodiments, the dialysis system may trigger a hematocrit detection device to monitor fluid levels of the patient in real-time during the dialysis session. The processor may analyze fluid removal patterns for at least a portion of the dialysis session and trigger automatic adjustment of dialysis machine parameters to prevent or reduce cramping or nausea for the patient based on the monitored fluid levels and on patterns associated with the monitored fluid levels. This feature may represent a patient-centric enhancement to the dialysis system that improves patient comfort and safety during treatment. The hematocrit detection device may provide continuous feedback regarding the patient's fluid status, and the processor may use this information to make real-time adjustments to ultrafiltration rates or other dialysis parameters.

In some embodiments, the dialysis machine may be communicatively coupled to a spatial frequency domain imaging (SFDI) microvascular assessment system. The SFDI microvascular assessment system may trigger non-contact, noninvasive microvascular assessment of a foot of the patient during the dialysis session. The dialysis system may receive, from the SFDI microvascular assessment system, a plurality of hemoglobin biomarkers and a recommendation. Based on the recommendation, the processor may trigger scheduling of concurrent specialist appointments including podiatry, vascular surgery, or endocrinology consultations when the plurality of hemoglobin biomarkers indicate compromised tissue oxygenation or perfusion. This capability may be valuable for diabetic patients who are at elevated risk for foot complications and may benefit from early intervention based on objective microvascular assessment data.

In some embodiments, a computer-implemented process for providing concurrent healthcare appointments during dialysis treatment include detecting a patient assignment to a dialysis machine for a scheduled dialysis session and automatically transmitting dialysis machine scheduling information to one or more healthcare scheduling systems associated with a plurality of healthcare providers remote to a dialysis clinic scheduled to provide the dialysis session. The process may further include coordinating concurrent appointment scheduling between the scheduled dialysis session and at least one healthcare provider in the plurality of healthcare providers, and automatically establishing a telemedicine session between the patient and the at least one healthcare provider according to the coordinated appointment scheduling at a time window within the dialysis session. The process may include controlling at least one imaging device coupled to the dialysis machine to enable concurrent telemedicine communication between the patient and the at least one healthcare provider during the dialysis session. The controlling may include causing capture of high resolution images from the at least one imaging device, where the high resolution images are captured during the telemedicine session and are associated with one or more patient-specific conditions. The process may further include causing transmission of the high resolution images to the at least one healthcare provider during the telemedicine session, and receiving, based on the high resolution images, one or more of: a fistula maturation assessment, a vascular access diagnosis, and a patient dialysis profile recommendation.

In general, the systems described herein may include a dialysis system or device integrated with a concurrent appointment and patient assessment system. Such systems may provide advantages over conventional dialysis machines. For example, by enabling telemedicine appointments during dialysis sessions, the systems described herein may transform what is traditionally passive treatment time into productive healthcare opportunities. Patients may benefit from reduced travel burdens, decreased time away from work or family, and more comprehensive, coordinated care. For healthcare providers, the systems described herein may enable more efficient use of time and resources while providing access to real-time patient data and high-resolution imaging during consultations. The integration of multiple specialties during a single dialysis session may be beneficial for patients with CKM Syndrome or other complex conditions utilizing multidisciplinary care.

The automated scheduling and coordination features described herein may reduce administrative burden and scheduling conflicts, while the real-time data transmission capabilities may enhance diagnostic accuracy and enable more informed clinical decision-making. The addition of advanced monitoring features such as hematocrit detection and microvascular assessment may further improve patient outcomes and quality of life during dialysis treatment.

In some embodiments, the systems and methods described herein may be used to schedule people, equipment, and/or other resources for dialysis treatments in an optimized manner for the patient. For example, patients may use the systems to schedule multiple treatment dates according to a user-preferred schedule that enables schedule autonomy while ensuring equipment, staff, and/or other resources are available.

In some embodiments, the systems and methods described herein may be used to schedule people, equipment, and/or other resources for chemotherapy treatments. For example, patients can use the systems to schedule infusion sessions, infusion pumps, or other equipment or resources in a center that typically treats multiple patients.

In some embodiments, the systems and methods described herein may be used to schedule people, equipment, and/or other resources for radiotherapy sessions. For example, patients can use the systems to schedule radiation therapy on specific machines to deliver a prescribed dosage—such as with different types of external beam radiation and image-guided radiation therapy to ensure a cohesive treatment. Similarly, the patient may use the systems to schedule internal, infusion radiation that involves equipment (e.g., intravenous pump, etc.).

In some embodiments, the systems and methods described herein may be used to schedule people, equipment, and/or other resources for imaging procedures with CT, MR, X-ray, and/or ultrasound technologies. For example, patients may use the systems to schedule imaging procedures to coincide before or after another scheduled treatment or may schedule such imaging procedures according to a location at which the other scheduled treatment is scheduled to occur.

In some embodiments, the systems and methods described herein may be used to schedule people, equipment, and/or other resources for infection treatment infusions with intravenous pumps. In some embodiments, the systems and methods described herein may be used to schedule people, equipment, and/or other resources for hyperbaric oxygen therapy in chambers. In some embodiments, the systems and methods described herein may be used to schedule people, equipment, and/or other resources for physical therapy sessions on specific equipment and/or at specific locations. In some embodiments, the systems and methods described herein may be used to schedule people, equipment, and/or other resources for dental procedures utilizing specific chair capacity, equipment, or facility location. In some embodiments, the systems and methods described herein may be used to schedule people, equipment, and/or other resources for HIV infusions, in-hospital diabetes treatment, and/or other disease treatment.

In some embodiments, the systems and methods described herein may use particular algorithms and/or machine learning (ML) algorithms (e.g., neural networks, ML models, training data, etc.) to optimize dialysis scheduling for each user (e.g., patient) while ensuring safety and regulatory parameters and staffing needs are met. For example, the systems and methods described herein may include the use of algorithms and/or ML models to enable the patient to conveniently schedule and reschedule dialysis appointments in a way that optimizes scheduling according to equipment availability, staff (e.g., technician, physicians, etc.) availability, and/or patient dialysis prescriptions or needs.

In some embodiments, the scheduling system may be operated in a mode to bias the output of scheduled events according to a selected entity. In some embodiments, the selected entity may include the patient and the output may include appointments selected to provide convenience and timing based on health needs of the patient. In some embodiments, the selected entity may include the staff of a facility and the output may include appointments selected to ensure convenience for the staff according to staff schedules, staff profiles, or other staff input available to the scheduling system. In some embodiments, the selected entity may include the equipment of a facility and the output may include appointments selected to ensure equipment availability and/or backup equipment availability as well as any staff based schedule that may be associated with particular equipment. For example, particular staff members may be deemed as experts for particular equipment. The scheduling system may ensure that both specific equipment and specific staff members are available before generating a suggested appointment (and/or appointment schedule) for a patient. In this way, the scheduling system may facilitate requests from multiple parties and use equipment configuration and/or availability data to ensure that both staff and patients are satisfied with the scheduling of each dialysis appointment.

In addition, when patient data is available, the scheduling system can ensure that each patient's health is considered when generating dialysis schedules for many patients across any number of facility locations. In some embodiments, the systems described herein may further optimize scheduling for multiple dialysis centers in a region (including the multiple machines and technicians at each center), drive times for remote patients, weather delay risks, and lifestyle choices in between dialysis sessions, etc.

In some embodiments, the scheduling system may be a two layer system that includes a patient schedule and a staffing schedule. The patient schedule may be matched to particular equipment schedules and then further matched with particular staff based on the staffing schedule. For example, the scheduling system may incorporate, for each patient, a patient profile which would determine specific time requirements for scheduling equipment such as a dialysis machine and/or additional equipment that may include additional set up time. In one non-limiting example, the scheduling system may use a patient profile to determine that a particular patient utilizes a Hoyer lift and accordingly, the system may arrange additional appointment time to account for staff schedules and extended equipment usage time. Similarly, the scheduling system may incorporate a staff employee profile, which may include certain credentials that allow specific patient ratios of care, seniority details, and/or an indication of ability to work alone on a shift.

In some embodiments, the dialysis machine described herein includes a plurality of sensors measuring dialysis parameters in real-time. The processor coupled to the dialysis machine may execute machine learning models to analyze the measured parameters and automatically adjust treatment parameters to maintain parameters within therapeutic ranges while coordinating concurrent telemedicine sessions.

In some embodiments, the scheduling system may implement an Epsilon-Greedy reinforcement learning algorithm that: dynamically adjusts scheduling strategy selection based on patient acceptance rates; integrates real-time vascular access monitoring data into rescheduling decisions; and coordinates multi-modal data streaming including video, ultrasound imaging, dialysis parameters, and tactile feedback with synchronization latency below about 100 milliseconds.

In some embodiments, the scheduling system is a three layer system that includes the patient schedule, the staffing schedule, and a layer that also considers a physician schedule in situations where a physician's appointment and a dialysis appointment are being requested to the scheduling system. This third layer may provide an efficiency for both patients and physicians by providing multiple services in a single appointment.

In some embodiments, the scheduling system described herein provides an advantages of accurate automation of scheduling by eliminating double booking conflicts across calendars, reducing human error from manual data entry, and providing audit trails and version histories for appointment scheduling. In addition, the scheduling system may increase efficiency of scheduling because such systems may reduce times for finding openings across multiple calendars and schedules without the use of administrative staff such that the staff can focus on higher value tasks. The scheduling system may increase efficiency of scheduling because the system allows self-service rescheduling of appointments within defined parameters. In addition, schedules for patients, staff, physicians, and equipment may be optimized and real time messaging can ensure that schedules remain clear and concise.

The systems and methods described herein provide an advantage of increasing attendance rates for booked appointments and reducing late cancellations due to double booking because the scheduling system described herein may share and gather availability and/or preference data within a single system. For example, the systems and methods described herein may ensure that a patient can use an easily accessible app to select a series of available appointments to undergo dialysis sessions according to a physician's orders. For example, the scheduling system described herein may assess a patient schedule, an equipment schedule, a staff schedule, and/or a physician schedule and provide available appointments (or appointment series). The patient may accept such appointments/series and/or further request additional appointments, information, statuses, or other data available to the scheduling system. In some embodiments, a patient may submit particular time slots and the systems described herein may algorithmically determine a location (or multiple locations) in which the dialysis appointment(s) can be performed. In particular, the system may perform a number of comparisons, synchronizations, and/or negotiating steps to determine a schedule of appointments that may be conveniently scheduled according to patient requested blocks of time while still meeting the patient health needs, the staff schedules, the physician schedules, and the equipment availability schedules, as will be described in further detail herein.

The system 102 functions to optimize scheduling for patients, equipment, clinicians, and/or facilities. In some embodiments, the system 102 functions to optimize scheduling for dialysis machine usage. In some embodiments, the system 102 functions to optimize scheduling for multiple pieces of medical equipment. The system 102 is used for medical device scheduling and patient scheduling but can additionally or alternatively be used for any suitable applications, clinical or otherwise. The system 102 can be configured and/or adapted to function for any suitable scheduling purpose.

The systems and methods described herein solve a technical problem of determining suitable scheduling for a patient, equipment, and a clinician based on patient availability and/or preferences, equipment availability, and clinician availability and/or preferences. In particular, the technical problem sought to be solved by the present disclosure is to provide scheduling that optimizes use of equipment and clinician time while considering patient requests and/or preferences.

The system 102 can be used to optimize scheduling based on reward-based algorithms, which provides a technical effect of enabling selection of desired appointment scheduling to maximize convenience for a patient, usage of equipment, and to maximize clinician time.

Conventional systems and/or methods may utilize a clinician schedule when determining patient appointments. A potential drawback with such conventional solutions may not account for patient preferences, machine outages or availability, schedule changes, or the like. Thus, the systems and/or methods described herein may provide an improvement over conventional solutions by using any or all of the primary strategies of existing conventional systems as a reward mechanism that may select from (and/or modify) one or more existing scheduling approaches based on a system determined outcome or may instead select or generate a new scheduling approach based on analysis of prior approaches and scheduling options generated by system 102. The scheduling strategy may be selected on a per-patient basis from a variety of provided approaches, for example, in addition to being able to introduce new approaches into the existing system 102.

In addition to being flexible in the ability to schedule patients for Dialysis or other medical or non-medical appointments, the system 102 may also be extensible and able to support multiple types and strategies of appointments concurrently. If the system 102 is orchestrating appointments for multiple services within the same system, the system 102 may make more competent suggestions as a result of having more overall data available.

In a non-limiting example, the scheduling system 102 described herein may utilize rules, calendars, patient data, and/or ranking engine to determine how to schedule patients, staff, equipment, and/or physicians such that a patient can provide input on (or otherwise influence) the scheduling tasks. For example, the scheduling system 102 may generate appointment suggestions by first obtaining calendar data (or other schedule-based data) for any number of patients, staff, physicians, and/or equipment. The system 102 may then normalize the calendars to a singular format (e.g., convert differences in date/time formats, etc.). The system 102 may assess the normalized data to identify busy (e.g., unavailable) times for each assessed calendar by parsing the calendar data to identify periods of time marked as busy or otherwise blocked. The system 102 may aggregate the busy times for all calendars by combining busy times across the calendars into a master list, for example. The system 102 may identify open (e.g., available) time slots within the aggregated data according to rules, calendars, patient data, ranking data, or the like. The system 102 may then filter the available time slots according to particular constraints (e.g., minimum time available, patient constraint, physician constraint, staff constraint, equipment constraint, etc.). Upon filtering the available time slots, the system 102 may determine (and/or rank) one or more time slots that may be presented to the patient for selection. In response to receiving a patient input selecting one of the one or more time slots, the system 102 may generate appointment(s) according to the patient-selected time slot(s).

In some embodiments, the system 102 may further rank the available time slots according to the constraints and/or another user-based or system-based input. For example, the system 102 may rank available time slots before presenting such time slots. In some embodiments, the ranking may be applied according to a longest duration available to prioritize time slots with the longest continuous availability across all calendars. In some embodiments, the ranking may be applied according to time slots in the middle of the day (e.g. 10 AM-4 PM). In some embodiments, the ranking may be applied according to a surrounding context, for example, to boost slots that are surrounded by longer available blocks of time to allow for logistical changes to equipment and/or buffer time between patients. In some embodiments, the ranking may be applied according to patient preferences, for example, to allow each patient to specify preferred meeting times or windows of time. In some embodiments, the ranking may be applied according to a preferred day of the week to account for typical schedules by staff, physicians, and/or patients when ranking across different days. Monday morning may be preferable to Friday afternoon for example. In some embodiments, the ranking may be applied according to a patient or facility location and/or a patient commute time. For example, if locations are provided in calendars, the system 102 maybe give preference to time slots (and locations) in which patients would have shorter commutes to a particular location. In some embodiments, the calendars and preferences described herein may be received as input to the system 102 before time slots are determined. In some embodiments, the calendars and preferences described herein may be received as input to the system 102 after the time slots are determined and provided to the patient. For example, the patient may choose to upload a calendar or enter data pertaining to preferences after determining the system-provided time slots are not conducive to the schedule of the patient. In response, the system 102 may reperform the task of determining one or more time slots in which to schedule the patient based on the received patient calendar (s) and/or input.

When equipment (e.g., medical equipment, such as a dialysis machine) is to be included in the scheduling, the system 102 may integrate with an equipment reservation system through an API, exported data, web scrape, or other data accessing process. To account for equipment availability and scheduling, the system 102 may utilize a number of additional contextual ranking and/or contextual constraints. For example, the system 102 may assess reserved equipment times, maintenance schedules, and/or setup/takedown time to ensure that the equipment is available for any generated appointment suggestions. In addition, staffing availability for operating such equipment may also be considered when generating appointment suggestions for patients.

The systems and methods described herein may provide patients with an option to self-select time slots (e.g., appointments) for completing a prescribed dialysis regimen. Such a regimen (or prescription) may be prescribed by a physician. The regimen may include dialysis parameters that dictate minimum and maximum weekly dialysis requirements for a particular patient. Accordingly, patient self-selected time slots will be tailored to the parameters set by the prescription. The appointments provided by system 102 may be presented for patient selection on a computing device such as a wearable device, a smartwatch, a mobile device, a tablet device, a laptop device, or the like. In some embodiments, the wearable device may include one or more of a smart watch, a fitness tracker, a heart monitor, a continuous glucose monitor, a bioimpedance sensor patch, smart clothing, and/or a smart glove. Patients can input selections for an upcoming week and beyond—out into the future on a weekly basis for several months. In some embodiments, the patient may select appointments for about 6 weeks to about 8 weeks into the future such that dialysis may be performed regularly over a prescribed amount of time.

The systems and methods described herein provide an advantage of ensuring that clinicians (e.g., staff, physicians, etc.) may prescribe a dialysis regimen that prompts the patient to self-select an appropriate amount of dialysis sessions (e.g., appointments) and timing according to the prescribed regimen. The prescribed regimen may also set boundaries for a frequency of dialysis, a minimum and maximum length of time between sessions, a minimum and maximum length of sessions, and the like. In some embodiments, the staff and/or physicians may generate a patient profile for a patient that describes patient acuity, comorbidities, and/or any special requirements for facilitating treatments, such as the need for a Hoyer lift, isolation, or an increased nursing ratio or staff ratio, etc.

The systems and methods described herein may enable staff (e.g., nurses, technicians, etc.) to provide operating windows of time for the available capacity of the dialysis equipment. This includes indicating a ramp up and ramp down time used to prepare the dialysis machine between patients. The staff may review patient profiles to ensure adequate parameters are in place for dialysis configuration time on a patient-specific basis.

FIG. 1A illustrates an example high level system 100 for generating dynamically optimized schedules for dialysis management. The system 100 may include a dialysis scheduling system 102 with access to a number of data inputs that may take the form of patient data 104, application programming interface (API) input, requested input, schedule and calendar input, equipment planning data and maintenance, staff data 106, equipment data 108, physician data 110, training data 151, and/or system variables. For example, the system 100 may include, request, or receive any number of inputs from patient data 104, staff resources 106, equipment resources 108, and/or physician resources 110. In particular, the scheduling system 102 may obtain or request input from any number of locations that schedule patients, house equipment, and employ staff and/or physicians. Each location may be associated with multiple schedules that may be used to generate a master schedule for the location (or group of locations). For example, the patient data 104 may include a number of patients (e.g., Patient 1 104*a*, Patient 2 104*b*, Patient 3 104*c*, etc.). Similarly, the staff resources 106 may include staff and staff schedules associated with Location 1 (e.g., staff resources 106*a*), staff schedules associated with Location 2 (e.g., staff resources 106*b*), staff schedules associated with Location 3 (e.g., staff resources 106*c*), etc. Equipment resources 108 may include equipment schedules and/or usage data for equipment resources at Location 1 (e.g., equipment resources 108*a*), equipment schedules and/or usage data for equipment resources at Location 2 (e.g., equipment resources 108*b*), equipment schedules and/or usage data for equipment resources at Location 3 (e.g., equipment resources 108*c*), etc. Physician resources 110 may include physician schedules and associated data for physician resources at Location 1 (e.g., physician resources 110*a*), physician schedules and associated data for physician resources at Location 2 (e.g., physician resources 110*b*), physician schedules and associated data for physician resources at Location 3 (e.g., physician resources 110*c*), etc.

In operation, the system 100 may receive inputs such as a dialysis prescription including a frequency and duration of dialysis procedures for one or more patients, availability of dialysis equipment, and availability of one or more staff (e.g., technician, nurse, etc.) to operate the dialysis equipment. With such information, the system 100 may generate possible scheduling suggestions for at least one patient to receive dialysis according to the prescription for the at least one patient. For example, the system 100 may utilize scheduling system 102 to determine one or more dates and time periods within the one or more dates in which the patient could receive dialysis based on the frequency and the duration of dialysis (e.g., the prescription). The determined one or more dates and the time periods are generated considering the inputs such that the generated suggested appointment(s) are aligned with the availability of the one or more dialysis machines and the availability of the one or more staff.

In general, the scheduling system 102 may generate appointment suggestions (e.g., indications, meeting requests, etc.) for transmission to a patient. The appointments may be determined by the system 102 as a way to automatically schedule equipment, patients, staff, and/or physicians, and may do so even when equipment, patients, staff, physicians, and multiple locations exponentially increase in number.

In operation, the system 102 may generate appointment suggestions by first obtaining calendar data (e.g., planning data, profile data, preference data, etc.) for any number of patients, staff, physicians, and/or equipment. The system 102 may also obtain equipment reservation schedules (e.g., from a reservation system or equipment tracking database or the like). The system 102 may then normalize data formats to consistent date and/or time fields to begin comparisons amongst the normalized data to identify busy times for each patient, staff, and equipment reservations. The system 102 may aggregate the busy times into a master schedule and identify openings in the schedule for a number of combinations of patient-staff-equipment combinations according to one or more constraints including, but not limited to profile preferences, time availability, prescription or health needs of each patient, rules for a particular location or equipment, buffer time to setup or take down equipment, etc. Upon finding valid days and times in which a particular patient can be scheduled according to their prescription and with appropriate staff, equipment, and/or physician, the system 102 may rank available schedule openings (e.g., appointment suggestion) according to any number of other constraints or preferences as described in further detail herein. The scheduling system 102 may generate and transmit an indication of the ranked available appointment suggestions to the patient for review and selection. Upon receiving a selection from the patient, the system 102 may schedule the appointment(s) and schedule any staff, physician, or equipment reservation(s).

Figure 1B:
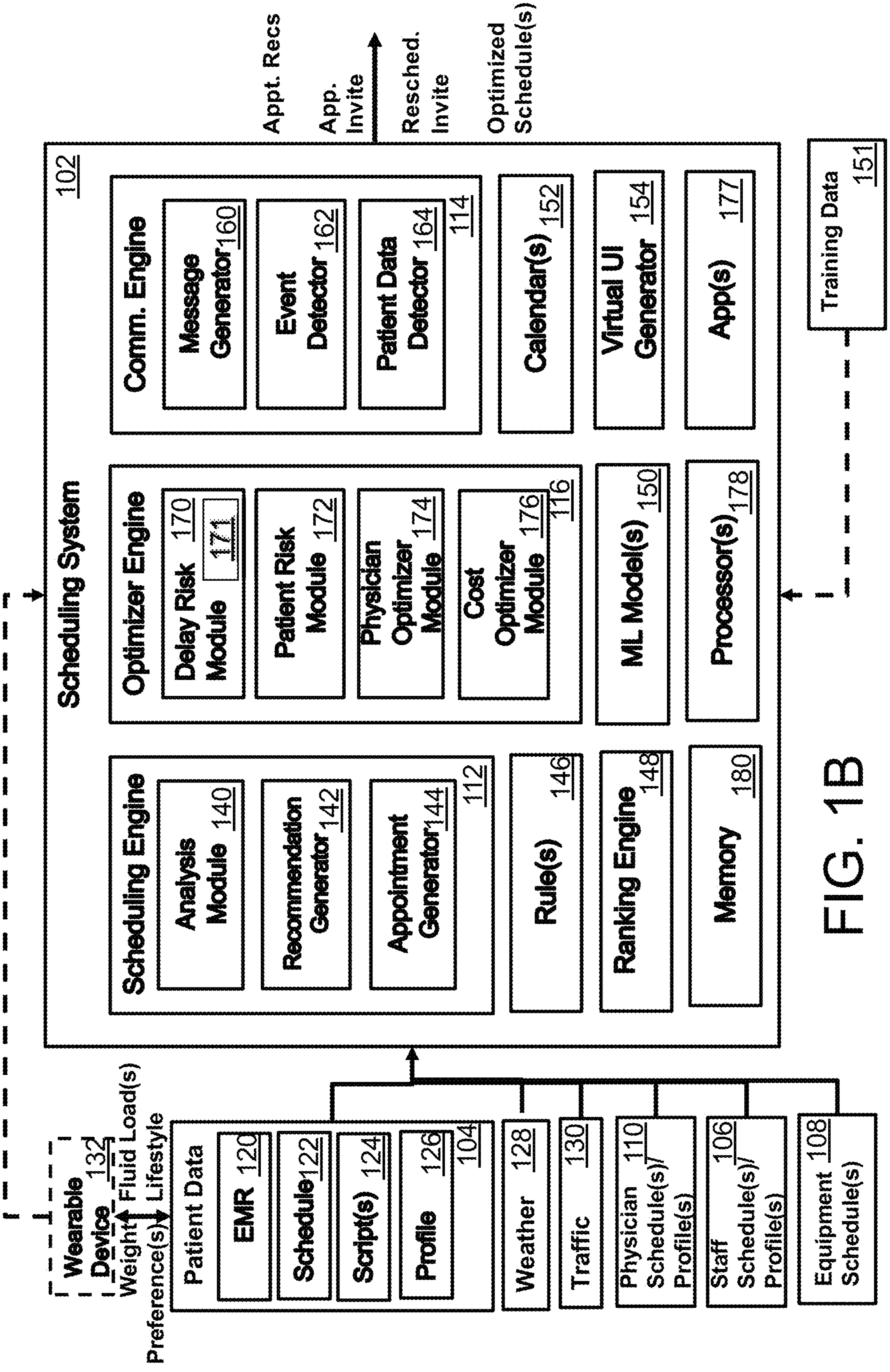
FIG. 1B illustrates an example system diagram for generating dynamically optimized schedules for dialysis management.

FIG. 1B illustrates a detailed view of the example system 100 for generating dynamically optimized schedules for dialysis management. As shown, the scheduling system 102 includes a scheduling engine 112, a communication engine 114, and an optimizer engine 116. The scheduling engine 112 may interface with both the optimizer engine 116 and the communication engine 114 to generate appointment suggestions for patients and to schedule appointments for medical sessions, such as dialysis treatments.

The scheduling system 102 may receive or retrieve (with permission) electronic medical record (EMR) data 120, patient schedule data 122, patient prescription data 124, and/or patient profile data 126 as a basis in which to generate additional suggested appointments and messages pertaining to existing appointments and patient behavior. In addition, the scheduling system 102 may receive or retrieve weather data 128 and traffic data 130 to be used for determining the timing in which to trigger reminder notifications and/or departure notifications for appointments. In some embodiments, the weather data 128 and/or traffic data 130 may further be used to determine a likelihood of patient tardiness or absence. The scheduling system 102 may also receive or retrieve physician schedules and/or profiles 110, staff schedules and/or profiles 106, and equipment schedules 108.

In some embodiments, the scheduling system 102 may further receive or retrieve patient weight changes over time, patient preferences, patient fluid loads, patient lifestyle metrics, or the like, from an optional wearable device 132. In some embodiments, the optional wearable device 132 is a smartwatch. In some embodiments, the optional wearable device 132 is a patch or adhesive-based sensor. In some embodiments, the wearable device 132 is an implanted device. In some embodiments, the optional wearable device 132 is a computing device in which the patient may enter data for system 102 to analyze.

In some embodiments, the wearable device 132 may include a smart glove that provides an interface for assessing patient skin, wounds, or the like. An example smart glove interface may include a wearable glove having a fabric substrate with embedded haptic feedback elements including an array of force sensors (e.g., piezoelectric, capacitive, or strain gauge sensors) positioned at fingertips and palm regions with sensitivity ranging from 1-500 grams of force, for example. The smart glove interface may further include vibrotactile actuators (e.g., linear resonant actuators or eccentric rotating mass motors) providing tactile sensation feedback at frequencies of 50-300 Hz, for example. The smart glove interface may also include temperature sensors and thermoelectric elements for thermal feedback, one or more microcontroller unit (e.g., ARM Cortex processor) for signal processing, and a wireless communication module (e.g., Bluetooth 5.0, Wi-Fi) for low-latency data transmission. The smart glove interface may also include a rechargeable battery and may have access to a networked communication protocol system. In some embodiments, the smart glove interface may communicate bidirectionally with a patient-side robotic palpation device through encrypted wireless protocol, transmitting sensor position and applied force data while receiving haptic feedback commands to replicate tissue characteristics experienced at the patient location.

In some embodiments, the scheduling system 102 may further receive or retrieve patient weight changes over time, patient preferences, patient fluid loads, patient lifestyle metrics, or the like, from a communicatively coupled electronic device (e.g., having received one or more inputs related to the patient). In some embodiments, the electronic device is a mobile phone, laptop, desktop computer, netbook, tablet, or the like.

Referring back to the scheduling engine 112, a number of programmed elements may be used to analyze input and generate appointment suggestions. For example, the scheduling engine 112 includes an analysis module 140, a recommendation generator 142, and an appointment generator 144. The analysis module 140 may utilize two or more of patient data 104, physician schedules/profiles 110, staff schedules/profiles 106, equipment schedules 108, weather data 128, and/or traffic data 130 to determine overlaps in availability of resources available to system 102 and assess when particular messaging is to be transmitted from system 102. For example, the analysis module 140 may access data including reservation data and/or calendar data for each location and within each location may assess equipment schedules 108, staff schedules/profiles 106, and patient data 104, for example. The data may be integrated into a single system or assessed on an ad-hoc basis. The analysis module 140 may assess the data to determine whether particular location logistics should be accounted for when scheduling particular patients based on a distance from the patient location (e.g., tracked location, home address, work address, etc.). The analysis module 140 may assess the data to coordinate overhead scheduling of a particular location by finding openings that work across more calendars and equipment. In some embodiments, the module 140 may determine that a piece of equipment may be used with more patients by relocating or transporting the equipment on a temporary or permanent basis. The analysis module 140 may use rules 146, for example that may include location-specific rules and/or equipment-specific rules, each of which may elucidate administrative rules, operating and permission rules, or the like. In some embodiments, the rules 146 represent a domain specific language used to define and express rules (e.g., similar to LLM prompts).

In some embodiments, the analysis module 140 may also use ranking engine 148 to rank appointments and/or appointment suggestions. The ranking engine 148 may utilize ranking criteria to weight scheduling criteria and/or appointment suggestions. The ranking criteria may be based on one or more inputs (e.g., patient data 104, staff data 106, equipment data 108, physician data 110, training data 151, and/or system variables).

In some embodiments, the analysis module 140 may further use one or more machine learning (ML) models 150 to perform schedule planning tasks and schedule generating tasks. In some embodiments, the ranking engine 148 may directly access the ML models 150 to perform ranking tasks. For example, the analysis module 140 may access one or more ML models 150 to process patient and appointment data from any number of input sources and may provide normalized outputs for future processes of identifying appointments to be scheduled for a user. The recommendation generator 142 may use output from the analysis module 140 and apply the Epsilon-Greedy algorithm described herein and/or the Monte Carlo simulations to identify optimized appointment times for a user.

The ML models 150 (e.g., neural networks, ML models, training data, etc.) may be used to generate and/or optimize dialysis scheduling for each user (e.g., patient) while ensuring safety and regulatory parameters and staffing needs are met. For example, the systems and methods described herein may include the use of algorithms and/or ML models 150 to enable the patient to conveniently schedule and reschedule dialysis appointments in a way that optimizes scheduling according to equipment availability, staff (e.g., technician, physicians, etc.) availability, and/or patient dialysis prescriptions or needs.

In general, the ML models 150 may include neural networks that may be trained to perform constraint optimization modeling, regression modeling, similarity modeling, queue modeling, or other modeling technique to assess patients, staff, and physicians in combination and to further generate possible appointment suggestions that fit the performed modeling. In some embodiments, the ML models 150 may utilize reinforcement learning models to learn scheduling policies over time, for example. In some embodiments, the ML models 150 may utilize graph neural networks to represent physicians, clinic locations, patients, staff, and available equipment. The graph neural network (GNN) may model interactions and connections and optimize assignment of patients to staff and/or physicians. In some embodiments, the ML models 150 may utilize queuing models to predict a number of patients arriving over time and wait times or backlogs occurring at a clinic location, for example. Such models may schedule based on the queue dynamics assessed using the queuing models. In some embodiments, the ML models 150 may utilize regression models to predict appointment durations, no show patients, and to forecast appointment time lengths according to staff or procedure. In some embodiments, the ML models 150 may include or represent large language models (LLMs) that interpret prompts and generate scheduling recommendations, as described elsewhere herein. In some embodiments, the ML models 150 may include or represent a library of ML models, which may be applied to solving various types of scheduling concerns.

In some embodiments, the ML models 150 may be trained using training data 151. The training data 151 may include, but is not limited to logs of historical schedule and/or appointment records, demand for appointment data, historical waitlisted metrics for patients awaiting appointments, historical availability records for staff, physicians, and equipment, historical maintenance records for equipment, etc. In some embodiments, training data 151 may be collected by working with clinic staff at one or more locations to obtain structured data, patient demographics, appointment types, provider calendars/availability, cancellation data, etc. Such data may be anonymized to remove identifiable information before being used as training data. In one non-limiting example, the ML models 150 may be trained on clinic data for any number of locations to predict optimal appointment slots for dialysis. Specialty-specific appointment patterns and/or durations can be incorporated. The performance of the trained ML models 150 may be validated before deployment.

In some embodiments, historical appointment data (e.g., including timeliness of the appointment) may enable the system 102 to provide insightful recommendations upon the first appointment using it for each patient. Each subsequent appointment may inform the system 102 to enable the system 102 to learn about appointment/patient behavior over time. Without such data, the system 102 may use the training data 151 to determine appointment recommendations. Input from one or more wireless devices 132, patient data 104, weather 128, traffic 130, or the like can be used to inform the recommendations generated by system 102. For example, when generating recommendations for dialysis scheduling, the system 102 may consider blood records and treatment data in addition to schedule events for staff/clinicians and patients.

The ML models 150 may generate algorithms that use machine learning techniques to generate smart schedules that account for patient preferences, staff preferences, physician preferences, and equipment efficiencies. The ML models 150 may determine appointment suggestions for a patient based on any number of constraints or inputs, as described in detail herein. The ML models 150 may work with scheduling system 102 to generate UI content for presenting the appointment suggestions to a patient (e.g., user) and to receive input from the user. The ML models 150 may use such input to generate additional appointment suggestions, schedule a selected appointment, trigger messaging, trigger requests, and/or to provide additional information to patients, staff, and/or physicians.

In some embodiments, the system 102 may utilize model free learning (i.e., without ML models 150) and such learning may derive data from real world scheduling over time. Model free learning may be executed by processor 178 and memory 180 in combination with scheduling engine 112, communication engine 114, and/or optimizer engine 116. For example, the system 102 may utilize model a model-free reinforcement learning algorithm such as Q-learning that employs temporal differences where predictions are evaluated after each step in the learning algorithm.

In some embodiments, the system 102 may utilize an Epsilon-Greedy Q-learning algorithm to construct a flexible, model free system for optimizing schedules. Using the Epsilon-Greedy Q-Learning algorithm may ensure that the system 102 balances itself between exploration and exploitation. For example, the Epsilon-Greedy Q-Learning algorithm may select from one of a fixed pool of potential choices and may learn which option produces a highest number of rewards over time. The epsilon value may control the ratio of exploration to exploitation, and it can be dynamically modified each iteration to adjust the behavior of the system 102. The closer a value is to zero, the more the system is set to Exploit versus Explore. By tracking the win rate (e.g., successful scheduling event) versus loss rate (e.g., unsuccessful or erroneous scheduling event) for each of the strategies, the system may adjust the epsilon value to become more or less exploratory as a result of the success or failure of our scheduling strategies.

The scheduling strategies may be represented by software algorithms that conform to the same interface. This allows individual strategies to prioritize different pieces of data in an approach to generating a successful result. An example may include an instance of the strategy for every appointment block throughout the day. Each patient can be treated as a new element in the system 102 and each strategy may include an appointment day and time. Initially, the system 102 may offer the patient all the available time slots, and the time slots that are selected may be considered a win. Until the system 102 executes enough iterations of the algorithm to tip into exploitation mode, the system 102 may continue suggesting available time windows that have a high likelihood of success from past scheduling events.

In this example, patients can be weighted in the algorithm, as well as weighted according to a patient cancellation rate. These weights can be used to estimate cancellation rates on a given day based on the traits of the patients scheduled that day. In some embodiments, the system 102 may optimize the schedule to not schedule multiple patients in a given day that are prone to cancellations. Intentionally scheduling a balanced ratio of patients likely to cancel versus patients that are historically reliable could serve as a means of reducing pressure from staff while making an honest attempt at giving patients appointment opportunities.

In operation, the system 102 may present a patient appointment as a choice to the Epsilon-Greedy algorithm. A variety of weighted factors may be used to produce a reward to the algorithm, such as punctuality, equipment availability, and/or dialysis outcomes, for example. Appointments can be derived as a function of dialysis machines (or other equipment) multiplied by a number of time windows per day in which such machine are usable, as well as staff availability. The system 102 may function to balance staff, equipment, and patients to optimize for an ideal utilization rate of equipment, resources, and the like. For example, a maximum efficiency rate may be defined as an ideal utilization rate. In the example of dialysis equipment, the system 102 may define and 80% maximum efficiency as the ideal utilization rate to allow for emergencies and unforeseen disruptions that may take such equipment out of service.

In some embodiments, the scheduling system 102 may carry out Monte-Carlo simulations on historical appointment data to provide recommended appointment schedules when a patient is initially introduced to the system 102, for example. Monte-Carlo simulations may be used in an ongoing basis to derive next-appointment recommendations and/or to forecast anticipated risk for each choice entered into system 102.

In some embodiments, the system 102 may incorporate an unlimited number of potential scheduling strategies, such as a next day policy, a next available day policy, a shortest queue policy, and any others that may be identified over time. These alternative policy types can be presented as another type of abstract machine for the Epsilon-Greedy algorithm to explore. Additional policy types may be used instead of, or in addition to other types of strategies, among the same or different patients within the system.

In some embodiments, the recommendation generator 142 may obtain data from the analysis module 140, ranking engine 148, ML models 150, and/or calendars 152 to generate one or more recommended appointments for a particular patient. In some embodiments, the ML models 150 may perform patient and schedule analysis with analysis module 140 while utilizing pattern classification to match patient requests to system 102 availabilities. In such an example, the ML models 150 may use output from the analysis module 140 to generate recommendations for appointments in which to suggest to patients. Such recommendations may be generated by recommendation generator 142, which may function with the ML models 150 to generate the recommendations. In some embodiments, the recommendation generator 142 may instead utilize historical records and other input to generate recommendations for a patient without utilizing ML models 150.

In general, a recommendation generated by recommendation generator 142 may be a desired scheduling recommendation or an undesired scheduling recommendation. The system 102 may weight such recommendations according to categories such as user requests, punctuality of users or clinicians, medical outcomes, personality conflicts (e.g., staff vs. patient, patient vs. patient), and/or acceptance ratio, etc. The weighting may be based on any number of categories and such categories can be incorporated into a scheduling strategy for a particular patient, clinician, or location.

In a non-limiting example, a punctuality metric may be defined by the system 102 as being a metric of a patient check in time with respect to a scheduled time of an appointment. If a patient is chronically a number of minutes late for an appointment with a first piece of equipment, the system 102 may use the punctuality metric associated with the patient record, for example, to recommend a later appointment at an updated time slot with a second piece of equipment to ensure that other appointments on the first piece of equipment are not delayed. If the patient is then consistently on time, the updated time slot may increase in weight over time indicating that the later time slot is a preferred or more convenient time slot. Conversely, if the patient continues to be chronically late for the updated time slot, the recommendation indicating the updated time slot may lose weight and other time slots may instead be suggested.

In one non-limiting example, a personality conflict metric may be accounted for in recommendations provided by system 102. The personality conflict metric may represent a patient-indicated or clinician-indicated desire for scheduling appointments with particular patients/clinicians/locations (or lack of desire). In general, personality conflict metrics may be weighted using a zero (e.g., do not suggest appointment with clinician, location, etc.) or a one (feel free to suggest an appointment with clinician, location, etc.). Such metrics and weightings may allow the system 102 to optimize against scheduling two parties with conflict during the same time period, and/or may minimize the overlap to the extent possible.

In one non-limiting example, an acceptance ratio metric may be accounted for in recommendations provided by system 102. The acceptance ratio metric may represent a number of times in which the scheduling staff has accepted or rejected a given time slot. Each acceptance may increase the weight, while each active rejection may decrease the weight.

In one non-limiting example, a medical outcome metric may be accounted for in recommendations provided by system 102. The medical outcome metric may represent previous medical outcomes exhibited by the patient and/or the clinician. Medical outcome metrics are generally dependent upon the type of scheduling being conducted. When using medical outcome metrics as a basis for recommending appointment times/days, scheduling data as well as EMR data 120 may be utilized by the algorithm in determining an ideal next appointment for dialysis patients, for example.

Other metrics are of course possible, as one skilled in the art will appreciate. In addition, any combination of the metrics may be used to generate a recommendation for an appointment.

In some embodiments, references to the system 102 may refer to components of FIG. 1B functioning to optimize scheduling, equipment usage, clinician time, or the like. In some embodiments, the EMR data 120 may be used to generate various weighted parameters on a patient record within the system 102. Similarly, schedule data 122 may represent historic schedule data used to establish baseline starting points when a patient is new to the system 102. Script data 124 may include descriptions of events relating to care to be followed on a repeating basis. Profile data 126 may include physiological attributes pertinent to diagnostic outcomes, which may represent a live status or state of a patient. The weather data 128 may represent an anticipated impact of future weather on upcoming scheduled events and may be used in forecast simulations. Traffic data 130 may represent regional traffic data ingested by an application programming interface to support the recommendation generator 142. Physician schedule data 110 may represent an availability of one or more physicians for an upcoming appointment. Staff schedule data 106 represents an availability of clinical staff. Equipment schedules 108 represent cleaning, maintenance, and/or other availability impacts for equipment used in appointments.

The appointment generator 144 may generate output including one or more indicators, appointments, user interface content, and calendar invites. For example, the appointment generator 144 may receive input from a patient that selected one or more of the schedule recommendations that recommendation generator 142 provided. Once the input is received, the appointment generator 144 may perform the scheduling of the selected appointment(s) for the patient. The appointment generator 144 may interface with available calendars 152 and virtual UI generator 154. For example, the appointment generator 144 may generate and provide information and UI screens (through virtual UI generator 154) to a patient to allow access to the scheduling system 102 and/or to interface virtually with one or more staff 106 or physicians 110. In some embodiments, patients may add additional clinical or personal appointments into a calendar 152 associated with system 102 to create a personalized scheduling availability. In some embodiments, the appointment generator 144 may represent user facing aspect of system 102 that may interact with the scheduling engine 112 to allow the user to act on provided recommendations.

In some embodiments, the calendar 152 may include or have access to data from a food diary in which the patient may enter meals and other intake each day. The system 102 may utilize data in the food diary (with user permission) to track bodily levels or other metrics with respect to food, drink, and medicinal intake. For example, the system 102 may detect a high risk food and use such a detection as a trigger to send messaging or log data pertaining to the risk. In a non-limiting example, the user may enter a food with a high salt or high potassium load and the system 102 may trigger messaging to avoid additional potassium for the day or to schedule an appointment for particular treatment if some combination of the high potassium food and other detected event(s) indicates indicate an increased probability of having a health event or hospitalization event.

In some embodiments, the calendar 152 may include or have access to data from a blood pressure device or other smart sensing device to allow patient blood pressures to be considered by the system 102 as a basis in which to trigger messages and/or appointment scheduling or rescheduling.

The communication engine 114 includes a message generator 160, an event detector 162, and a patient data detector 164. The message generator 160 may generate messages for patients, staff, and physicians based on the data assessed by scheduling system 102. The messages can include reminders, alerts, instructions, directions, appointments, appointment suggestions, UI content, or the like. For example, the system 102 may be arranged to request that a patient schedule enough sessions to meet requirements of a specific prescription for dialysis and any corresponding fluid removal. In addition, the system 102 may further be arranged to provide specific default time blocks according to appointment types, equipment types, and/or staff availability to ensure that a default selection of dialysis times is provided with each suggested appointment time or block of time. This can also ensure that a clinic (i.e., staff) will have time to complete a specific treatment in the appointment. If the patient scheduled too few sessions to meet such prescription requirements, the message generator 160 may generate and transmit an alert message for the patient and a corresponding notification (e.g., message) for an associated physician and/or staff. The message generator 160 may also provide patients with reminder messages for upcoming appointments. In addition, the message generator 160 may send patients indicators or messages when an opening in the schedule is available to allow the patient an opportunity to be dialyzed at a different, potentially more convenient time than a previously scheduled appointment. The specific time slots offered to patients may be offered based on time requirements indicated in a patient profile 126 (e.g., patient acuity profile). Changes that occur in patient receipt of dialysis that deviate from their originally scheduled treatments, such as missed or late appointments, may trigger automatic updates to patient profiles and/or may trigger generation of messages for the patient to allow the patient to self-schedule additional dialysis sessions. Further, if a patient is identified as high or imminent risk of hospitalization as determined by system 102, for example, a message may be generated and transmitted to the patient and/or staff. The message may include dialysis times in which to schedule a dialysis session. For example, if system 102 determines that a patient is at imminent risk of hospitalization based on assessing patient compliance, historical trends, and/or clinical parameters such as dramatic weight changes, the system 102 may trigger generation and transmission of a message to mitigate the risk.

The message generator 160 may generate and transmit messages to a patient based on a record of past schedule compliance and/or recognition incentives for being on-time and consistently diligent in receiving dialysis treatments. Patients that are tardy or absent from scheduled appointments may receive messages and/or reports regarding the tardiness or absence. Such messages and/or reports may also be transmitted to staff and/or physicians associated with the particular patient.

The message generator 160 may generate and transmit messages to clinicians (e.g., staff, technicians, physicians, or the like). For example, the message generator 160 may provide report messages to clinicians. The report messages may detail patient compliance and notices of missed dialysis sessions. In some embodiments, the scheduling system 102 may automatically analyze the schedule and recommend specific days/times for the clinician to perform rounds on patients to be able to maximize the number of their patients to be seen according to a particular cadence for clinical objectives and/or reimbursement objectives. In this way, non-nephrologist clinicians who treat the patients have access to the dialysis schedule for their patients and can schedule visits—either in person or virtually—with the patient during their sessions and message generator 160 may generate messages accordingly.

The message generator 160 may further generate report messages for clinicians based on patient data 104 (e.g., EMR data 120, weight data, fluid load trend data, lifestyle data, impedance measurements, blood pressure, measurements, etc.) obtained from patient at-home scales and/or wearable devices 132, for example. Clinicians can then make short-term or long-term changes to the patient's prescription. In some embodiments, the patient data detector 164 may detect such data and work with the analysis module 140, ML models 150, and message generator 160 to generate messages associated with detected patient data.

In some embodiments, the system 102 may generate a hospitalization index (not shown) that assesses and reports a 30 day, 60 day, 90 day, and/or 120 day probability of hospitalization for any given patient based at least in part on historical trends, compliance, comorbidities, etc. The hospitalization index may continually refine as additional data is added or available for each patient.

In some embodiments, generating messages based on fluid load trend data may be triggered by detecting or receiving data indicating that a patient should begin treatments for restoring circulatory volume, clearing of ketones, correction of electrolyte imbalances, etc. The system 102 may detect events related to such indications as a basis in which to trigger messaging and schedule appointments. In this way, the system 102 may make a first contact of the patient to trigger scheduling or rescheduling of appointments based on the detected events rather than relying on the patient to make first contact of the medical clinic. In addition, scheduling or rescheduling based on imminent patient need can ensure that appointments are available for need-based (e.g., life threatening or hospitalization inducing) events.

The event detector 162 may function to generate and trigger reminder messages through the message generator 160. The reminder messages may be sent to patients, staff, physicians, equipment, or other device or entity that may be scheduled to encounter a patient at a particular time. In some embodiments, the event detector 162 may detect that a particular at-risk patient may be well served to be dialyzed earlier than a scheduled appointment. In such examples, the event detector 162 may work with scheduling engine 112 and/or optimizer engine 116 to find an earlier appointment in which to reschedule the patient.

In some embodiments, the event detector 162 and/or patient data detector 164 may be programmed to monitor and assess patients that have provided permission to be monitored and/or location tracked. The event detector 162 and/or patient data detector 164 may use such monitoring and/or tracking to aid in determining likelihoods of patient adherence to scheduled dialysis session attendance. The event detector 162 may also utilize weather data 128 and traffic data 130 to trigger messages indicating weather alerts or timing alerts for when the patient should depart to ensure on time appointment arrival.

In some embodiments, the scheduling system 102 may receive consent from patients to allow the system 102 to obtain demographic data such as home address, patient data, and/or medical record data through electronic access or other access linked to the scheduling system 102. For example, the patient may consent to allowing an at-home Internet-connected scale to be linked to the scheduling system 102 to trigger transmission of data to the staff and/or physicians to alert of any unusual patterns in weight and/or fluid load. In some embodiments, weight or other biological metric may be received at system 102 by connected systems including electronic medical record systems, other clinics, and/or communicatively coupled applications, wearables, or other device. Such alerts may facilitate a change in the prescribed dialysis in a specific week or time frame. This new prescription can trigger alerts to the patient to schedule additional (or fewer) dialysis sessions in the system 102. In addition, messages may be sent to a computing device of the patient as a reminder to capture periodic weight measurements. Compliance of at-home weighing are also reports that may be generated and provided by system 102. Similarly, wearable or implantable devices may send additional data to trigger alerts regarding fluid load, blood pressure, electrolytes, blood sugar, or the like.

In some embodiments, each staff member may provide a staff profile 106 and staff credentials into the scheduling system 102, which may influence a staff-to-patient ratio during any one shift. Alternatively, the scheduling system 102 may obtain such information from another source and not directly from the staff members. In some embodiments, the staff schedule 10 may include both a fixed and a flexible scheduling component. Supervising staff can set fixed parameters (i.e. black-out dates) in order to meet the needs of the dialysis units. With a certain probability, the system 102 can inform when shifts will be expected to be under- or over-staffed which will in turn generate a rescheduling opportunity for the staff. Available shifts/dates for staff scheduling, will also be guided by staff profiles 106. The staff profiles 106 may account for credentials, training, seniority, and/or other factors as determined by the supervisor which may influence the desired team composition for any given shift.

The staff may also receive report messages (e.g., from message generator 160) on patient schedule adherence and alerts for late or missed sessions. The system 102 can provide messages through generator 160 to inform nurses and technicians if certain shifts will have a projected patient census which could cause a re-scheduling opportunity for the staff. In some embodiments, the message generator 160 may provide report messages to staff regarding projected patient census from the self-scheduling along with staff assignments to project expected reimbursement revenue and operating expenses to calculate forecasted financial results. The report messages can also inform the ordering of dialysis supplies and indicate dialysis machine maintenance. In some embodiments, the message generator 160 may also provide report messages to staff based on the patient scheduling to suggest when lab samples should be drawn and batched for central processing. In some embodiments, the scheduling system 102 can predict, based on the projected patient schedules, when the optimum time for lab sampling should occur.

The optimizer engine 116 may function to optimize schedules according to one or more parameters including, but not limited to optimizing for equipment use, down time, and maintenance; optimizing for patient or physician schedules; optimizing costs of using equipment and staff or physician time; and/or optimizing for or reducing patient risks with respect to schedule-based failures or lack of availability of equipment, staff, and physicians. For example, the field of dialysis treatment is dominated by two conventional for-profit companies, who have utilized the historical precedent of treatment occurring three times per week (i.e., Monday, Wednesday, Friday or Tuesday, Thursday, Saturday) at in-center hemodialysis operations. The conventional focus is on optimizing the utilization of dialysis equipment and the staff to operate the equipment, in order to minimize the cost of treating patients and maximize the profit of the center from reimbursement income. These set schedules for patients also simplify the operation and management of the treatment center. This conventional approach ignores unique patient preferences, work schedules, child care schedules, and potential changes in diet/behavior. Inflexibility of the schedule may cause missed dialysis sessions, which in some cases can lead to unplanned hospitalization. Conventional systems schedule dialysis centers focused on optimizing the staffing levels and for financial planning, and do not factor in the patient clinical outcomes. The system 102 may be tuned to optimize in such a conventional fashion, but additionally system 102 may provide an ability to tune schedules according to any number of optimization parameters, as described in detail herein.

The optimizer engine 116 includes a delay risk module 170, a patient risk module 172, a physician optimizer module 174, and a cost optimizer module 176. The delay risk module 170 may receive input that indicates a particular risk or assessment of delay of a patient, staff, physician, or equipment. For example, the scheduling system 102 may receive an input indicating one or more of: a drive time for the patient (e.g., traffic data 130), a weather input of the location (e.g., weather data 128), and a delay risk metric 171. The delay risk metric 171 may be an input or alternatively may be calculated based on one or more of: traffic data 130, a historical appointment attendance for the patient (e.g., stored in memory 180, stored in an EMR, and/or patient data 104), a schedule of one or more additional dialysis machines at the location (e.g., stored in memory 180 and/or scheduling engine 112 and/or calendars 152), or a schedule of one or more additional staff at the location (e.g., stored in memory 180 and/or scheduling engine 112 and/or calendars 152). The input or calculated delay risk metric may be used by scheduling system 102 to automatically update one or more dates and time generated for a patient by system 102. For example, if the system 102, through delay risk module 170, detects that the patient may be behind schedule by about 15 minutes, the system may reschedule the appointment for a later time (e.g., 15 minutes delay or more) and may trigger rescheduling for the associated staff, physician, and/or equipment reserved for the original appointment.

The patient risk module 172 may utilize input such as appointment cancellations, appointment absences, patient data 104, data received from wearable device 132 (or other implanted device or computing device), or the like to determine whether a patient is at risk of hospitalization. For example, the patient risk module 172 may detect that a cancellation input (or absence) has been documented for a patient and in response, module 172 may generate and output a second appointment time on a date within the patient's prescription window of time (for completing dialysis treatments) such that the patient is not put at risk solely because the patient could not obtain a new appointment within the prescribed window of time for dialysis sessions. For example, the scheduling system 102 may attempt to reschedule the patient within the prescribed window of time in order to avoid having the patient experience increased potassium, toxin buildup, demineralization, pulmonary edema, or other cardiovascular or metabolic issue as a result of missing a dialysis appointment.

In one non-limiting example, the scheduling system 102 may determine that a patient that cancelled or missed an appointment may be at a higher hospitalization risk than another patient on the existing schedule. In response, the system 102 may attempt to reschedule the second (and lower hospitalization risk) patient in order to provide a time slot for the first patient that is at the higher hospitalization risk, as described in detail in process 500 of FIG. 5 below.

The physician optimizer module 174 may generate optimized scheduling for a set of physicians to ensure that each particular physician may attend to patients during a time in which the patient is undergoing dialysis at a facility and within a time slot in which the physician is scheduled. For example, a physician (e.g., clinician) may have a rounds schedule that includes performing an evaluation of each patient from one to four times per month. In order to optimize rounding for the physician, the physician optimizer module 174 may assess patient scheduled appointments as a basis in which to allow the physician to round on the greatest number of patients within particular time period. For example, the physician optimizer module 174 may automatically analyze the schedule and may recommend specific days/times for patients based on a probability of rounding on the greatest number of patients within the time period. In this way, the system 102 provides an efficient way of scheduling physicians by understanding the overall needs of patients seeking appointment blocks over several weeks or months.

The cost optimizer module 176 may generate optimized scheduling of patients, staff, physicians, and/or equipment based on one or more inputs (e.g., patient data 104, staff data 106, equipment data 108, physician data 110, training data 151, and/or system variables, etc.).

The scheduling system 102 further includes one or more applications 177 (Apps). The apps 177 may include any number of applications, APIs, or access points to scheduling system 102. For example, patients may access an app 177 to enter input (as described herein elsewhere) for tailoring a set of appointments to a particular schedule or location. In this way, the patient may be part of the scheduling process.

The scheduling system 102 includes processors 178 and memory 180. The processors 178 may include one or more processors that include one or more devices capable of executing instructions, such as instructions stored by the memory 180, to perform communications amongst wearable device 132, user devices (not shown), scheduling system 100, scheduling system 102 (e.g., scheduling engine 112, communication engine 114, optimizer engine 116, ML models 150, ranking engine 148, calendars 152, and/or virtual UI generator 154, and/or third-party integrations (not shown)).

The memory 180 can include one or more non-transitory computer-readable storage media. The memory 180 may store instructions and data that are usable in combination with processors 178 to execute the processes and/or algorithms described herein as well as to execute or interface with ML models 150, scheduling engine 112 tasks, communication engine 114 tasks, and optimizer engine 116 tasks. The memory 180 may also function to store or have access to the ML models 150, scheduling engine 112, communication engine 114, and optimizer engine 116, and patient data 104, weather data 128, traffic data 130, physician schedules/profiles 110, staff schedules/profiles 106, and equipment schedules 108.

In some embodiments, the systems 100, 102 may further include or be communicatively coupled to input devices (not shown), output devices (not shown), and/or sensor interfaces (not shown). The input devices may interact with one or more processors 178, memory 180, and/or wearable device 132.

In some embodiments, the systems 100, 102 may further include or be communicatively coupled to output devices (not shown). The output devices may interact with one or more processors 178 and memory 180. In some embodiments, the output devices may include, for example, an external display for depicting user interfaces generated by virtual UI generator 154 and/or scheduling system 102.

FIG. 2A is an example schedule 200 generated by the system of FIGS. 1A-1B. The schedule 200 may be generated by scheduling system 102 to schedule 20 patients across 6 clinics at 6 locations (e.g., sites), for example. Although 6 clinics across 6 locations are used as an example, any number of clinics or locations may be used. In this example, each location includes 3 pieces of dialysis equipment, 4 staff members, and 2 physicians. Each appointment for each patient occurs at a single site for 3 hours and includes the patient, one staff member, and one optional physician and at least one piece of equipment. In this example, patient times are not overlapped, but given the number of staff, physicians and equipment, overlap could instead occur.

Here, row one 202 of the schedule includes a first patient (P1) is scheduled at site 1 at 9:00 AM with staff 1, physician 1, and equipment A at site 1. Similarly, patients P2 and P3 are scheduled at site one in the next two rows. Next, sites 2, 3, 4, 5, and 6 are scheduled for patients P4 through P20.

FIG. 2B is another example schedule 250 generated by the system of FIGS. 1A-1B. The schedule 250 is a partial schedule for the purpose of brevity. In the schedule 250, the scheduling system 102 generated open time slots 252-274 in the schedule to ensure that time slots remain open for last minute bookings and/or rescheduling. The open time slots may account for staff, physicians, and equipment that may be scheduled for patients at a future time.

Figure 3A:
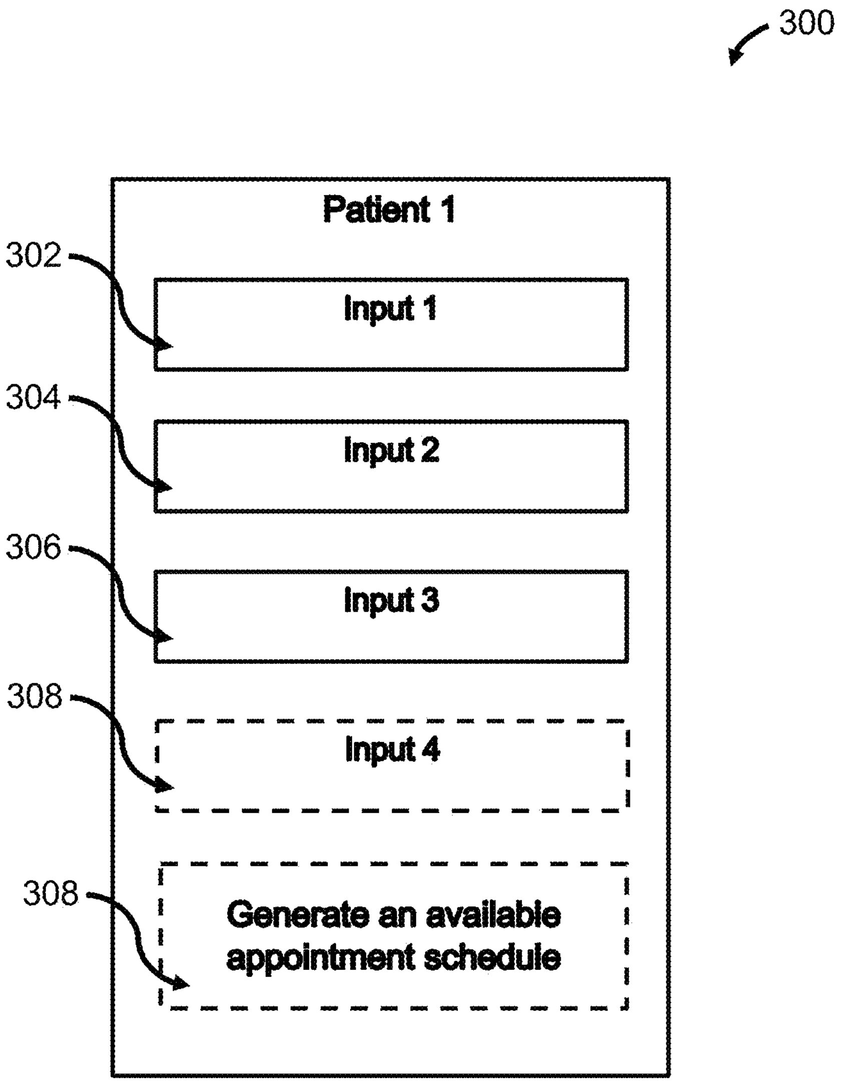
FIG. 3A is an example user interface generated by the system of FIGS. 1A-1B.

FIG. 3A is an example user interface 300 generated by the system of FIGS. 1A-1B. The UI 300 may be presented to a patient on a patient device (e.g., wearable device 132 or a computing device associated with the patient). In some embodiments, the UI 300 may be part of an app (e.g., apps 177) provided by scheduling system 102 to a patient, staff member, or physician. The app 177 may be used to enter inputs. In some embodiments, the inputs may be obtained from data available to scheduling system 102 and may be automatically obtained, rather than entered by any user.

In this example, the app 177 may be provided to patient 1 where any or all of an input 302, an input 304, an input 306, and an optional input 308 may be received from patient 1 or otherwise obtained by system 102 as described elsewhere herein. In some embodiments, a single input may be provided. In some embodiments, two inputs may be provided. In some embodiments, three inputs may be provided. In some embodiments, four or more inputs may be provided.

Upon one or more inputs being provided with respect to UI 300, an optional selectable button 310 may be provided to allow the patient to generate an available appointment schedule. In some embodiments, the button 310 is not provided and instead system 102 automatically generates an available appointment schedule based on available input provided (e.g., input 302, input, 304, input 306, and/or input 308).

Figure 3B:
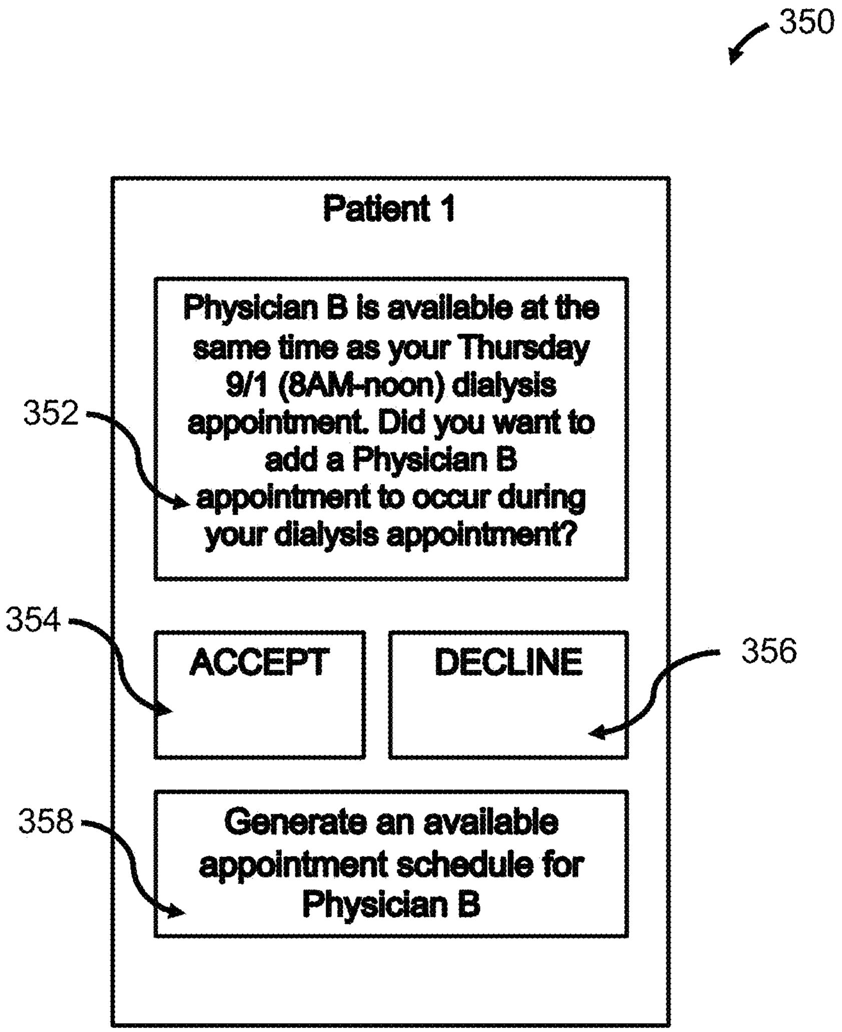
FIG. 3B is an example user interface generated by the system of FIGS. 1A-1B.

FIG. 3B is an example user interface 350 generated by the system of FIGS. 1A-1B. The UI 350 may be presented to a patient on a patient device (e.g., wearable device 132 or a computing device associated with the patient) in response to determining that the patient has a dialysis appointment at a first time and is also in need of a physician visit. In some embodiments, the UI 350 may be part of an app (e.g., apps 177) provided by scheduling system 102 to a patient, staff member, or physician. The app 177 may be used to enter inputs for accepting suggested appointments and/or generating additional possible appointment schedules.

As shown, a message is provided indicating possible add on appointments for the patient 1. For example, the message generator 160 may have generated the message containing an indication having one or more appointment indicators 352. In this example the indicator 352 includes a message that "Physician B is available at the same time as your 9/1 (8 AM-noon) dialysis appointment. Did you want to add a Physician B appointment to occur during your dialysis appointment?" The indicator 352 may instead include any number of appointment times, questions, or the like. For example, the message generator 160 may generate and transmit one or more dates and time periods to a scheduling system (e.g., scheduling system 102 or another external system) of one or more physicians for treating a secondary condition of the patient and may determine an overlap (e.g., through scheduling engine 112) between the schedule of the one or more physicians (e.g., through calendars 152) and the one or more dates and time periods. In response to finding the overlap, the message generator 160 may send the proposed dates/time periods through a UI or message including UI content (e.g., such as UI 350). The patient may receive the UI 350, and accept 354 or decline 356 the proposed appointment. In some embodiments, the appointment is a virtual appointment between the patient and the one or more physicians during the dialysis machine usage by the patient. In some embodiments, the appointment is an in-person appointment between the patient and the one or more physicians during the dialysis machine usage by the patient.

If the patient accepts 354 the proposed appointment (or selects one of the appointments from the proposed appointments), then the scheduling engine 112 may schedule an appointment with the one or more physicians during the one or more dates and time periods. If the patient declines 356 the proposed appointments or selects another option, other actions may be performed by system 102. For example, UI 350 includes a selection 358 to generate an available appointment schedule for Physician B. If the patient selects selection 358, then the scheduling system 102 may use physician schedules/profiles 110 and/or calendars 152 to generate the appointment schedule for Physician B and provide such a schedule to the patient.

Figure 4:
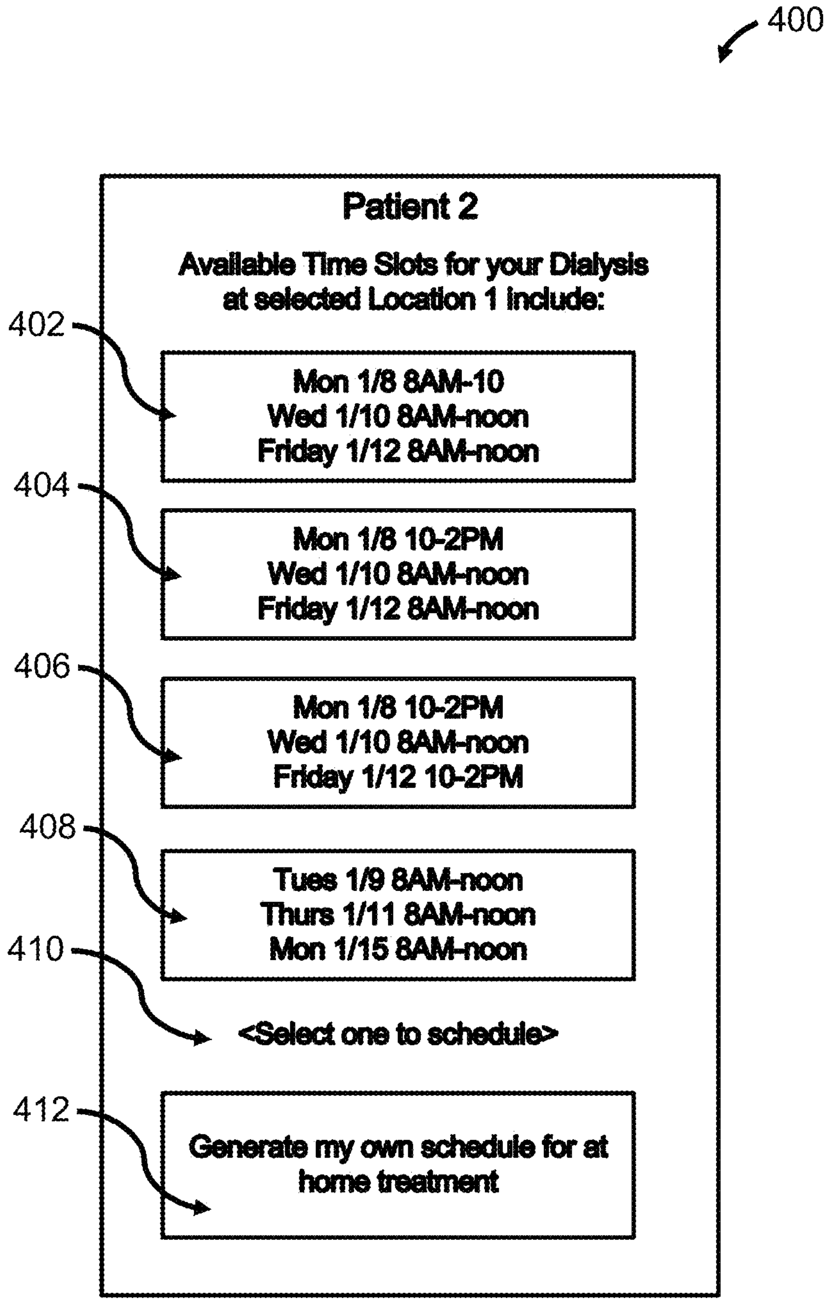
FIG. 4 is another example user interface generated by the system of FIGS. 1A-1B.

FIG. 4 is another example user interface 400 generated by the system of FIGS. 1A-1B. The UI 400 may be presented to a patient on a patient device (e.g., wearable device 132 or a computing device associated with the patient) in response to determining that the patient has a prescription for dialysis treatment. In some embodiments, the UI 400 may be part of an app (e.g., apps 177) provided by scheduling system 102 to a patient, staff member, or physician. The app 177 may be used to provide access to scheduling system 102 for a patient, staff member, or physician and to enter inputs for accepting suggested appointments and/or generating additional possible appointment schedules.

As shown, a message is provided indicating available time slots for dialysis for patient 2 at a selected location 1. The time slots include indicators 402, 404, 406, and 408 depicting appointment series of 2 or 4 hour blocks. The patient 2 may select from one of the appointment series to trigger system 102 to schedule the appointments, as indicated by text indicator 410. In addition, an indicator 412 to generate the patient's own schedule for at home treatment is also provided to trigger the system 102 to offer appointments in which equipment and staff and/or physicians are available for home-based visits and treatment.

Example Processes

Figure 5:
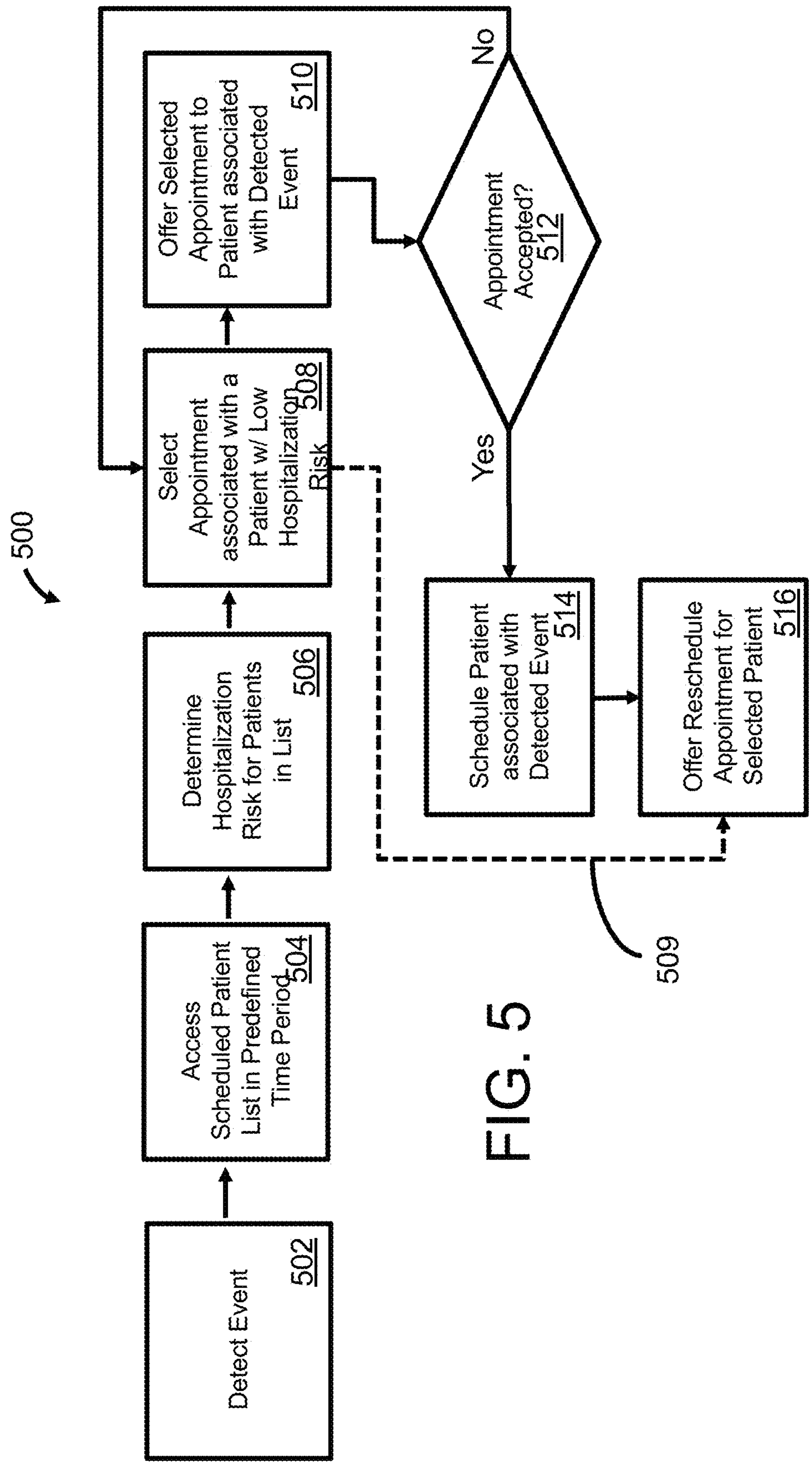
FIG. 5 illustrates a flow diagram of an example process for rescheduling patients.

FIG. 5 illustrates a flow diagram of an example process 500 for rescheduling patients. In some embodiments, the process 500 may be performed by scheduling system 102 and in particular, by optimizer engine 116 to assess particular patient risks and/or communication engine 114 to detect particular system or patient events. Ranking engine 148, ML models 150, calendars 152, and/or virtual UI generator 154 may also be used in one or more steps of the process 500. In some embodiments, the process 500 may be carried out by one or more ML algorithms using ML models 150, for example.

At block 502, the process 500 includes detecting an event. For example, the delay risk module 170 may determine that a first patient cancelled or missed an appointment and because of the cancellation (or other input), the first patient may be at a higher hospitalization risk than a second patient on the existing schedule. In one non-limiting example, the event detector 162 and/or the patient data detector 164 may detect a medical anomaly in data captured or received from the first patient and/or an event indicating distress or medical decline of the first patient. In response, the system 102 may attempt to reschedule the second (and lower hospitalization risk) patient in order to provide a time slot for the first patient to mitigate the hospitalization risk. In some embodiments, the detected event may be received in an app 177 accessed by the patient. The process 500 may detect such events and proceed to assist the patient in rescheduling one or more appointments.

For example, at block 504, the process 500 may include accessing one or more scheduled patient lists that fit a predefined time period allotted for the first patient in a prescribed dialysis protocol associated with the first patient. The scheduling engine 112 may use analysis module 140 and/or ML models 150 to assess whether an opening can be made in the schedule for the first patient to receive medical care (e.g., dialysis, physician care, etc.). For example, the optimizer engine 116, and in particular, the patient risk module 172 may determine a hospital risk for patients in the patient lists, at block 506, to assess whether any patient can delay a scheduled appointment and remain a low risk of hospitalization. The patient risk module 172 can determine any number of appointments that may be rescheduled for another patient in order to allow the first patient to avoid a hospitalization risk.

At block 508, the process 500 includes selecting one or more appointments associated with a patient with a low hospitalization risk. For example, the patient risk module 172 may select one or more appointments associated with one of the low risk patients determined herein. The selected one or more appointments may be candidate choices for rescheduling. In some embodiments, selecting the one or more appointments for reschedule may include generating and sending messages to respective patients that may be rescheduled to request whether a respective patient would tolerate or accept such a rescheduling or to entirely reschedule the respective patient, as indicated by arrow 509.

At block 510, the process 500 includes offering a selected appointment to the first patient. For example, the scheduling system (e.g., the message generator 160) may generate a message for the patient associated with the detected event (i.e., the first patient) to offer the selected appointment(s).

At block 512, the process 500 includes detecting whether one or more of the offered appointments has been accepted by the first patient. For example, the event detector 162 can detect if the first patient accepted an appointment. If the first patient did not accept the appointment, then the system 102 can return to block 508 to generate and select additional appointment candidates to offer to the first patient. If the first patient did accept one or more of the offered appointments, the system 102 may schedule the first patient, at block 514. For example, the scheduling engine 112 may generate the appointment in the system 102 for any staff, equipment, and/or physicians and may schedule the first patient at the time(s) and day(s) of the offered one or more appointments.

At block 516, the process 500 includes offering one or more rescheduling appointments for the patient(s) in which an appointment was selected for rescheduling. For example, the message generator 160 may generate and transmit a message to the second patient (having a lower hospitalization risk than the first patient). The message may include and/or otherwise provide for alternative appointment date (s)/time(s) for the second patient to accommodate a new appointment for the second patient while still following the prescribed treatment time period associated with the second patient.

In operation of process 500, the system 102 may have scheduled a number of appointments for any number of patients. At some point in time, the system 102 may receive a cancellation input (e.g., from the first patient) indicating cancellation of a previously schedule first time period on a first date. The system 102 may generate and output to the first patient, a health impact message when a second time period on a second date within the predefined time window is not selected. In this example, the first patient may have cancelled due to a personal scheduling conflict. The system 102 can determine that this would be a health risk to the first patient and may automatically attempt to reschedule the cancelled appointment for another time that is still within the prescribed time window for dialysis treatments in a week, for example. In particular, the message generator 160 may function with the recommendation generator 142 to generate and recommend an output of an appointment at a second time period on a second date within the predefined time window of the first patient. Such an assessment may ensure that the patient is offered a new appointment that is still within treatment guidelines for the week, for example. The rescheduling process may involve additional patients in the event that the schedule is full. For example, additional messages and rescheduling tasks can be sent to other patients with a lower hospitalization risk than the first patient. The messages may provide alternative appointment dates for the second patient to accommodate the second time period on the second date for the patient (e.g., as described in detail herein).

Figure 6:
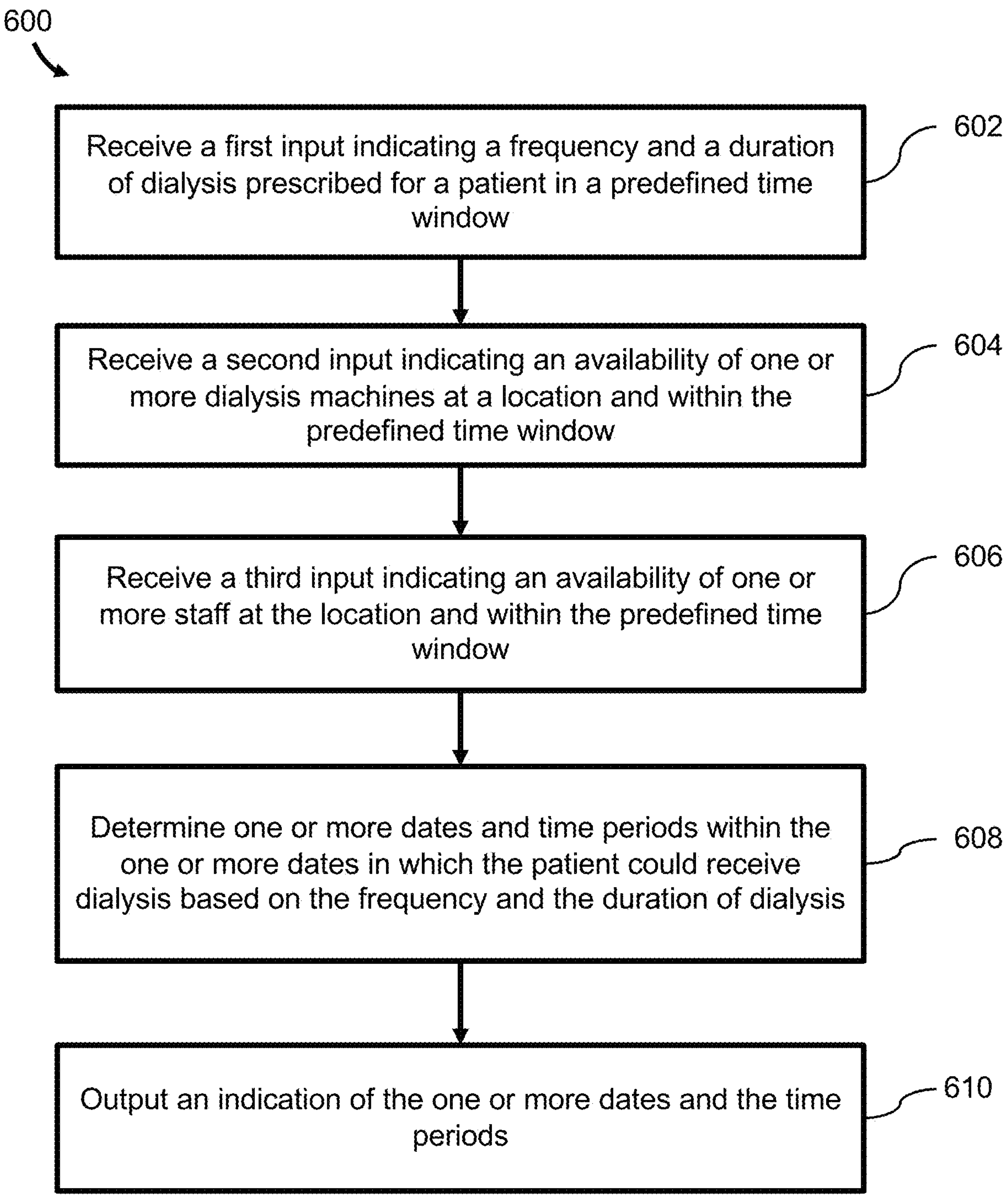
FIG. 6 is a flow diagram of an example process for generating scheduling options that optimize dialysis machine usage.

FIG. 6 is a flowchart of an example process 600 for generating scheduling options that optimize dialysis machine usage. In some embodiments, the process 600 may be performed by scheduling system 102 and in particular, by scheduling engine 112, optimizer engine 116, and communication engine 114. Ranking engine 148, ML models 150, calendars 152, and/or virtual UI generator 154 may also be used in one or more steps of the process 600. In some embodiments, the process 600 may be carried out by one or more ML algorithms using ML models 150, for example.

At step 602, the process 600 includes receiving a first input (e.g., input 302) indicating a frequency and a duration of dialysis prescribed for a patient in a predefined time window. For example, a physician, a staff member, or a patient may provide the first input in a user interface (e.g., UI 300) provided by the scheduling system 102. In some embodiments, the first input may be obtained by system 102 automatically by accessing calendars 152 and/or patient data 104 and/or schedules 122.

In some embodiments, the first input may include a prescription in text or image format. In some embodiments, the first input may include data obtained from dropdown elements, radial selections, and/or text fields presented in UI 300 and accessible to system 102 upon completion of patient entry of inputs, for example. In some embodiments, the first input may be a provider name or location in which the patient typically receives treatments. The entered provider name may trigger access by system 102 to a provider database that may provide patient information (e.g., prescription) according to user preferences and/or user permissions. The access to the provider database may enable system 102 to query the database to obtain patient details and/or prescription information and thus provide the system 102 with reference to a number of treatments that should occur within a predefined period indicated by the prescription. In this way, the system 102 ensures that a patient does not extend or shorten the time of the treatments or the time between treatments. In some embodiments, the system 102 may use a provider database to verify a prescription based on the patient data and may do so without the input of the provider's name or location.

Although a single patient may be referenced in the processes described herein, the term "patient" may refer to a plurality of patients in which each patient has a corresponding individualized frequency and duration of dialysis in an individualized, predefined time window. For example, when the processes 500 and/or 600 are indicated to access, modify, or query data about a single patient, data for any number of patients may instead be accessed, modified, or queried. Such access to multiple patients can ensure that process 500 and process 600 may schedule, reschedule, and query any number of patients in real time with scheduling system 102. In such examples, the system 102 may offer a way for staff/schedulers/providers to query the appointments and calendars 152 in the system while also offering patients a way to access data to find convenient appointments according to prescription timing. Thus, the scheduling system 102 provides an automated and simultaneous way to query, schedule, and reschedule appointments on the staff/schedulers/providers side and the patient side in real time.

At step 604, the process 600 includes receiving a second input (e.g., input 304) indicating an availability of one or more dialysis machines at a location and within the predefined time window. For example, a physician or a staff member may provide the second input in a user interface (e.g., UI 300) provided by the scheduling system 102. In some embodiments, the second input may be obtained by system 102 automatically by accessing calendars 152 and/or equipment schedules 108 and determining availability windows of time for the equipment at a particular location. Such availability windows may be compared and matched to the predefined time window associated with the patient prescription to find an overlap in availability between both equipment and patent schedules. Accordingly, the input may be obtained by system 102 and presented in UI 300 as options in which to select particular dialysis machines or particular locations. The second input and subsequent presentation of options of equipment can be based on scheduled appointments, scheduled equipment maintenance, staff availability, etc.

At step 606, the process 600 includes receiving a third input (e.g., input 306) indicating an availability of one or more staff at the location and within the predefined time window. For example, a physician or a staff member may provide the third input in a user interface (e.g., UI 300) provided by the scheduling system 102. In some embodiments, the third input may be obtained by system 102 automatically by accessing calendars 152 and/or physician schedules/profiles 110 and/or staff schedules/profiles 106. The third input may include physician schedules, staff schedules, physician or staff preferences, vacation schedules, or the like.

In some embodiments, the third input may be obtained by system 102 automatically by accessing calendars 152 and/or physician schedules/profiles 110 and/or staff schedules/profiles 106 and determining availability windows of time for the staff and/or physician that overlaps availability for the equipment and the patient. For example, the physician and/or staff availability windows may be compared and matched to the predefined time window associated with the patient prescription to find an overlap in availability between staff/physician and patent schedules. Accordingly, the third input may be obtained by system 102 and presented in UI 300 as options in which to select particular staff and/or physicians.

At step 608, the process 600 includes determining one or more dates and time periods within the one or more dates in which the patient could receive dialysis based on the frequency and the duration of dialysis. For example, the analysis module 140 may assess the first input, the second input, and the third input to determine suggestions of appointments or appointment series that may be presented to one or more patients. The suggestions may include one or more dates and the time periods that are aligned with the availability of the one or more dialysis machines and the availability of the one or more staff. In some embodiments, the process 600 may determine the availability of the one or more staff based on a schedule (e.g., staff schedules/profile 106) for each staff and one or more predefined staffing ratios. For example, predefined staffing ratios may indicate a staff-to-patient ratio of about 1 to 2; about 1 to 3, about 1 to 4; or about 1 to 5 to ensure patient safety and positive patient outcomes. Thus, scheduling suggestions can be based at least in part on staffing ratios.

In some embodiments, the second input associated with location may include a plurality of locations, such that the one or more dialysis machines include any number of dialysis machines. In some embodiments, the third input associated with one or more staff may include any number of technicians available to operate any of the dialysis machines. In this way, a user can select particular staff and particular physicians based on the availability and details for each location and/or piece of equipment. In such examples, the process 600 may further include determining the one or more dates and time periods in which the patient could receive dialysis at a particular one of the plurality of locations and the time periods within the one or more dates in which the patient is recommended to receive dialysis based on the frequency and the duration of dialysis. Thus, the system 102 may narrow location options to a single location based on any one or more of a patient address, traffic information, patient delay, patient preferences, and/or physician requests. In some embodiments, the system 102 may narrow location options to two or three locations based on any one or more of a patient address, traffic information, patient delay, patient preferences, and/or physician requests.

At step 610, the process 600 includes outputting an indication of the one or more dates and the time periods in which the patient may wish to schedule appointments. The indication may include a message. For example, the indication may include an email, a calendar invite, an indicator in a UI (e.g., UI 400), a text message, an app based UI or indication, a phone call with prompts, etc., or the like. In some embodiments, the indication may include an optimized schedule for the patient for a week, a month, a year, etc. The optimized schedule may be based on health risks, cost risks, and/or other input that may affect patient adherence to a dialysis schedule. The patient may accept and/or decline suggested indications of appointments, as described in detail elsewhere herein. For example, if the patient wishes to accept one of the offered appointments, the patient may select the appointment. In response, the scheduling system 102 may receive the selection as input, for example, to select a first time period of the one or more time periods on a first date of the one or more dates.

In some embodiments, the process 600 further includes receiving a fourth input (e.g., optional fourth input 308) indicating one or more of: a drive time for the patient, a weather input of the location, and a delay risk metric. The fourth input may be automatically obtained by system 102 or entered by a patient into a UI generated by system 102. In some embodiments, the fourth input may include a drive time for the patient based on traffic input 130 and/or location tracking information and/or address information associated with patient data 104. In some embodiments, the fourth input may include a weather input associated with the location of suggested appointments and such input may be obtained by weather input 128. In some embodiments, the fourth input may include a delay risk metric indicating that a patient may be at risk of arriving late to an appointment. The delay risk metric may be calculated based on one or more of the traffic data 130, a historical appointment attendance for the patient, a schedule 108 of one or more additional dialysis machines at the location, or a schedule 106 of one or more additional staff at the location. The delay risk metric may be used to reschedule the patient and/or trigger modifications at the site of the appointment for staff, physicians, and/or equipment. For example, the fourth input may be used to enable the scheduling system 102 (i.e., the scheduling engine 112) to automatically update the one or more dates and the time periods for the patient.

In some embodiments, the fourth input includes input indicating one or both of: a fluid load or a lifestyle metric of the patient. For example, the wearable device 132 may be polled to obtain such information. In some embodiments, the patient may provide specific fluid load or lifestyle metric input (e.g., eating habits between dialysis appointments, alcohol intake, controlled substance intake, exercise schedule, etc.) in an app associated with (or in communication with) scheduling system 102. In response to receiving such input, the scheduling system 102 may automatically update the one or more dates and the time periods according to the received fluid load or lifestyle metric(s).

In some embodiments, the received fluid load may be based on one or both of: a historical weight gain of the patient or a historical fluid removal rate during dialysis of the patient. Such information may be obtained from an internet-connected scale that captures the weight of the patient over time, received from user input, or accessed from an EMR of the patient. The weight over time may be used by system 102 to determine the historical weight gain of the patient. Such weight assessments and fluid levels may be used as a basis in which to generate additional appointments, reschedule appointments, cause health related messages to be sent to the patient, etc. For example, the scheduling system 102 may receive a fourth input indicating a volume of fluid removed from the patient during a previous time period on a previous date. The system 102 may determine whether scheduling is to be changed according to the newly received input and in response to such a determination, may automatically update the one or more dates and the time periods.

In some embodiments, receiving the fourth input includes receiving historical data that includes appointment frequency per time period for a physician. Such input may be used to automatically update the one or more dates and the time periods to fall within a window of higher appointment frequency for the physician. This can ensure that a physician can time block appointments at particular locations to avoid increasing costs pertaining to physician travel time, physician wait time, and physician down time.

In some embodiments, the received inputs described herein may be received in one or more apps 177 communicatively coupled to the scheduling system 102. Patients, staff, and physicians may have access to such apps 177.

Figure 7:
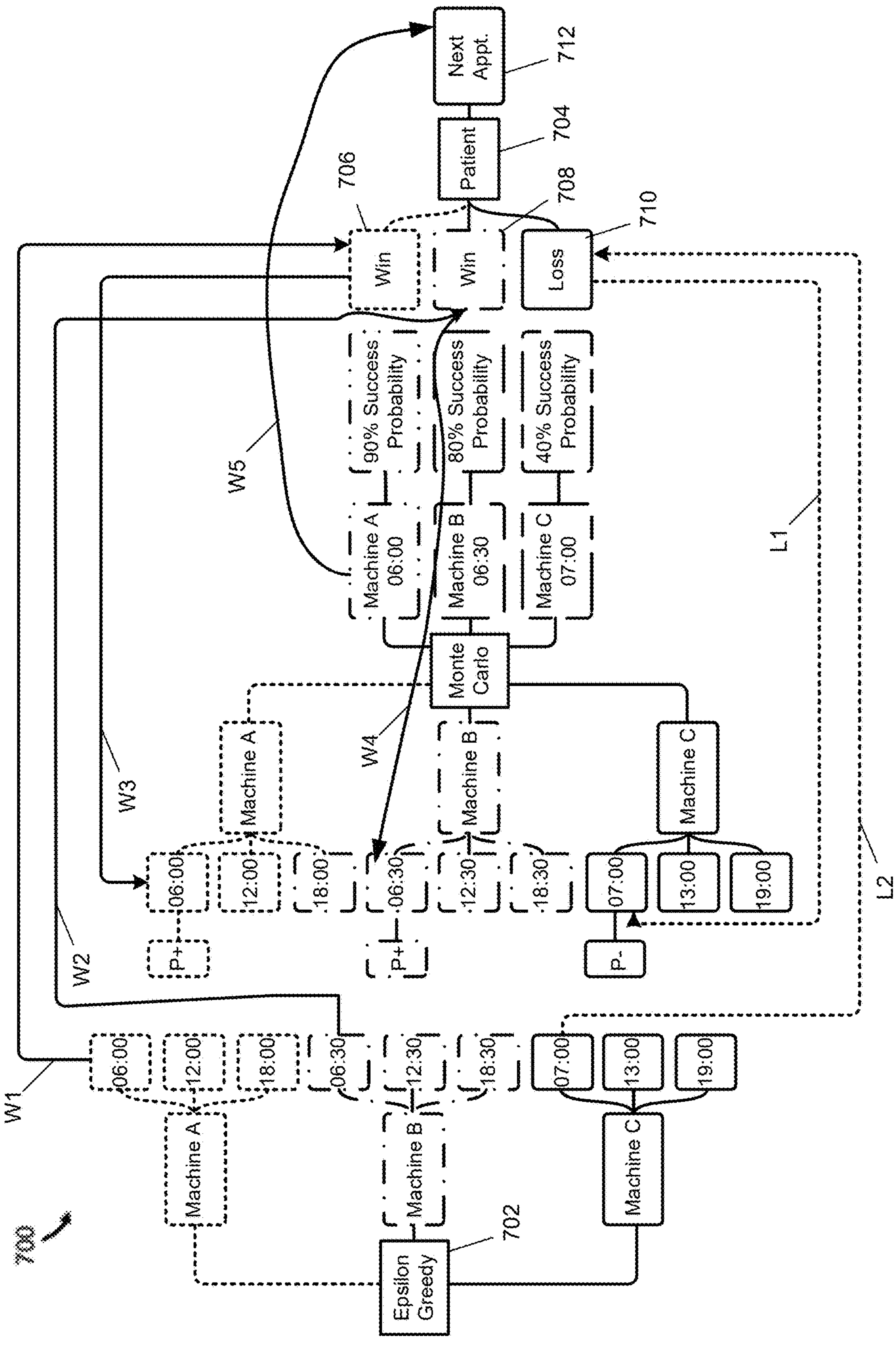
FIG. 7 is an example appointment selection process for use with the system of FIGS. 1A-1B.

FIG. 7 is an example appointment selection process 700 for use with the system of FIGS. 1A-1B. An Epsilon-Greedy node 702 may utilize one or more ML models to determine whether predicted scheduling recommendations will be accepted by a patient (e.g., a win) or whether such predicted scheduling recommendations will be rejected by the patient (e.g., a loss).

In this example, machine A, machine B and machine C may each represent a dialysis machine (e.g., or other equipment). Each machine is depicted with three corresponding time blocks available for machine utilization. While three time blocks are shown, any number of time blocks may instead be substituted (e.g., 4, 5, 6, 7, 8, 9, 10, 11, 12 . . . 24 time blocks).

The arrows W1, W2, W3, W4, L1, and L2 that extend from a time block to the win (win 706, win 708) or loss 710 for the patient represent attempts by the algorithm to determine one or more ideal appointment windows for the patient. The W1, W2, W3, and W4 arrows represent appointments that were considered Wins; the L1 and L2 arrows represent appointments that were considered losses.

In operation, the system 102 may suggest recommended next appointments to a patient or to a user that sets a patient's schedule. The suggested next appointments are derived using one or more Monte Carlo simulations, as described elsewhere herein, which may employ algorithms utilized by the Epsilon-Greedy node 702. The system 102 selects future appointments that have a high probability of being wins and provides the selections as suggestions to the patient or other user setting a schedule. In this example, the suggested appointment is shown by W5, which is presented to the user/patient as an option for the next appointment 712 based on being determined by system 102 to have a 90% probability of success of being selected by the user/patient. Any choice selected by the patient or the user setting the schedule may be considered in future iterations of the algorithm. For example, selections may be considered weighting factors for any given machine or time window configuration in future appointment suggestions.

Figure 8:
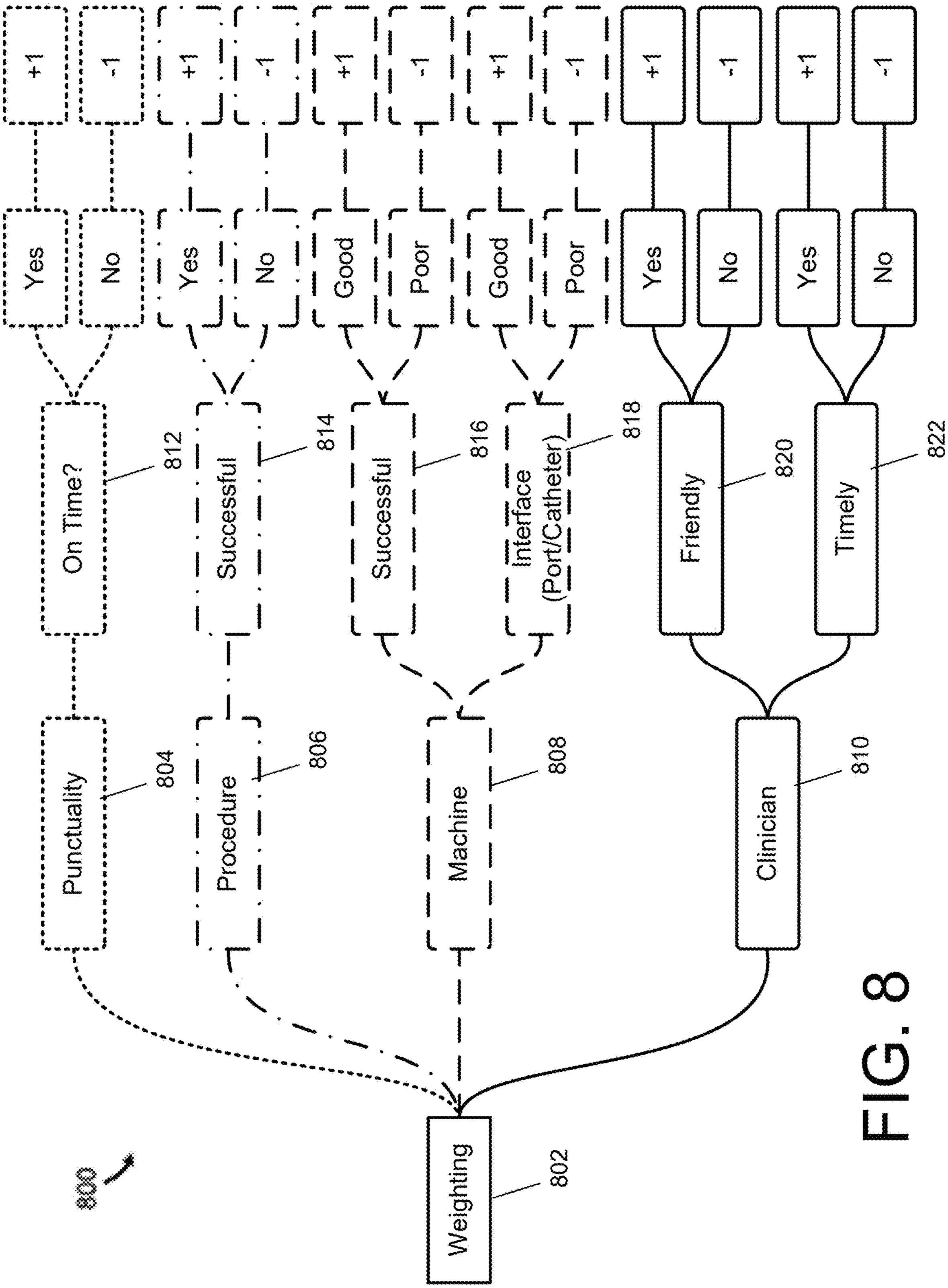
FIG. 8 is an example weighting process for use with the system of FIGS. 1A-1B.

FIG. 8 is an example weighting process 800 for use with the system of FIGS. 1A-1B. The process 800 may assign numerical values to various factors, such as punctuality metrics, procedure success metrics, machine performance metrics, nurse interaction metrics, and the like. These values may be combined to generate an overall patient experience score.

In general, the process 800 may provide a quantitative approach to evaluating patient experience. In some embodiments, the process 800 may provide customization of weightings based on specific priorities or preferences. In some embodiments, the process 800 may be used to identify areas for improvement in patient care.

In a non-limiting example, the process 800 may assign weights based on punctuality 804, procedure 806, machine 808, and/or clinician 810. The weights generated by performing weighting 802 may provide an overall patient experience score. The punctuality 804 may be weighted based on whether a patient arrived on time 812 for one or more prior appointments. A positive weight may be assigned for on-time arrivals, and a negative weight may be assigned for late arrivals.

In a non-limiting example, the process 800 may assign weights based on a particular procedure being successful 814 or not. For example, the system 102 may evaluate a success of a dialysis procedure. A positive weight may be assigned for successful procedures, and a negative weight may be assigned for unsuccessful procedures.

In a non-limiting example, the process 800 may assign weights based on a machine successfully operating and/or factors such as flow rate and interface quality 818 of a port/catheter, for example. Positive weights may be assigned for good performance, and negative weights may be assigned for poor performance.

In a non-limiting example, the process 800 may assign weights based on performance or demeanor of a clinician (e.g., nurse, doctor, technician, etc.). For example, the system 102 may assesses the friendliness 820 and/or timeliness 822 of a clinician. Positive weights may be assigned for positive interactions, and negative weights may be assigned for negative interactions.

Figure 9:
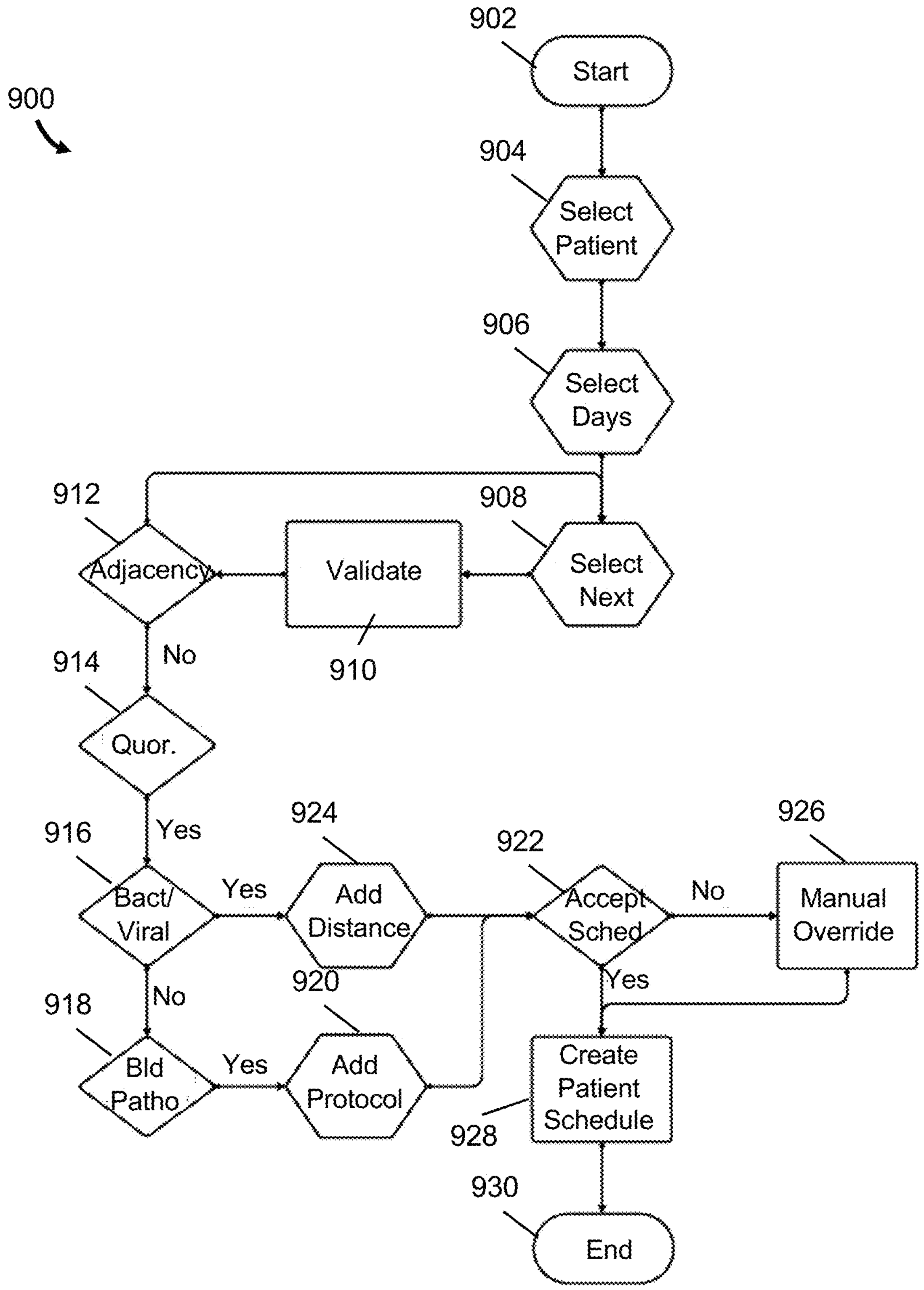
FIG. 9 is a flow diagram of an example scheduling process for use with the system of FIGS. 1A-1B.

FIG. 9 is a flow diagram of an example scheduling process for use with the system of FIGS. 1A-1B. The process 900 may additionally function to carry out some or all aspects of block 608 of FIG. 6. In some embodiments, the process 900 functions to schedule patient appointments. For example, the process 900 may be used for dialysis scheduling but can additionally or alternatively be used for any suitable applications, clinical or otherwise. The process 900 can be configured and/or adapted to function for any suitable application for scheduling patients. In general, the process 900 may prioritize patient safety by considering quarantine restrictions and implementing appropriate protocols while offering flexibility by allowing for manual schedule adjustments.

The process 900 may be performed by system 102. The system 102 may begin by selecting a patient and then may proceed to select available days of the week for scheduling. The system 102 may validate the schedule, considering factors such as adjacency issues and quarantine restrictions. If issues arise, the system 102 may add distancing protocols or manually override the schedule. If no issues are identified, the system 102 may generate a patient schedule and ends the scheduling process.

At block 902, the process 900 may include initiating the scheduling of a patient with equipment and/or clinician(s). At block 904, the system 102 may select a patient for scheduling. At block 906, the system 102 may identify available days of the week for the selected patient. At block 908, the system 102 may select a next available time block. At block 910, the system 102 may validate the schedule by checking for any scheduling conflicts. For example, the system 102 may check for adjacency issues, at block 912, quarantine issues, at block 914, bacterial or virulence issues, at block 916, and/or blood borne pathogen issues, at block 918. If there are adjacency issues, the process 900 returns to select a next available time block at block 908. If there are no adjacency issues, then the process 900 determines whether there are quarantine issues and/or bacterial virulence issues. If either is true for the selected patient, then process 900 may indicate to add distancing to the appointment, at block 924. If there are neither are true, then the process 900 may determine whether blood borne pathogen issues are present for the selected patient, at block 918. If there are no blood pathogen issues, then process 900 may skip to block 922. If there are blood pathogen issues, the process 900 may move to block 920 to add Medicare or other pathogen protocols to the appointment.

The determined appointment may be provided to the patient for approval or denial, as described elsewhere herein. Any number of determined/recommended appointments may be sent to the patient to provide options in which to allow the patient to choose from many recommended appointment times/days (or sets of appointments). If the patient rejects a suggested appointment (or set of appointments), then the process 900 may enable the user to manually override schedule adjustments, at block 926. If the patient accepts a suggested appointment (or set of appointments), then the process 900 generates the patient schedule according to the selected days/times, at block 928, which ends scheduling, at block 930.

Figure 10:
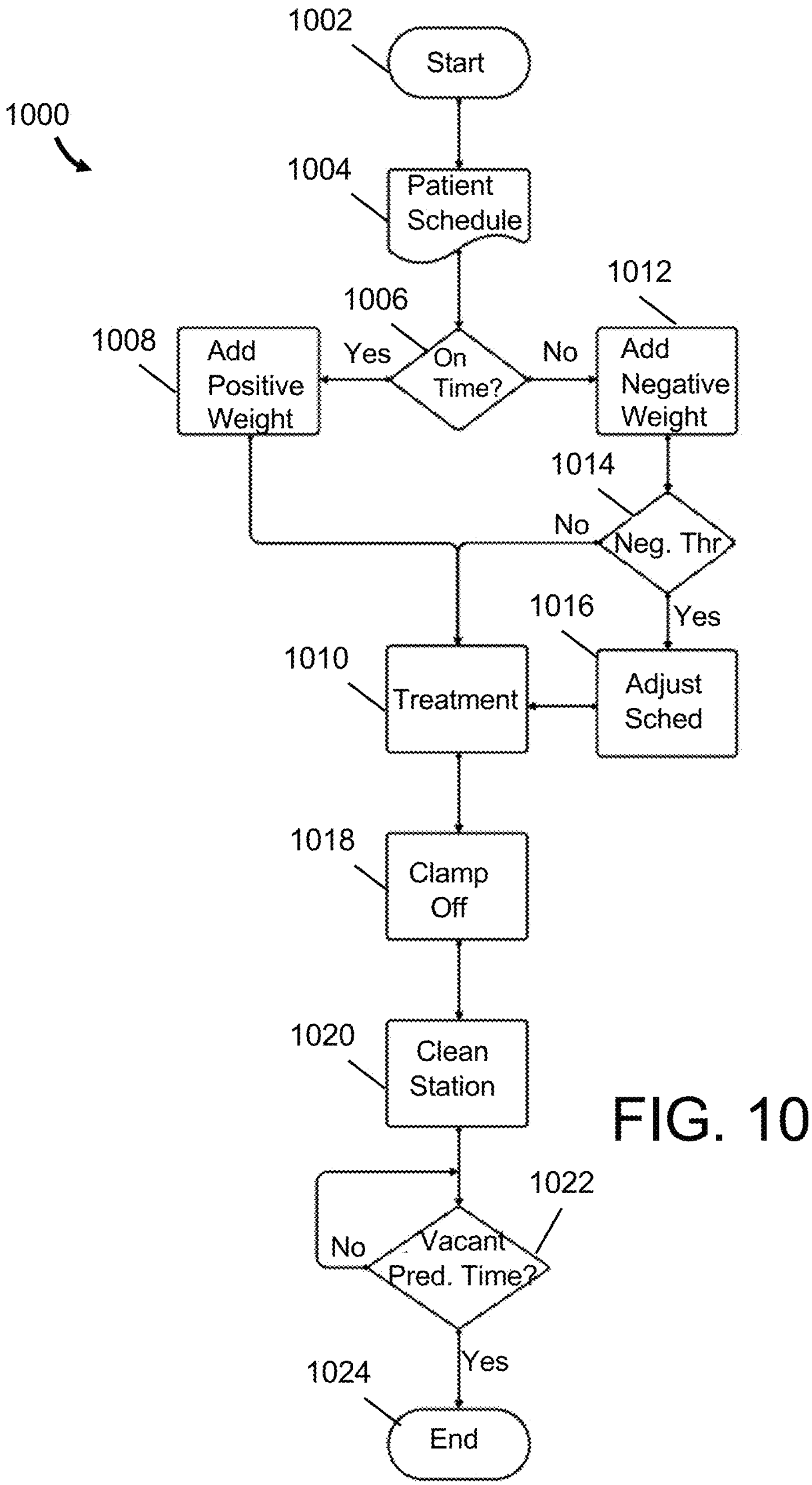
FIG. 10 is a flow diagram of an example weighted scheduling process for use with the system of FIGS. 1A-1B.

FIG. 10 is a flow diagram of an example weighted scheduling process 1000 for use with the system of FIGS. 1A-1B. The process 1000 may prioritize patient punctuality by adjusting schedules based on negative weights and/or positive weights. In some embodiments, the process 1000 ensures efficient station utilization by monitoring vacancy time. In some embodiments, the process 1000 functions to schedule patient appointments. For example, the process 1000 may be used for dialysis scheduling but can additionally or alternatively be used for any suitable applications, clinical or otherwise. The process 1000 can be configured and/or adapted to function for any suitable application for scheduling patients.

The process 1000 illustrates a system and method for managing patient treatment and scheduling. The process 1000 may begin by initiating the scheduling process and assessing an on-time status (e.g., using punctuality metrics associated with prior user visits, traffic data, weather data, etc.). The process 1000 may use the punctuality metrics to adjust the schedule accordingly based on predefined negative thresholds, for example.

At block 1002, the process 1000 may include assessing one or more prior visits according to a start time, at block 1002, and a patient schedule, at block 1004. The assessment may include determining whether the patient was on time for one or more prior appointments, at block 1006. If the patient was on time for a particular appointment, the process 1000 may add a positive weight associated with the timing of the prior appointment, at block 1008. The process 1000 may continue to schedule the treatment for the patient at the proposed time, at block 1010.

If the patient was not on time for the particular appointment, then the process 1000 may add a negative weight associated with the timing of the prior appointment, at block 1012. Each prior appointment can be assessed in a similar fashion. The process 1000 may determine whether any added negative weight pushes an overall weighting of any particular appointment over a negative threshold, at block 1014.

Examples of a negative threshold may include a consistently missed appointment window eventually losing enough weight that it falls out of the recommendation list. The overall sensitivity of the system 102, which triggers this behavior may be a modifiable parameter, consistent with an implementation of Epsilon-Greedy algorithms. In Epsilon-Greedy terms, the system 102 may shift from an exploitation state to a discovery state, seeking a more efficient appointment window aggressively instead of continuing to schedule an unfruitful appointment time.

If the added negative weight pushes the overall weighting over the negative threshold, then the process 1000 may adjust the schedule to suggest a different appointment time (or set of appointment times) to accommodate for the likelihood of the user being tardy to future appointments. Upon adjusting the schedule, a user (e.g., the patient) may select to approve the adjusted schedule and the process 1000 may schedule the treatment at the accepted time, at block 1010. Once the treatment is scheduled, time may be further scheduled to either or both clamp-off the patient, at block 1018, and clean any workstation, at block 1020.

At block 1022, the process 1000 may determine whether the treatment station is or will be vacant for a time at or after a predetermined time span (e.g., 15 minutes, 30 minutes, 45 minutes, 1 hour, 1.5 hours, 2 hours, 4 hours, etc.). If the station will not be vacant for a time at or above the predetermined time span, the process 1000 may again check vacancy until the treatment station is to be vacant for a time at or above the predetermine time span. If the station will be vacant for the predetermined time span or more than the predetermined time span, the process 1000 may end the session, at block 1024.

Figure 11:
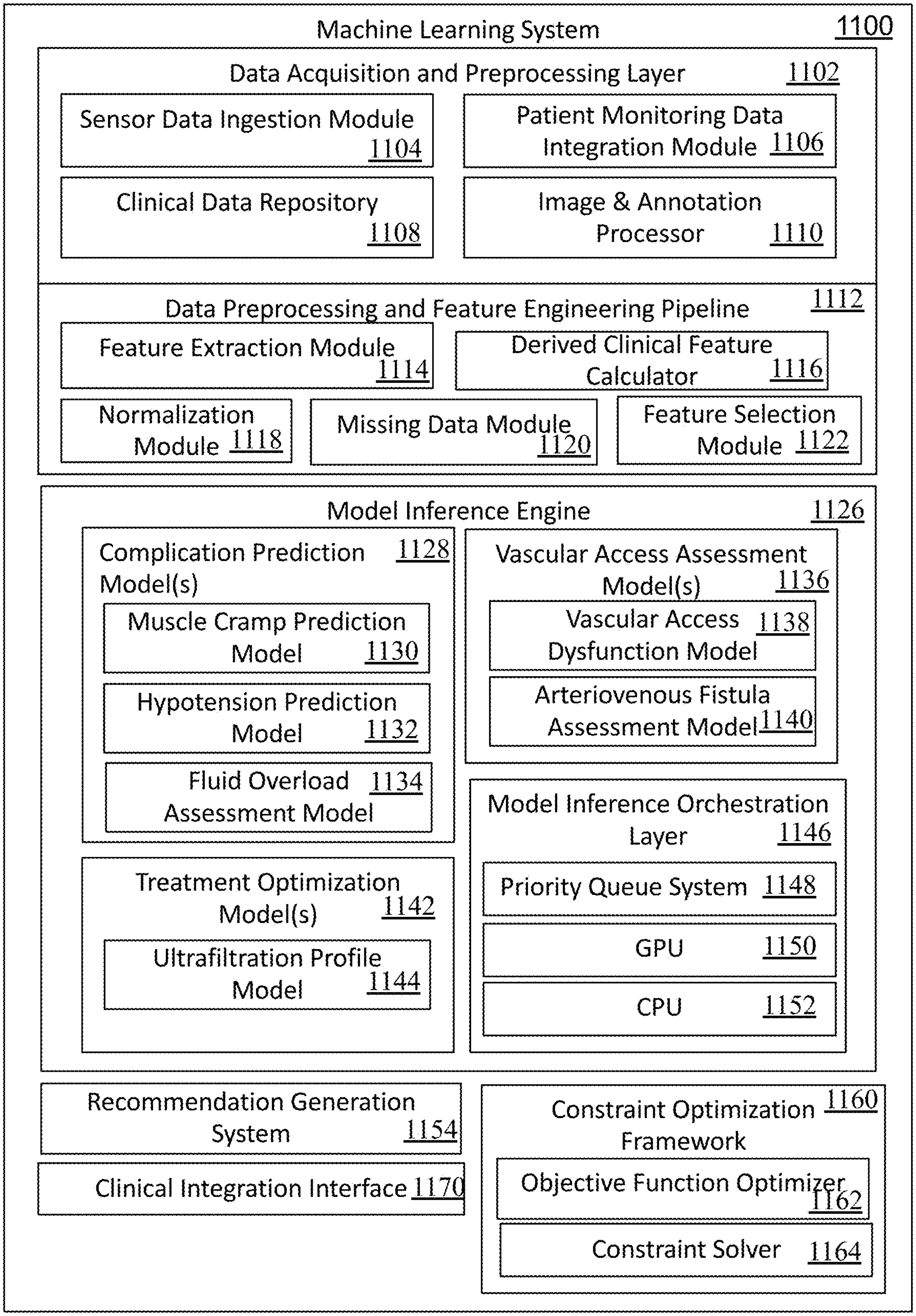
FIG. 11 is an example machine learning system for analyzing dialysis treatment and scheduling associated with dialysis treatment.

FIG. 11 illustrates an example machine learning system 1100 for analyzing dialysis treatment and scheduling associated with dialysis treatment. The machine learning system 1100 may include a multi-tier architecture for providing real-time treatment optimization, complication prediction, and clinical decision support during dialysis sessions. ML models may refer to any number of models including, but not limited to ML models 150. In some embodiments, the machine learning system 1100 may include a data acquisition and preprocessing layer 1102, a model inference engine 1126, a recommendation generation system 1154, a continuous learning pipeline 1172, and a clinical integration interface 1184, each of which may be communicatively coupled to enable bidirectional data flow and coordinated operation during dialysis treatment sessions.

The data acquisition and preprocessing layer 1102 may interface with multiple data sources to collect one or more input streams for machine learning models (e.g., ML models 150). In some embodiments, the data acquisition and preprocessing layer 1102 includes a sensor data ingestion module 1104, a patient monitoring data integration module 1106, a clinical data repository 1108, and an image and annotation processor 1110. Each of these modules may collect, normalize, and preprocess specific types of data relevant to dialysis treatment optimization and complication prediction.

The sensor data ingestion module 1104 may be communicatively coupled to the dialysis machine to receive real-time measurements from a sensor at configurable sampling rates. For example, the sensor data ingestion module 1104 may receive measurements on demand and/or every about 30 seconds to about 30 minutes; 30 seconds to about 2 minutes; 2 minutes to about 5 minutes; 5 minutes to about 10 minutes, 10 minutes to about 15 minutes; 15 minutes to about 20 minutes; 20 minutes to about 25 minutes; or 25 minutes to about 30 minutes. The measurements may include one or more of: blood flow rate, arterial pressure, venous pressure, ultrafiltration rate, cumulative volume removed, dialysate temperature, dialysate conductivity, and transmembrane pressure measured in mmHg. In some embodiments, the sensor data ingestion module 1104 may also or instead capture image data (e.g., from a handheld device or computing device), tactile data (e.g., from a handheld tactile glove, etc.), and/or other sensor-based data according to the above recited schedule. The sensor data ingestion module 1104 may timestamp each measurement and tag the measurement with a patient identifier, a session identifier, and a machine identifier to enable subsequent data organization and retrieval.

The patient monitoring data integration module 1106 may obtain physiological parameters from patient monitoring devices including blood pressure monitors, pulse oximeters, and/or optional wearable devices 132. In some embodiments, the patient monitoring data integration module 1106 receives systolic blood pressure, diastolic blood pressure, mean arterial pressure, oxygen saturation, heart rate, body temperature, activity levels, and bioimpedance measurements from one or more sensor and/or monitoring devices. The patient monitoring data integration module 1106 may synchronize data streams from disparate devices using a common time reference and may interpolate missing values using forward-fill, backward-fill, or linear interpolation methods depending on the parameter type and missing data pattern.

The clinical data repository 1108 may connect to the electronic medical record system 120 and patient profile database 126 to retrieve patient features. In some embodiments, the clinical data repository 1108 retrieves static and semi-static patient features including age, sex, weight, height, body mass index, primary kidney disease etiology, comorbidities (such as diabetes, cardiovascular disease, hypertension, and peripheral vascular disease), dialysis vintage representing time since dialysis initiation, vascular access type (fistula, graft, or catheter), prescribed dry weight, and current medications. The clinical data repository 1108 may cache frequently accessed data locally in memory to reduce latency while maintaining synchronization with source systems through periodic updates or event-driven triggers when clinical data changes.

The image and annotation processor 1110 may receive high-resolution images from the handheld imaging device or computing device and may process the images through a preprocessing pipeline. For ultrasound images of arteriovenous fistulas, for example, the image and annotation processor 1110 may perform noise reduction using Gaussian filtering, contrast enhancement using histogram equalization, Contrast Limited Adaptive Histogram Equalization (CLAHE), and/or region-of-interest extraction using edge detection algorithms. For photographic images of diabetic foot ulcers, the image and annotation processor 1110 may perform color normalization, perspective correction, and/or segmentation of a target area from surrounding tissue. Clinical annotations provided by healthcare providers during telemedicine sessions may be parsed, structured, and linked to corresponding images and patient session data by the image and annotation processor 1110.

The data acquisition and preprocessing layer 1102 further includes a data preprocessing and feature engineering pipeline 1112 to transform raw data streams into features suitable for machine learning model input. The data preprocessing and feature engineering pipeline 1112 includes a feature extraction module 1114, a derived clinical features calculator 1116, a normalization module 1118, a missing data module 1120, and a feature selection module 1122.

The feature extraction module 1114 may create time-based features from the raw parameter data. In some embodiments, the feature extraction module 1114 generates features including time since dialysis session start, time remaining in session, rate of change of parameters (such as blood pressure slope and ultrafiltration rate changes), moving averages over multiple time windows (e.g., 5 minute, 15 minute, and 30 minute windows), and temporal patterns indicating whether parameters are increasing, decreasing, stable, or oscillating.

The derived clinical features calculator 1116 may compute parameters that are not directly measured but are derived from combinations of measured parameters. In some embodiments, the derived clinical features calculator 1116 calculates blood volume change percentage derived from hematocrit changes, relative blood volume trajectory, cardiac output estimation based on blood pressure and heart rate, systemic vascular resistance, ultrafiltration coefficient, and dialysis adequacy metrics. These derived features may provide additional predictive information beyond the raw measured parameters.

The normalization module 1118 may apply patient-specific normalization by calculating deviations from patient baseline values using z-score normalization and may apply population-level scaling using min-max scaling or standardization to ensure features are on comparable scales for model input. For example, a current blood pressure of 128 mmHg for a patient with a baseline of 145 mmHg may be represented by the normalization and scaling module 1118 as −1.2 standard deviations from the patient's personal baseline while also being scaled to a zero to one range relative to a population distribution.

The missing data module 1120 may employ multiple imputation strategies based on data type and missingness pattern. For continuously monitored parameters with occasional missing values, the missing data module 1120 may use linear interpolation or forward-fill. For intermittently measured parameters such as laboratory values, the missing data module 1120 may use k-nearest neighbors imputation that finds similar patients and uses values associated with the similar patients, or multiple imputation to create multiple plausible values for use in ensemble predictions.

The feature selection module 1122 may apply feature selection algorithms to identify predictive features for each specific model task. In some embodiments, the feature selection and dimensionality reduction module 1122 employs recursive feature elimination to identify top predictive features. For example, for a muscle cramp prediction model, the feature selection and dimensionality reduction module 1122 may identify that ultrafiltration rate, blood pressure slope, sodium concentration, and treatment time are top predictive features, while dialysate flow rate and temperature contribute minimally. The feature selection module 1122 may also apply principal component analysis or autoencoder techniques to reduce high-dimensional data into lower-dimensional representations while preserving captured data.

The preprocessed and engineered features may be formatted into standardized data structures by the pipeline 1112 and stored in memory. In some embodiments, the memory may include a buffer such as a Redis cache or Apache Kafka message queue that provides immediate access to processed features for the model inference engine 1126. The model inference engine 1126 may host multiple machine learning models, each optimized for prediction or classification tasks related to dialysis treatment. The model inference engine 1126 may include complication prediction models 1128, vascular access assessment models 1136, and treatment optimization models 1142. In some embodiments, the model inference engine 1126 is implemented as a microservices architecture where each model runs in an isolated container with defined resource allocations including CPU cores, memory allocation, and GPU access based on computational requirements.

The complication prediction models 1128 may include multiple models to predict different types of patient complications during dialysis. In some embodiments, the complication prediction models 1128 include a muscle cramp prediction model 1130, a hypotension prediction model 1132, and/or a fluid overload assessment model 1134. The muscle cramp prediction model 1130 may include a bidirectional Long Short-Term Memory (LSTM) neural network for predicting the likelihood of muscle cramping during a dialysis session. In some embodiments, the muscle cramp prediction model 1130 includes an input layer for receiving one or more features including, but not limited to, dialysis parameters, vital signs, laboratory values, and temporal features; an embedding layer including a dense layer having ReLU activation; a first LSTM layer including at least 128 units configured bidirectionally to provide 256 total units with 0.3 dropout; a second LSTM layer including at least 64 units configured bidirectionally to provide 128 total units with 0.3 dropout; an attention mechanism including a self-attention layer with a plurality of attention heads configured to identify time points in the temporal sequence; a dense layer having ReLU activation and 0.4 dropout; and an output layer including at least 3 units with an activation configured to output probabilities for three outcomes such as no cramps, minor cramps, and severe cramps.

In some embodiments, the muscle cramp prediction model 1130 is trained on a dataset of tens of thousands of dialysis sessions from thousands of patients with cramp occurrence documented by clinical staff. The training process may use categorical cross-entropy loss, optimizer with learning rate of about 0.001, a batch size of about 64, and early stopping based on validation set performance. The muscle cramp prediction model 1130 may be set to achieve a predetermined level of accuracy (e.g., about 60 percent to about 80 percent accuracy, about 60 percent to about 75 percent precision, and about 65 percent to about 75 percent recall.

The hypotension prediction model 1132 may include an XGBoost ensemble to predict intradialytic hypotension. In some embodiments, the hypotension prediction model 1132 includes a plurality of decision trees (e.g., 100-200 trees) with a maximum depth of 6. In some embodiments, the model may have a learning rate of 0.1, subsample ratio of 0.8, column subsample ratio of 0.8, minimum child weight of 3, and gamma value of 0.1. The hypotension prediction model 1132 may be trained on tens of thousands of dialysis sessions with hypotension events labeled, where hypotension is defined as a systolic blood pressure drop of 20 mmHg or more, or an absolute systolic blood pressure below 90 mmHg. In some embodiments, the hypotension prediction model 1132 achieves about 72 percent to about 82 percent accuracy, about 70 precent to about 80 percent precision, about 70 percent to about 77 percent recall, 0.77 F1-score, and 0.88 AUC-ROC on validation data.

The fluid overload assessment model 1134 may employ a hybrid convolutional neural network (CNN) and multilayer perceptron (MLP) architecture. The fluid overload assessment model 1134 may include a CNN branch to process time-series data and an MLP branch configured to process static patient features. The CNN branch may include an input layer for receiving, for example, 48 time points by 12 parameters reshaped as a two-dimensional image; a first convolutional layer including, for example, 32 filters with a 3×3 kernel and ReLU activation; a first max pooling layer with 2×2 pooling; a second convolutional layer including 64 filters with a 3×3 kernel and ReLU activation; a second max pooling layer with 2×2 pooling; a third convolutional layer including 128 filters with a 3×3 kernel and ReLU activation; and a flatten layer to output a 128-dimensional feature vector.

The MLP branch of the fluid overload assessment model 1134 may include an input layer to receive a plurality of clinical features; a first dense layer including 256 units with ReLU activation and 0.3 dropout; a second dense layer including 128 units with ReLU activation and 0.3 dropout; and a third dense layer including 64 units with ReLU activation. In some embodiments, the CNN branch output and the MLP branch output may be concatenated to form a 192-dimensional combined vector. The combined vector may be processed through additional layers including a dense layer with 128 units, ReLU activation, and 0.4 dropout; a dense layer with 64 units and ReLU activation; and an output layer with 1 unit and sigmoid activation configured to output a fluid overload severity score ranging from zero to one. In some embodiments, the fluid overload assessment model 1134 is trained on tens of thousands of sessions with fluid overload assessed by bioimpedance measurements and clinical evaluation, achieving a mean absolute error of 0.12 on the severity score and 85% classification accuracy when using a 0.7 threshold for severe overload.

The vascular access assessment models 1136 may include models to detect vascular access dysfunction and assess arteriovenous fistula maturation. The vascular access assessment models 1136 may include a vascular access dysfunction model 1138 and an arteriovenous fistula assessment model 1140. The vascular access dysfunction model 1138 may use an ensemble approach combining multiple algorithms to detect vascular access dysfunction. In some embodiments, the vascular access dysfunction model 1138 includes a random forest classifier with a plurality of trees (e.g., about 100 to about 150 trees) and maximum depth of 8, an isolation forest component for anomaly detection in pressure-flow relationships, and an autoencoder neural network for detecting unusual patterns in pressure waveforms. The vascular access dysfunction model 1138 may combine predictions from all three components using weighted averaging with weights of about 50 percent for the random forest, about 30 precent for the isolation forest, and about 20 precent for the autoencoder. The weights may be tuned to optimize sensitivity for early detection. In some embodiments, the vascular access dysfunction model 1138 is trained on tens of thousands of dialysis sessions with vascular access outcomes documented, including about 10 percent of cases of confirmed stenosis or thrombosis within 30 days of a flagged session. The vascular access dysfunction model 1138 may achieve about 80 precent to about 90 percent sensitivity, about 70 percent to about 80 percent specificity, and may identify access dysfunction an average of about 15 to about 18 days before clinical presentation of symptoms.

The arteriovenous fistula assessment model 1140 may use a gradient boosting classifier to process ultrasound-derived measurements including vessel diameter, flow velocity, and volume flow rate; dialysis machine parameters including arterial pressure, venous pressure, and blood flow rates; temporal features including time since fistula creation and trend in flow parameters; and clinical features including patient age, comorbidities, and fistula location. The arteriovenous fistula assessment model 1140 may output a maturation probability score and may achieve about 85 percent to about 95 percent accuracy in predicting successful fistula use compared to clinical assessment by vascular surgeons, with about 90 percent to about 94 percent sensitivity and about 85 percent to about 88 percent specificity.

The treatment optimization models 1142 may include models to optimize treatment parameters during dialysis sessions. In some embodiments, the treatment optimization models 1142 include an ultrafiltration profile optimization model 1144 to determine optimal ultrafiltration rates and profiles to achieve target fluid removal while minimizing patient complications. The ultrafiltration profile model 1144 may use reinforcement learning with a Deep Q-Network (DQN) architecture to optimize the ultrafiltration profile. The ultrafiltration profile model 1144 may include a state space of, for example, a vector including dialysis parameters, patient vital signs, and treatment progress; an action space including discrete actions representing combinations of ultrafiltration rate adjustments, dialysate modifications, and treatment time extensions; and a neural network comprising an input layer with state features, a first dense layer with 256 units and ReLU activation, a second dense layer with 256 units and ReLU activation, a third dense layer with 128 units and ReLU activation, and an output layer with 25 units configured to output Q-values for each possible action.

In some embodiments, the ultrafiltration profile model 1144 is trained using experience replay, for example, with a replay buffer of 100,000 state-action-reward-next state tuples collected from simulated and actual dialysis sessions. The reward function may combine multiple objectives including: +10 for completing target fluid removal, −20 for hypotension occurrence, −10 for cramping, −5 for nausea, +5 for patient comfort ratings above 7 out of 10, and −0.5 per minute of treatment extension beyond standard time. The ultrafiltration profile optimization model 1144 may learn optimal treatment strategies through 500,000 training iterations and may achieve a 23 percent reduction in complications and a 15 percent improvement in treatment completion compared to standard protocols.

The model inference engine 1126 further includes a model inference orchestration layer 1146 to manage model execution based on clinical context and computational priorities. The model inference orchestration layer 1146 includes a priority queue system 1148, a GPU acceleration module 1150, and a parallel CPU processing module 1152. The priority queue system 1148 may categorize model inference tasks into multiple priority levels. In some embodiments, high-priority models including the hypotension prediction model 1132 and the vascular access dysfunction model 1138 execute every about two to about five minutes with results available within about 500 milliseconds. Medium-priority models including the muscle cramp prediction model 1130 and the fluid overload assessment model 1134 may execute every about fifteen minutes to about thirty minutes with results available within about 2 seconds. Lower-priority or computationally intensive models including the ultrafiltration profile model 1144 may execute on demand, for example, when requested by clinicians or at session start and/or session end. The priority queue system 1148 may enable urgent predictions triggered by sudden vital sign deterioration to preempt scheduled inference tasks.

The GPU acceleration module 1150 may provide graphics processing unit acceleration for neural network models including the muscle cramp prediction model 1130 and the fluid overload assessment model 1134. The parallel CPU processing module 1152 may provide parallel central processing unit processing for tree-based models including the hypotension prediction model 1132 and the vascular access dysfunction detection model 1138. The combination of the GPU acceleration module 1150 and the parallel CPU processing module 1152 may maximize inference throughput across the heterogeneous model ensemble.

The machine learning system further includes a recommendation generation system 1154. The recommendation generation system 1154 may translate model predictions from the model inference engine 1126 into actionable clinical recommendations. The recommendation generation system 1154 may utilize a clinical decision support rule engine (not shown), a constraint optimization framework (not shown), and an explanation generation module (not shown).

The clinical decision support rule engine may encode clinical knowledge as if-then rules that map prediction outputs to specific interventions. The clinical decision support rule engine may access a rule library (not shown) including clinical decision support rules. In some embodiments, the rule library maintains a plurality of rules covering various clinical scenarios, where each rule is assigned a priority level selected from low, medium, high, and urgent, and a confidence score based on supporting clinical evidence and model performance. An example rule stored in the rule library may be structured as follows: IF muscle_cramp_probability exceeds 0.60 AND ultrafiltration_rate exceeds 900 mL/hr, THEN recommend: reduce ultrafiltration rate to a target of 700 mL/hr for a duration of 30 minutes, AND increase dialysate temperature to a target of 37.0° C., AND implement sodium modeling with a profile of gradual increase, wherein the rule has PRIORITY: HIGH and CONFIDENCE: 0.85. Another example rule may be: IF hypotension_risk exceeds 0.75 AND blood_volume_change is less than −12%, THEN recommend: activate blood volume control with a threshold of 15%, AND reduce ultrafiltration rate to a target of 650 mL/hr, AND prepare saline bolus with a volume of 100 mL and a trigger of systolic blood pressure below 110 mmHg, wherein the rule has PRIORITY: URGENT and CONFIDENCE: 0.92.

The machine learning system 1100 further includes a constraint optimization framework 1160 that may optimize treatment parameters when multiple recommendations are generated. The constraint optimization framework 1160 includes an objective function optimizer 1162 and a constraint solver 1164. The objective function optimizer 1162 may maximize a treatment efficacy score while minimizing weighted factors including complication risk, treatment time extension, and patient discomfort. The constraint solver 1164 may apply multiple constraints including: total fluid removal greater than or equal to 0.90 times target volume to achieve at least 90 percent of prescribed removal; average ultrafiltration rate less than or equal to maximum patient tolerance; treatment time less than or equal to standard time plus 60 minutes to limit treatment extensions; blood flow rate within machine specifications of 200-500 mL/min; dialysate temperature within a safety range of about 35.0-37.5° C.; and total sodium load change within limits of plus or minus 15 mEq.

In some embodiments, the constraint solver 1164 may use mixed-integer linear programming to generate an optimal treatment parameter set that best satisfies competing objectives and constraints. For complex scenarios with multiple high-risk predictions, the constraint solver 1164 may generate alternative recommendation options with different risk-benefit tradeoffs for clinician review.

In some embodiments, the machine learning system 1100 may include a clinical integration interface 1170. The clinical integration interface 1170 may manage interactions between the machine learning system 1100 and clinical users including patients, dialysis technicians, nurses, and physicians. The clinical integration interface 1170 may include a real-time alert and notification system (not shown), a clinician dashboard and visualization module (not shown), a telemedicine integration interface (not shown), and a patient-facing interface (not shown). The real-time alert and notification system may monitor model outputs from the model inference engine 1126 and trigger alerts based on configurable thresholds. In some embodiments, the real-time alert and notification system implements multiple alert levels. Level 1 alerts for low-risk predictions and routine recommendations may be displayed on the dialysis machine interface, such as displaying "Mild cramping risk detected (28%). Current parameters acceptable." Level 2 alerts for moderate-risk predictions requiring attention may be displayed prominently with audible notification and technician acknowledgment required, such as "Hypotension risk elevated (62%). Consider reducing ultrafiltration rate. Review recommendation details." Level 3 alerts for high-risk predictions recommending or indicating intervention may trigger an urgent alert with distinct audible alarm, automatic page to supervising clinician, and a recommendation displayed with one-click implementation option, such as "HIGH RISK: Severe hypotension predicted (84%). RECOMMENDED ACTION: Reduce UF rate to 650 mL/hr immediately. [IMPLEMENT] [OVERRIDE] [REVIEW]." Level 4 alerts for immediate safety concerns may trigger an emergency alert with continuous alarm, automatic notification to physician, and may trigger automatic safety interventions such as reducing ultrafiltration or calling for assistance, such as "CRITICAL: Vascular access dysfunction detected. Venous pressure 220 mmHg (threshold 180). Treatment paused. Physician notified."

The clinician dashboard and visualization module may provide a comprehensive dashboard accessible through the dialysis machine touchscreen, desktop workstations, and mobile devices. In some embodiments, the clinician dashboard and visualization module provides multiple views including: a session monitoring view displaying real-time parameters, vital signs, and machine learning model predictions in a synchronized timeline view with color-coded risk indicators, including trend graphs showing parameter evolution over session duration and predictions for the next 30-60 minutes; a recommendation management panel listing all active recommendations with priority ranking, expected outcomes, implementation buttons, and options to defer or modify recommendations with required justification documentation; a patient profile insights view aggregating historical machine learning predictions and outcomes for the patient, showing patterns in complication risks, optimal treatment parameters, and treatment efficacy metrics, including longitudinal graphs of key parameters across multiple sessions; and a population analytics dashboard for clinic managers and medical directors providing aggregate metrics on machine learning system performance, complication rates, treatment efficiency, and identification of high-risk patient cohorts requiring enhanced monitoring.

The telemedicine integration interface may provide remote clinicians with access to machine learning system outputs during concurrent telemedicine sessions. In some embodiments, the telemedicine integration interface provides: a real-time data stream comprising a continuous feed of current dialysis parameters, vital signs, and laboratory values with 2-5 second latency; a machine learning insights panel summarizing relevant model predictions for the current session such as fluid overload assessment, vascular access status, and predicted complications; image viewing and annotation tools providing high-resolution image display with zoom, contrast adjustment, measurement tools, and annotation capabilities synchronized between patient-side and clinician-side displays; a treatment modification interface providing a secure interface allowing authorized specialists to review and approve machine learning-generated treatment recommendations or propose alternative modifications, with changes transmitted back to the dialysis machine for implementation; and bidirectional communication providing video conferencing, text chat, and screen sharing capabilities to facilitate discussion between remote clinician and bedside staff.

The patient-facing interface may enable patients to interact with the machine learning system 1100 through a simplified interface. In some embodiments, the patient-facing interface displays treatment progress showing session time remaining, fluid removal progress, and overall treatment status using easy-to-understand graphics such as progress bars and visual metaphors; provides comfort coaching with machine learning-driven suggestions for positioning, breathing exercises, or relaxation techniques when discomfort is predicted or reported; collects patient feedback using periodic prompts asking patients to rate comfort level, report symptoms, or respond to brief questionnaires, wherein responses are immediately incorporated into machine learning model inputs to refine predictions; delivers educational content providing personalized educational messages about dialysis, diet, medication adherence, and complication prevention based on the patient's risk profile and machine learning-identified knowledge gaps; and displays appointment and scheduling information showing upcoming dialysis appointments, concurrent specialist appointments, and reminders as coordinated by the integrated scheduling system 102 (FIG. 1B).

In some embodiments, the machine learning system 1100 may be deployed on a distributed computing infrastructure having multiple layers. The infrastructure may include an edge computing layer, a local server layer, and a cloud computing layer interconnected by a network architecture (e.g., network 1210 of FIG. 12). The edge computing layer may include an embedded computing module integrated with each dialysis machine, for example. In some embodiments, the embedded computing module may execute lightweight versions of frequently-used machine learning models including the hypotension prediction model 1132 and the vascular access dysfunction detection model 1138 for ultra-low latency inference in less than 100 milliseconds without network dependency. The local server layer may include a clinic server 1200 operated at each dialysis clinic. The clinic server 1200 may host the complete model inference engine 1126, process data from 20-30 dialysis machines simultaneously, and maintain local data storage of patient sessions with automated anonymization and encryption.

Figure 12:
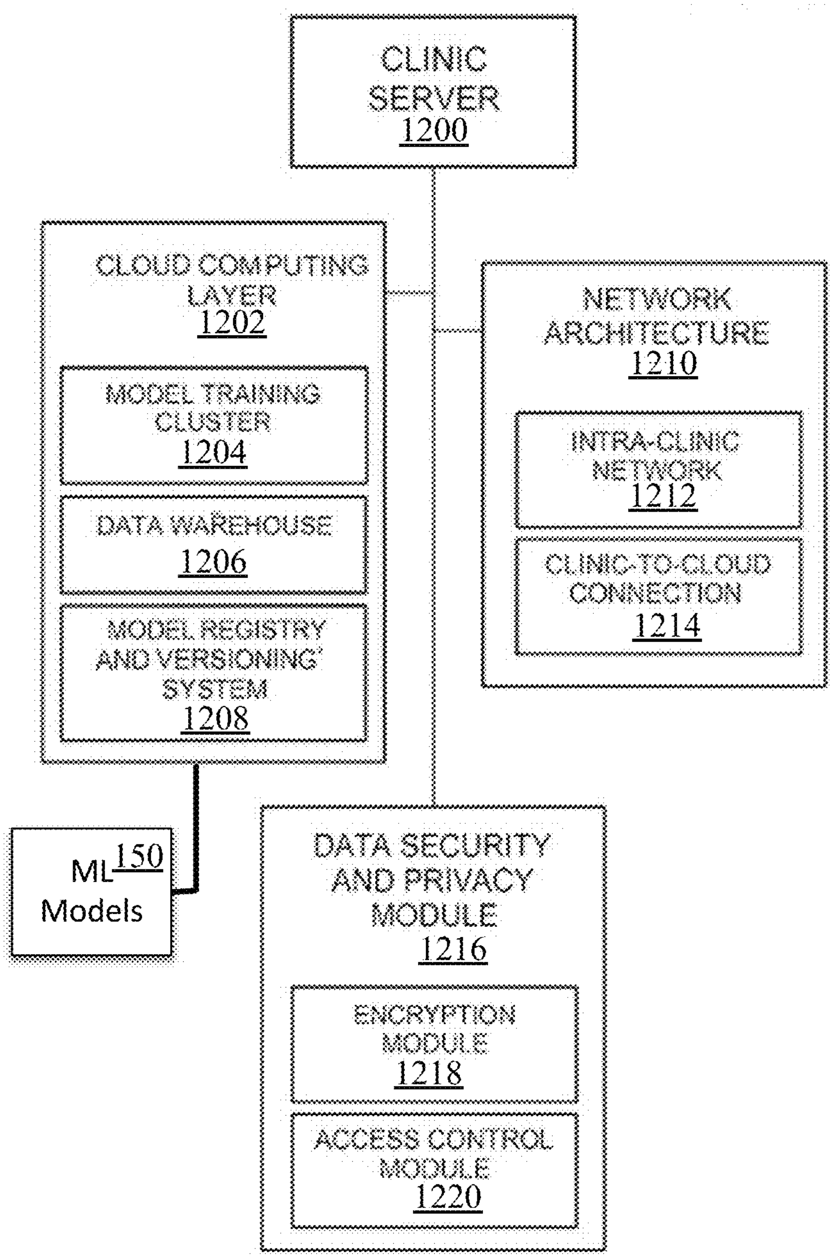
FIG. 12 is a block diagram of an example data architecture for at least one dialysis clinic.

FIG. 12 illustrates a block diagram of an example data architecture for at least one dialysis clinic server 1200. As shown, a cloud computing layer 1202 provides centralized cloud infrastructure using one or more cloud services. The cloud computing layer 1202 may include a model training cluster 1204, a data warehouse 1206, and a model registry and versioning system 1208. The model training cluster 1204 may include multiple GPU instances such as NVIDIA V100 or A100 GPUs, or the like, which may execute the training and/or of models. The data warehouse 1206 may store aggregated multi-site data about previously performed dialysis sessions and provide analytics and reporting services associated with such sessions. The model registry and versioning system 1208 may maintain version control for machine learning models 150, for example, and enable model deployment and rollback capabilities.

The clinic server 1200 may be coupled to or in communication with a network architecture 1210 that may implement a cloud architecture or the like. As shown in FIG. 12, the network architecture 1210 includes an intra-clinic network 1212 and a clinic-to-cloud connection 1214. The intra-clinic network 1212 may couple dialysis machines to the clinic server 1200 to allow near real-time and/or real-time data streaming. The machine learning system 1100 may have access to a data security and privacy module 1216. The data security and privacy module 1216 may implement HIPAA-compliant security measures. The data security and privacy module 1216 includes an encryption module 1218, an access control module 1220, and an optional audit logging module (not shown). The encryption module 1218 may implement encryption to protect patient health information. The access control module 1220 may implement role-based access control (RBAC) with multi-factor authentication to ensure authorized personnel can access patient data and system functions. The audit logging module may maintain comprehensive logging of all data access events, model predictions, and user actions to provide an audit trail for compliance and security monitoring.

In some embodiments, the data security and privacy module 1216 further implements automated de-identification of data used for model training in which protected health information is accessible to authorized clinical personnel. The data security and privacy module 1216 may also implement automated data retention policies, patient consent management, and right-to-be-forgotten compliance in accordance with healthcare privacy regulations.

The model registry and versioning system 1208 may maintain multiple model versions. In some embodiments, production models are tagged with version numbers associated with the model utilized and each respective prediction may be logged by the machine learning system 1100 and may include the model version for traceability. If a new model shows degraded performance, the model registry and versioning system 1208 may perform automatic rollback to a previous stable version within a predefined time period (e.g., within about 1 hour). The model registry and versioning system 1208 may generate model performance comparison reports for clinical review before full deployment of new model versions.

The ML models 150 may include neural network architectures designed for multi-modal healthcare prediction in the dialysis treatment environment of system 1100 and system 1200. In some embodiments, the model utilizes a deep learning framework with multiple interconnected layers to process heterogeneous data inputs including numerical dialysis parameters, temporal sequence data, and clinical annotations from healthcare providers. The model architecture may include one or more convolutional neural networks for processing time-series dialysis data, recurrent neural networks for analyzing sequential treatment patterns, and fully connected layers for generating final predictions and recommendations.

Training data for the machine learning models 150 may be collected from a plurality of dialysis sessions across multiple patients and dialysis centers. The training dataset may include dialysis parameters including, but not limited to, blood pressure measurements, heart rate, oxygen saturation, ultrafiltration rates, blood flow rates, venous pressure, arterial pressure, and hematocrit levels collected at predetermined intervals during dialysis sessions. Patient outcome data may include documented complications such as muscle cramps, hypotension, nausea, fatigue, itchy skin, fluid overload, and electrolyte imbalances, along with their temporal relationship to specific dialysis parameter patterns. Vascular access performance data includes machine pressure readings, blood flow measurements, access flow rates, and clinical assessments of arteriovenous fistula maturation and functionality. Any or all datasets described herein may be anonymized if used for predictions, assessments, and/or decisions between and amongst more than one patient.

In some embodiments, the machine learning models 150 may process real-time inputs from multiple sources within the dialysis machine system. In some embodiments, machine pressure sensors and flow meters may continuously provide vascular access performance data, which may be normalized and provided to an input layer of one or more models at predetermined intervals, such as every 30 seconds to 5 minutes. Hematocrit detection devices may provide fluid status measurements that are processed alongside ultrafiltration rate data to assess patient fluid balance in real-time. Clinical observations and annotations entered by healthcare providers during concurrent telemedicine sessions may be converted to structured data formats and integrated with the quantitative sensor data.

The ML models 150 may apply feature extraction algorithms to identify relevant patterns within the input data streams. For vascular access assessment, the models 150 may analyze pressure waveform characteristics, flow rate variability, and/or pressure-flow relationships to detect indicators of access dysfunction. For dialysis profile optimization, the models 150 may examine fluid removal patterns, patient vital sign responses, and historical complication data to identify treatment parameters that may lead to patient discomfort or adverse events.

In some embodiments, the ML models 150 may generate multiple types of predictive outputs tailored to specific clinical decision-making needs. For arteriovenous fistula maturation assessment, for example, the ML model 150 may output a probability score ranging from zero to one, where values above a predetermined threshold (e.g., about 0.7 to about 0.8) indicate sufficient fistula development for clinical use. This assessment may be tunable to consider factors including one or more of: measured blood flow rates, pressure differentials, vessel diameter measurements from ultrasound imaging, and time since fistula creation surgery.

Vascular access dysfunction risk assessment may be generated as both a categorical classification (e.g., low, moderate, high risk) and a continuous risk score. The model 150 may identify early indicators of access problems such as gradually increasing venous pressures, decreasing blood flow rates, and/or abnormal pressure-flow relationships that may precede complete access failure. When the risk score exceeds predetermined thresholds, the system may automatically generate alerts and scheduling recommendations for vascular surgery consultations.

In some embodiments, the system 1100 may generate personalized ultrafiltration profile recommendations by analyzing the patient's historical response to different fluid removal patterns. The ML model 150 may select from a library of available treatment profiles, which may include a number of different ultrafiltration patterns with varying rates of fluid removal over time. The recommendation system 1154 may consider patient-specific factors such as cardiovascular status, previous cramping episodes, blood pressure responses, and/or treatment tolerance to optimize both clinical effectiveness and patient comfort.

In some embodiments, the ML model 150 incorporates a continuous learning mechanism that updates model parameters based on treatment outcomes and healthcare provider feedback. After each dialysis session, patient outcome data including any complications, comfort levels, and treatment effectiveness measures are fed back into the model as labeled training examples. Healthcare provider corrections or modifications to model recommendations are captured and used to refine prediction algorithms through online learning techniques. Model performance may be continuously monitored through validation metrics including prediction accuracy, false positive rates for complication prediction, and clinical outcome improvements. The system 1100 maintains separate model versions for different patient populations (e.g., diabetic patients, cardiovascular disease patients, elderly patients) to account for population-specific treatment responses and risk factors. Model updates may be deployed after validation testing confirms improved performance without degradation of existing capabilities.

In some embodiments, the ML model 150 may generate predictive outputs that are integrated with the dialysis machine's clinical decision support system to provide automated recommendations and alerts. For example, when fistula dysfunction probability exceeds about 0.7, the system automatically communicates with vascular surgery scheduling systems to propose appointment times that align with the patient's dialysis schedule. Predicted patient complications trigger immediate alerts to clinical staff and may result in automatic adjustment of dialysis parameters such as ultrafiltration rate reduction or treatment time extension. The clinical decision support system maintains a knowledge base of evidence-based treatment protocols that are combined with machine learning predictions to generate comprehensive care recommendations. For example, when the ML model 150 predicts high cramping risk based on rapid fluid removal patterns, the system may recommend switching to a more gradual ultrafiltration profile while simultaneously scheduling concurrent appointments with nephrology and cardiology providers to address underlying cardiovascular factors contributing to fluid retention.

In some embodiments, the received assessments, diagnoses, or recommendations described herein may be generated by one or more ML model 150 and an input provided by the at least one healthcare provider. The model may analyze a plurality of dialysis parameters associated with the patient and predict, based on the plurality of dialysis parameters, patient complications. The patient complications may include one or more of muscle cramps, low blood pressure, and fluid overload. In some embodiments, the model may automatically generate a recommendation for adjusting dialysis machine parameters including ultrafiltration profiles to preemptively prevent the predicted complications. In addition, the model may generate a customized treatment profile according to the adjusted dialysis machine parameters and store the customized treatment profile in a patient record for future reference and continuous optimization of treatment.

In some embodiments, the ML model 150 may include a recurrent neural network (RNN) with long short-term memory (LSTM) architecture specifically trained to predict the onset of muscle cramps during dialysis sessions. The model may receive as input a plurality of dialysis parameters collected at 5-minute intervals throughout the dialysis session, including: ultrafiltration rate (mL/hr), cumulative fluid removed (liters), blood flow rate (mL/min), dialysate temperature (° C.), patient blood pressure (systolic/diastolic mmHg), heart rate (beats per minute), blood sodium concentration (mEq/L), blood potassium concentration (mEq/L), and hematocrit percentage. In a non-limiting example for a Patient B, who is undergoing a 4-hour dialysis session with a prescribed total fluid removal of 3.2 liters, the model continuously analyzes the incoming parameter stream. In this example, at the 90-minute mark of the session, the model has received the following sequence of measurements: ultrafiltration rates progressing from 800 mL/hr initially to 950 mL/hr currently; cumulative fluid removed of 1.4 liters; blood flow rate steady at 400 mL/min; dialysate temperature at 36.5° C.; systolic blood pressure declining from 145 mmHg to 128 mmHg; heart rate increasing from 72 to 84 beats per minute; sodium concentration decreasing from 140 mEq/L to 137 mEq/L; and hematocrit increasing from 32% to 35% due to fluid removal. The LSTM layers of the neural network process these temporal sequences and identify patterns that historically correlate with muscle cramp occurrence. In this example, the model recognizes that the combination of: (1) ultrafiltration rate exceeding 900 mL/hr, (2) systolic blood pressure drop of more than 15 mmHg from baseline, (3) heart rate increase exceeding 10 beats per minute, and (4) sodium concentration decline of 3 mEq/L or more, creates a risk profile associated with muscle cramps. The model's hidden layers, comprising 128 LSTM units in the first layer and 64 units in the second layer, extract temporal features from the sequential data and feed them into a fully connected output layer with softmax activation, for example, which generates probability distributions for three outcomes: no complications (35% probability), minor cramping (48% probability), and severe cramping (17% probability). Based on the analysis, the machine learning model outputs a muscle cramp risk score of 0.65 on a scale of 0 to 1, indicating a 65% probability that Patient B will experience muscle cramping within the next 30-45 minutes if current treatment parameters are maintained. The model also generates an attention map highlighting that the rapid ultrafiltration rate (contributing 38% to the risk score) and the declining blood pressure (contributing 29% to the risk score) are the primary risk factors, while the sodium concentration decline contributes 21% and the heart rate increase contributes 12% to the overall risk assessment.

In another non-limiting example for a patient C, the ML model 150 may utilize a gradient boosting decision tree ensemble such as an XGBoost architecture, trained on historical data from over 50,000 dialysis sessions across 2,500 patients to predict intradialytic hypotension (IDH), defined as a systolic blood pressure drop of 20 mmHg or more, or a decrease to below 90 mmHg systolic. The model may incorporate real-time dialysis parameters and patient-specific features including age, body mass index, presence of diabetes, cardiovascular disease history, baseline blood pressure, and medications (particularly antihypertensive agents).

In another non-limiting example for a patient D, a convolutional neural network (CNN) combined with a multilayer perceptron (MLP) may be employed to assess fluid overload status and predict post-dialysis fluid retention. The CNN component processes time-series dialysis parameter data formatted as 2D images (with time on one axis and parameter type on the other), while the MLP component integrates patient demographic and clinical features.

In yet another non-limiting example about Patient B with a muscle cramp prediction example described elsewhere herein, the ML model 150 may automatically generate specific recommendations to mitigate the 65% muscle cramp risk. The recommendation generation system 1154 (e.g., system 142) which may represent a rule-based system informed by model predictions and attention maps, determines that reducing the ultrafiltration rate is the highest priority intervention given its 38% contribution to the risk score. The model may generate parameter adjustments such as (1) reduce the current ultrafiltration rate from 950 mL/hr to 700 mL/hr for the next 30 minutes, representing a 26% reduction, (2) increase the dialysate temperature from 36.5° C. to 37.0° C., as the model has learned from training data that slightly warmer dialysate reduces muscle cramp incidence by improving peripheral circulation, (3) implement a sodium modeling profile that gradually increases dialysate sodium concentration over a time period to counteract the declining blood sodium level, and (4) after the time period of reduced ultrafiltration, gradually increase the rate for the remainder of the session to still achieve the target total fluid removal by extending the treatment time by a determine amount of time (e.g., minutes). The proposed recommendations may be provided to a clinician and/or dialysis technician. In some embodiments, the proposed recommendations may be set to automatically implement in an autonomous mode according to clinic protocols. Upon approval by the dialysis technician (or automatic implementation if operating in fully autonomous mode per clinic protocols), the customized treatment profile may be executed, and the dialysis machine parameters may be adjusted accordingly. The model continues to monitor Patient B's response to these adjustments, collecting real-time feedback data on blood pressure stability, heart rate, symptom reports, and actual occurrence or non-occurrence of muscle cramps. At the conclusion of the dialysis session, the system 1100 may record that Patient B completed the treatment without experiencing muscle cramps, achieved a particular target fluid removal, and maintained stable blood pressure throughout. This outcome data is fed back into the machine learning model as a positive training example, strengthening the model's learned association between the implemented parameter adjustments and favorable patient outcomes.

The customized treatment profile, along with the session outcome data, may be stored in Patient B's electronic health record with the following metadata: session date and time, initial risk assessment (e.g., 65% cramp risk), implemented interventions (e.g., reduced ultrafiltration rate, increased dialysate temperature, sodium modeling), predicted risk reduction (e.g., to 22%), actual outcome (e.g., no complications), and treatment effectiveness score (e.g., 9.2 out of 10 based on target achievement and complication avoidance). This profile may become part of Patient B's treatment history and is used to initialize the machine learning model's predictions for subsequent dialysis sessions.

In another non-limiting example using Patient C (from the hypotension prediction example described elsewhere herein), the ML model 150 may generate a comprehensive set of recommendations addressing the 78% hypotension risk. The model's recommendation system 1154 may propose a multi-modal intervention strategy such as (1) immediate reduction of ultrafiltration rate (2) activation of blood volume-controlled ultrafiltration feedback system that automatically modulates fluid removal rate based on real-time blood volume monitoring, with target parameters set to limit blood volume reduction to no more than 15% from baseline (3) Trendelenburg positioning to improve venous return, and (4) administration of 100 mL normal saline bolus if systolic blood pressure drops below about 110 mmHg despite ultrafiltration reduction. The model may generate an optimized ultrafiltration profile incorporating these intervention strategy. Over the course of subsequent dialysis sessions for Patient C, the model 150 may continuously refine the customized treatment profile based on accumulated outcome data. The continuous optimization process may incorporate Bayesian updating of model parameters, where each new session provides evidence that updates the model's posterior probability distributions for optimal treatment parameters specific to Patient C. The model maintains an uncertainty estimate for each parameter recommendation, which decreases as more session data accumulates, resulting in progressively more confident and precise treatment profiles tailored to the individual patient's physiological responses and risk factors.

Figure 13:
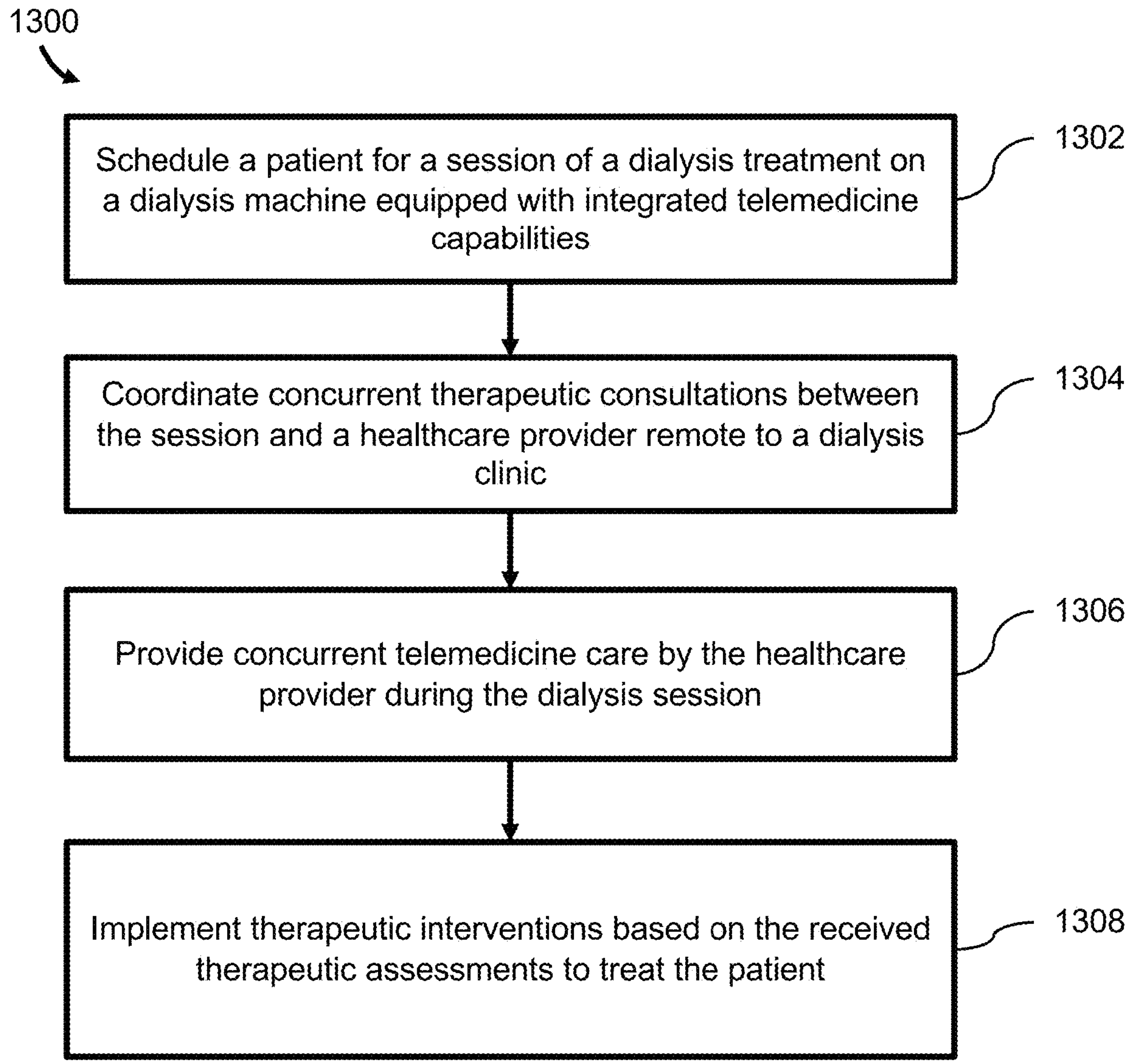
FIG. 13 is a flow diagram of an example method of treatment for use with the dialysis machines described herein.

FIG. 13 is a flow diagram of an example method of treatment process 1300 for use with the dialysis machines described herein. The process 1300 may be implemented in conjunction with the machine learning system 1100 described in FIG. 11 and may utilize components including the data acquisition and preprocessing layer 1102, model inference engine 1126, recommendation generation system 1154, and clinical integration interface 1170 to optimize treatment delivery during concurrent telemedicine consultations.

At block 1302, the process 1300 may include scheduling a patient for a session of a dialysis treatment on a dialysis machine equipped with integrated telemedicine capabilities. The operations of block 1302 may be performed by a scheduling system 102 as described with reference to FIGS. 1A-1B, which may interface with the machine learning system 1100 to incorporate predictive analytics into scheduling decisions.

In a non-limiting example, a patient with stage 5 chronic kidney disease, type 2 diabetes, and peripheral vascular disease may be scheduled for a dialysis treatment session on Tuesday from 9:00 AM to 1:00 PM on dialysis machine 4C equipped with integrated telemedicine infrastructure. The scheduling process may include the scheduling system 102 accessing the patient's historical treatment data stored in the clinical data repository 1108 of the machine learning system 1100, which contains records from previous dialysis sessions including treatment parameters, complication occurrences, and clinical outcomes. The data acquisition and preprocessing layer 1102 may retrieve this historical data and prepare it for analysis, including parameters such as the patient's typical ultrafiltration tolerance, historical blood pressure responses during treatment, documented episodes of intradialytic hypotension or muscle cramping, and interdialytic weight gain patterns. The scheduling system may also coordinate with the patient monitoring data integration module 1106 to incorporate recent data from the patient's wearable continuous glucose monitoring device, which shows glucose control trends relevant to the patient's diabetes management during dialysis sessions. Based on this comprehensive data analysis, the scheduling system may select Tuesday morning as an optimal treatment time, accounting for the historical patient preference for morning appointments, transportation availability through the patient's family member who works an evening shift, and clinic capacity to accommodate concurrent specialist consultations during that session.

At block 1304, the process 1300 may include coordinating concurrent therapeutic consultations between the session and a healthcare provider remote to a dialysis clinic housing the dialysis machine, where the coordinating includes automatically transmitting dialysis machine scheduling information to healthcare scheduling systems associated with the healthcare provider. The operations of block 1304 may be performed by the scheduling system 102 in coordination with the communication engine 114 and message generator 160 as described with reference to FIGS. 1A-1B. Continuing the above example, once the patient is scheduled for the Tuesday 9:00 AM to 1:00 PM dialysis session, the scheduling system may automatically transmit detailed session information to multiple healthcare scheduling systems associated with providers treating the patient. The transmitted information may include the confirmed dialysis session date and time, estimated patient arrival and treatment initiation time, dialysis machine identification and location within the clinic facility, integrated telemedicine equipment capabilities including camera specifications and handheld ultrasound device availability, and recommended time windows for concurrent consultations based on typical treatment stability phases. The machine learning system 1100 may contribute to this coordination by analyzing historical session data through the model inference engine 1126 to predict optimal consultation timing. For example, the hypotension prediction model 1132 may analyze the patient's blood pressure patterns and predict that the patient typically experiences a stable hemodynamic period during the second hour of treatment (between 10:00 AM and 11:00 AM for this session), making that time window suitable for specialist consultations that include patient engagement and assessment. Based on this analysis, the scheduling system may transmit availability information to the patient's vascular surgeon indicating that the optimal window for arteriovenous fistula assessment is between 10:15 AM and 10:45 AM, and to the patient's endocrinologist suggesting a diabetes management consultation between 11:00 AM and 11:30 AM. The healthcare scheduling systems may respond with confirmed appointment times: the vascular surgeon confirms availability for 10:15 AM consultation, and the endocrinologist confirms availability for 11:00 AM consultation. The ranking engine 148 within the scheduling system may prioritize the vascular consultation as higher urgency based on recent machine pressure readings from previous dialysis sessions showing gradual increases in venous pressure, which the vascular access dysfunction model 1138 has flagged as early indicators of potential access stenosis requiring evaluation.

At block 1306, the process 1300 may include providing concurrent telemedicine care by the healthcare provider during the dialysis session. The operations of block 1306 may involve multiple integrated sub-processes that work together to deliver comprehensive remote clinical care. These sub-processes may be supported by the clinical integration interface 1170 of the machine learning system 1100, which manages interactions between the machine learning models and clinical users.

For example, the process 1300 may include a sub-process of automatically establishing a telemedicine session between the patient and the healthcare provider at a predetermined time window within the dialysis session. When the patient arrives at 8:45 AM and dialysis treatment initiates at 9:00 AM, the system may begin monitoring session parameters through the sensor data ingestion module 1104 of the machine learning system 1100. The sensor data ingestion module 1104 may receive real-time measurements at regular intervals including blood flow rate through the dialysis circuit, arterial pressure, venous pressure, ultrafiltration rate, cumulative fluid volume removed, transmembrane pressure, dialysate conductivity, and dialysate temperature. Simultaneously or serially, the patient monitoring data integration module 1106 may collect physiological parameters from patient monitoring devices including blood pressure readings, heart rate, oxygen saturation, and body temperature. These data streams may be preprocessed by the data preprocessing and feature engineering pipeline 1112, which normalizes values, calculates derived parameters, and formats the data for model input. At 10:15 AM, the predetermined time for the vascular surgeon consultation, the telemedicine session initiation component may automatically establish the video connection between the patient at a dialysis station and the vascular surgeon at a remote medical office. The real-time alert and notification system within the clinical integration interface 1170 may send notifications to both the patient and the surgeon indicating that the consultation is beginning, while the clinician dashboard and visualization module displays relevant patient information on the surgeon's telemedicine workstation.

The process 1300 may further include a sub-process of enabling real-time clinical assessment through controlling at least one imaging device coupled to the dialysis machine to capture high resolution images of patient-specific conditions during the telemedicine session. During the vascular surgeon consultation at 10:15 AM, a dialysis technician may retrieve the handheld ultrasound imaging device from its docking station on the dialysis machine and position it over the patient's left forearm arteriovenous fistula. The video communication control component may adjust the integrated camera to provide the surgeon with a wide-angle view of the patient's arm positioning and the technician's ultrasound probe placement. The handheld ultrasound device may capture multiple high-resolution images showing the fistula anatomy, including longitudinal and transverse views of the arteriovenous anastomosis site, segments of the venous outflow tract, vessel diameter measurements at standardized locations, and color Doppler imaging showing blood flow patterns and velocity characteristics. The image and annotation processor 1110 within the machine learning system 1100 may receive these ultrasound images and perform preprocessing operations including noise reduction using Gaussian filtering, contrast enhancement using CLAHE algorithms, for example, and region-of-interest extraction to isolate the vascular structures from surrounding tissue. The processed images may be displayed simultaneously on the dialysis machine's video monitor for patient and bedside staff viewing, and transmitted to the surgeon's workstation for clinical evaluation. The vascular access assessment models 1136 within the model inference engine 1126 may analyze the captured images in parallel with the surgeon's visual assessment. Specifically, the vascular access dysfunction model 1138 may process the ultrasound-derived measurements along with current dialysis machine parameters to calculate a dysfunction probability score, while the arteriovenous fistula assessment model 1140 may evaluate maturation status based on vessel diameter, flow velocity, volume flow rate, and depth from skin surface measurements.

The process 1300 may further include a sub-process of transmitting the high resolution images to the healthcare provider for immediate clinical evaluation. The transmission process may occur in real-time as images are captured, with minimal latency between image acquisition and display on the surgeon's workstation. The image transmission system may utilize secure, encrypted communication protocols to protect patient health information during transmission over network connections. The transmitted images may maintain clinical-grade resolution sufficient for diagnostic interpretation, and may include embedded metadata such as measurement annotations, Doppler velocity calculations, and time-stamped capture information. During the consultation, the vascular surgeon may use the telemedicine integration interface to manipulate the transmitted images, adjusting brightness and contrast, zooming into regions of interest, and utilizing measurement tools to quantify vessel dimensions and flow characteristics. The surgeon may identify a region approximately two to three centimeters distal to the anastomosis site where the ultrasound imaging reveals turbulent flow patterns and vessel wall thickening suggestive of developing stenosis. Using the annotation interface provided through the real-time annotation display component, the surgeon may mark this region on the transmitted images and add text annotations describing the findings. These annotations may appear simultaneously on both the surgeon's workstation and the dialysis machine's video monitor, enabling shared understanding between the remote surgeon and the bedside dialysis staff.

The process 1300 may further include a sub-process of receiving therapeutic assessments from the healthcare provider based on the high resolution images, where the assessments comprise one or more of: a vascular access diagnosis with treatment recommendations, a fistula maturation assessment with management guidance, and a personalized dialysis profile recommendation. The operations of block 1308 may integrate clinical expertise from the healthcare provider with analytical outputs from the machine learning system 1100 to generate comprehensive therapeutic assessments. In the continuing example, based on the ultrasound images and clinical evaluation during the telemedicine consultation, the vascular surgeon may provide a vascular access diagnosis documenting that the arteriovenous fistula shows evidence of developing stenosis in the mid-venous outflow tract, with estimated luminal narrowing and elevated flow velocities indicating hemodynamically significant obstruction. The surgeon's diagnosis may correlate with the output from the vascular access dysfunction model 1138, which calculated a dysfunction probability score indicating elevated risk for access failure within the next thirty to sixty days if the stenosis progresses untreated. The surgeon may provide treatment recommendations including scheduling procedures within time periods to assess the patient further. The recommendations may include interim monitoring protocols, such as measuring dialysis machine venous pressures at each treatment session and documenting any changes in physical examination findings like diminished thrill intensity or altered bruit character. Additionally, the surgeon may provide guidance about continuing to use the fistula for dialysis access during the interim period before intervention, with instructions to adjust needle placement to avoid the stenotic region and recommendations for blood flow rate parameters that balance treatment adequacy with minimizing stress on the compromised access.

Following the vascular surgeon consultation, at 11:00 AM the endocrinologist consultation may begin as scheduled. During this second concurrent consultation, the endocrinologist may review glucose data transmitted from the patient's continuous glucose monitoring device, which the diagnostic data receiving component obtained and the patient monitoring data integration module 1106 incorporated into the patient's current session data. The endocrinologist may also review point-of-care hemoglobin A1c testing results obtained at the start of the dialysis session, which the blood sampling interface collected and the point-of-care diagnostic device analyzed. Based on this comprehensive diabetes data along with assessment of the patient's reported dietary adherence and hypoglycemia frequency, the endocrinologist may provide a personalized dialysis profile recommendation addressing the interaction between diabetes management and dialysis treatment. The recommendation may include adjusting the timing of insulin administration relative to dialysis sessions to minimize intradialytic hypoglycemia risk, modifying the dialysate glucose concentration to reduce glucose influx during treatment which can worsen hyperglycemia, coordinating nutrition counseling to address both diabetes dietary requirements and dialysis fluid and electrolyte restrictions, and implementing more frequent blood glucose monitoring during dialysis sessions when adjusting diabetes medications. The recommendation generation system 1154 within the machine learning system 1100 may support this personalized profile by analyzing the patient's glucose trends in relation to dialysis treatment timing through the fluid overload assessment model 1134, which incorporates metabolic parameters alongside volume status assessment.

At block 1308, the process 1300 may include implementing therapeutic interventions based on the received therapeutic assessments to treat the patient. The operations of block 1308 may include translating the healthcare providers'clinical recommendations into actionable treatment modifications that optimize patient outcomes. This implementation process may be supported by the treatment optimization models 1142 within the machine learning system 1100, which generate specific parameter recommendations based on clinical assessment findings.

In accordance with the method of treatment, implementing the therapeutic interventions may include automatically adjusting dialysis machine parameters to optimize treatment delivery according to the received therapeutic assessments. Based on the vascular surgeon's assessment of fistula stenosis and recommendations for interim management, the system may implement several parameter adjustments for the patient's subsequent dialysis treatments. The treatment optimization models 1142, specifically the ultrafiltration profile optimization model 1144, may generate recommendations for modifying blood flow rates through the compromised fistula access to balance adequate dialysis delivery with minimizing hemodynamic stress on the stenotic segment. The model may recommend reducing the target blood flow rate from the patient's previous standard parameter to a more conservative value, accepting slightly longer treatment times to achieve adequate dialysis dose while protecting the access from excessive flow-related stress that could accelerate stenosis progression. The constraint optimization framework 1160 may apply multiple constraints to ensure the adjusted parameters maintain treatment adequacy, including ensuring the dialysis adequacy metrics remain above the minimum threshold, limiting treatment time extension to acceptable durations, and maintaining ultrafiltration rates within the patient's tolerance range.

In addition, based on the endocrinologist's personalized dialysis profile recommendation addressing diabetes management during dialysis, the system may implement adjustments to dialysate composition and monitoring protocols. The dialysate glucose concentration may be adjusted to a lower value to minimize glucose influx from the dialysate into the patient's bloodstream during treatment, which the endocrinologist identified as contributing to post-dialysis hyperglycemia. The system may also configure automated blood glucose monitoring alerts, triggering notifications to dialysis staff if the patient's continuous glucose monitor reports values falling below or rising above specified thresholds during treatment, enabling timely intervention to prevent hypoglycemia or severe hyperglycemia episodes. These parameter adjustments may be calculated through the objective function optimizer 1162 within the constraint optimization framework 1160, which maximizes treatment efficacy while accounting for the competing considerations of vascular access preservation, glucose control optimization, and patient comfort maintenance.

The process 1300 may further include generating a customized treatment profile according to the adjusted dialysis machine parameters. The customized treatment profile may represent a comprehensive specification of treatment parameters tailored to the patient's specific clinical conditions and therapeutic needs. For this patient, the customized treatment profile may include target blood flow rate parameters adjusted for fistula stenosis management, ultrafiltration rate profile with gradual ramping to minimize hemodynamic instability given the patient's history of intradialytic hypotension predicted by the hypotension prediction model 1132, modified dialysate glucose concentration for diabetes management, automated monitoring alerts for blood glucose excursions during treatment, venous pressure monitoring thresholds set to detect worsening stenosis through progressive pressure increases, treatment time parameters that may be extended if needed to achieve adequate dialysis dose at the reduced blood flow rate, and scheduled reassessment timeline coordinating with the vascular intervention plan. The customized treatment profile generation may integrate recommendations from multiple machine learning models within the model inference engine 1126, including the muscle cramp prediction model 1130 which identified that this patient has elevated cramping risk during aggressive fluid removal, informing the ultrafiltration profile parameters, and the fluid overload assessment model 1134 which assessed the patient's volume status and appropriate fluid removal targets.

The process 1300 may include storing the customized treatment profile in a patient record. The customized treatment profile may be stored within the secure electronic medical record system associated with the patient, accessible through the medical record storage component within the clinical integration interface 1170. The stored profile may serve as the template for the patient's subsequent dialysis treatments, ensuring consistency in treatment delivery according to the therapeutic interventions recommended by the healthcare providers during the concurrent telemedicine consultations. The storage process may include version control mechanisms that maintain historical records of previous treatment profiles, enabling clinicians to review how the profile has evolved over time in response to changing clinical conditions. The stored profile may be structured as a machine-readable format that the dialysis machine can directly load and implement, reducing the potential for manual transcription errors when translating clinical recommendations into machine parameter settings. Additionally, the stored profile may include free-text documentation of the clinical reasoning behind specific parameter choices, such as noting that the reduced blood flow rate is implemented due to fistula stenosis identified during the vascular surgeon consultation, providing context for future clinicians reviewing the patient's treatment history.

The process 1300 may be repeated iteratively across multiple dialysis sessions, with continuous refinement of the customized treatment profile based on ongoing clinical assessment and machine learning analysis. In the continuing example, at the patient's next dialysis session scheduled for Thursday morning, the system may load the customized treatment profile generated from Tuesday's consultations and implement the adjusted parameters. The continuous learning pipeline (not shown in FIG. 13 but described in the machine learning system 1100 architecture) may monitor the patient's response to the adjusted parameters, collecting outcome data including whether the patient experienced any complications during treatment, whether the modified blood flow rate achieved adequate dialysis dose, whether the adjusted dialysate glucose concentration improved post-dialysis glucose control, and whether venous pressure measurements remained stable or showed progression of stenosis. This outcome data may be fed back into the machine learning models as labeled training examples, enabling the models to refine their predictions for this specific patient. For example, when the patient undergoes a scheduled procedure or treatment within the next two weeks and subsequently returns to dialysis with improved fistula function following successful treatment, the system may again adjust the customized treatment profile, potentially increasing blood flow rates back toward standard parameters now that the hemodynamically significant stenosis has been resolved. The endocrinologist may schedule a follow-up telemedicine consultation during a future dialysis session to assess the impact of the diabetes management interventions on glucose control, reviewing continuous glucose monitoring data spanning the intervening weeks and making further refinements to the personalized dialysis profile as needed.

The process 1300, implemented in conjunction with the machine learning system 1100, may provide a comprehensive framework for delivering concurrent telemedicine consultations during dialysis treatment sessions while leveraging predictive analytics to optimize treatment parameters based on clinical assessments. The integration of clinical expertise from remote healthcare providers with data-driven insights from machine learning models may enable precision medicine approaches in dialysis care, where treatment parameters are continuously refined based on individual patient characteristics, real-time monitoring data, and predicted complication risks. By automating the translation of therapeutic assessments into implemented interventions through customized treatment profiles, the process 1300 may ensure that clinical recommendations are consistently and accurately applied, reducing variability in care delivery and improving patient outcomes. The process 1300 may be particularly valuable for patients with complex comorbidities requiring multidisciplinary care coordination, as demonstrated in the example where vascular surgery and endocrinology consultations during a single dialysis session led to integrated treatment modifications addressing both access dysfunction and diabetes management considerations.

Figure 14:
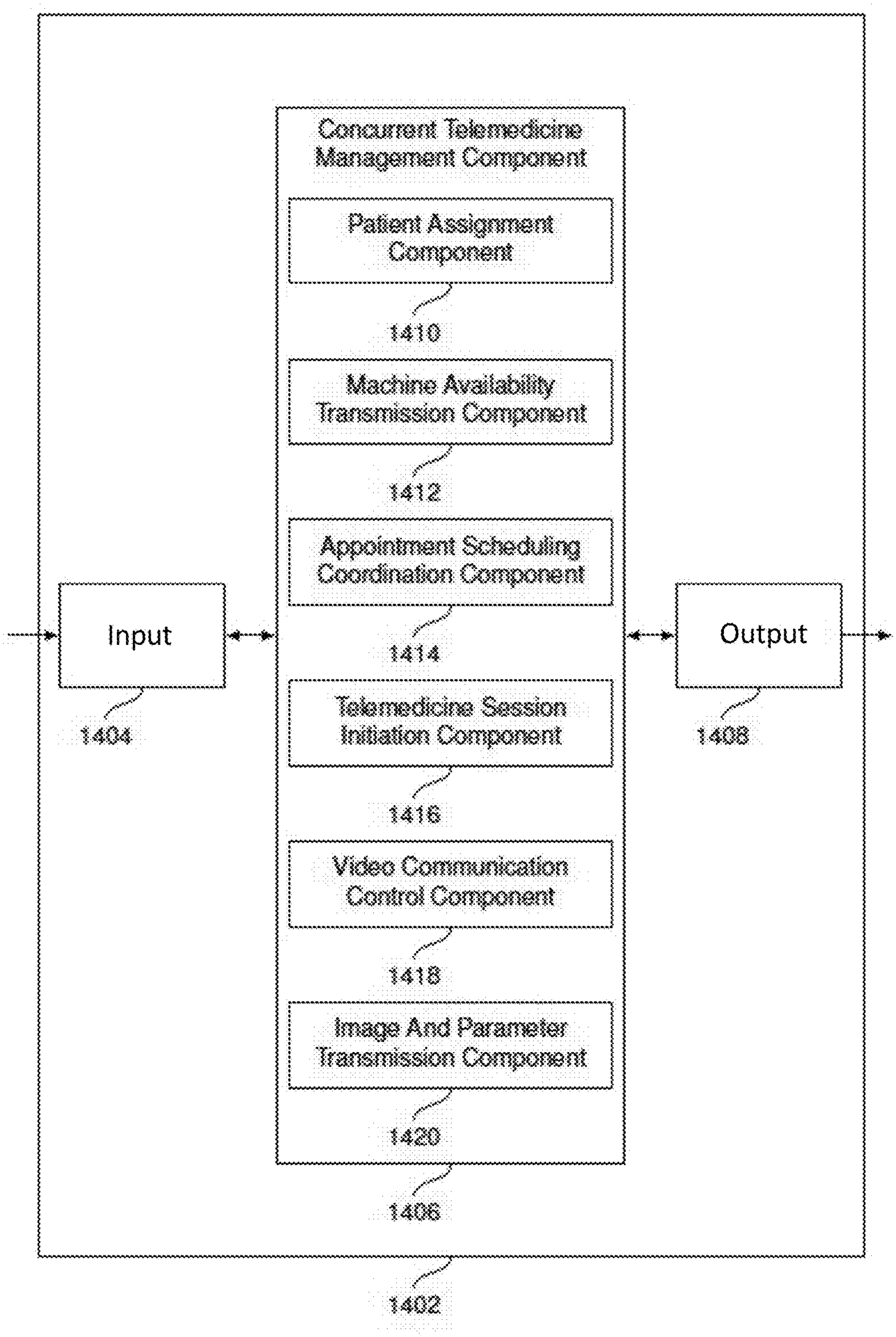
FIG. 14 is a block diagram of an apparatus that supports dialysis machine capabilities integrated telemedicine capabilities and real-time health monitoring.

FIG. 14 is a block diagram of an apparatus 1402 that supports dialysis machine capabilities with integrated telemedicine capabilities and real-time health monitoring. The apparatus 1402 may be the same as or similar to one or more components described in connection with the environment 100 of FIG. 1A-1B and/or FIG. 11. The apparatus 1402 may include an input module 1404, concurrent telemedicine management component 1406, and an output module 1408. The apparatus 1402 may also include or represent one or more processors. Each of these components may be communicatively coupled over one or more buses. In some embodiments, the apparatus 1402 may be an example of a user terminal, a database server, or a system containing multiple computing devices which may be coupled to any number of other medical imaging devices, video devices, server devices, handheld devices, or other electronic device.

The input module 1404 may manage input signals for the apparatus 1402. For example, the input module 1404 may identify input signals based on an interaction with a modem, a keyboard, a medical device, a camera, a mouse, a touchscreen, or any combination thereof. These input signals may be associated with user input, captured data, or processing at other components or devices. The input module 1404 may send all or portions of the input signals to other components of the apparatus 1402 for processing. In some examples, the input module 1404 may be a component of an input/output (I/O) controller (not shown).

The concurrent telemedicine management component 1406 may include one or more of a patient assignment component 1410, a machine availability transmission component 1412, an appointment scheduling coordination component 1414, a telemedicine session initiation component 1416, a video communication control component 1418, an image and parameter transmission component 1420, and/or other components.

The patient assignment component 1410 may represent a means for receiving a patient assignment to a dialysis machine for a scheduled dialysis session. The machine availability transmission component 1412 may represent a means for automatically transmitting dialysis machine availability information to one or more healthcare scheduling systems associated with at least one healthcare provider treating the assigned patient. The appointment scheduling coordination component 1414 may represent a means for coordinating concurrent appointment scheduling between the dialysis session and the at least one healthcare provider. The telemedicine session initiation component 1416 may represent a means for initiating the dialysis session for the assigned patient and, responsive to initiating the dialysis session, automatically establishing a telemedicine session with one or more confirmed healthcare providers according to respective confirmed appointment times by the at least one healthcare provider. The video communication control component 1418 may represent a means for controlling at least one camera and a video monitor to enable concurrent telemedicine communication between the patient and the at least one healthcare provider during the dialysis session. The image and parameter transmission component 1420 may represent a means for causing capture of high-resolution images from a handheld imaging device detachably coupled (or wirelessly coupled) to the dialysis machine, the high-resolution images captured during the telemedicine session and being associated with one or more patient-specific conditions, transmitting the high-resolution images to the at least one healthcare provider during the telemedicine session, and causing transmission of real-time dialysis parameters from the dialysis machine to the at least one healthcare provider during the concurrent telemedicine session.

The output module 1408 may manage output signals for the apparatus 1402. For example, the output module 1408 may receive signals from other components of the apparatus 1402, such as the concurrent telemedicine management component 1406, and may transmit these signals to other components or devices. In some embodiments, the output module 1408 may transmit output signals for display in a user interface, for storage in a database or data store, for further processing at a server or server cluster, or for any other processes at any number of devices or systems. In some embodiments, the output module 1408 may be a component of an I/O controller (not shown).

In a non-limiting example, the apparatus 1402 may process a dialysis session for a patient with both vascular access concerns and diabetic complications. The input module 1404 may receive concurrent data streams including, for example, real-time blood flow parameters from a vascular access monitoring system indicating a venous pressure and/or an arterial pressure of, high-resolution images from a handheld ultrasound device showing an arteriovenous fistula with potential stenosis location(s), vital sign measurements such as blood pressure, heart rate, and oxygen saturation, and blood sample analysis results from a point-of-care diagnostic device indicating potassium levels and/or phosphorus levels. The concurrent telemedicine management component 1406 may coordinate simultaneous consultations with a vascular surgeon reviewing the fistula imaging data and a nephrologist evaluating the laboratory results, while the output module 1408 may transmit synchronized data streams to both healthcare providers' workstations, enabling real-time collaborative assessment during the ongoing dialysis session.

In some embodiments, the concurrent telemedicine management component 1406 may manage arteriovenous fistula maturation assessment workflows. For example, for a patient who underwent recent fistula creation surgery, the patient assignment component 1410 may receive notification that the patient is scheduled for dialysis session monitoring. The machine availability transmission component 1412 may automatically query an arteriovenous fistula maturation assessment system and determine that the fistula has achieved particular predefined one or more of: vessel diameter measurements, blood flow rates, and a depth from skin surface. Based on these parameters indicating maturation, the appointment scheduling coordination component 1414 may automatically coordinate a concurrent vascular surgery consultation during a next dialysis session for the patient. The ranking engine, communicatively coupled to the scheduling system, may prioritize this consultation as high priority based on the maturation milestone, patient preference data indicating availability on particular days and/or times, and surgeon availability. The image and parameter transmission component 1420 may prepare to transmit ultrasound images with annotated measurements showing vessel maturation progress, while the message generator may send confirmation notifications to the patient stating indicators about any assessments of the fistula. For example, the message generator may generate a message such as "Great news! Your fistula has matured successfully. We have scheduled a consultation with Dr. Smith, your vascular surgeon, during your Tuesday 9:00 AM dialysis session to discuss transitioning from your catheter to fistula access."

In a non-limiting example, the apparatus 1402 may implement real-time complication prevention during a dialysis session. The input module 1404 may receive continuous data from a hematocrit detection device monitoring fluid levels at predefined intervals throughout a four hour dialysis session. At the 90 minute mark, the input module 1404 may detect: hematocrit increasing/decreasing, systolic blood pressure increasing/declining, heart rate increasing/decreasing, and patient-reported discomfort score assessments. The concurrent telemedicine management component 1406 may analyze these fluid removal patterns and determine a percentage or prediction of risk for intradialytic hypotension or other condition within an upcoming time period. The component 1406 may trigger automatic adjustment of ultrafiltration rate and simultaneously alert the attending nephrologist through a telemedicine connection about any determined risk or prediction of risk. The system 1100, for example, may store patient data including historical fluid loads and lifestyle metrics, and may retrieve patient baseline data showing typical ultrafiltration tolerances and history of any hypotensive episodes in the previous six sessions when rates exceeded the tolerances. The output module 1408 may transmit updated treatment parameters to the dialysis machine control system and generate a real-time alert on the nephrologist's telemedicine interface displaying indications such as "ALERT: High hypotension risk detected. Ultrafiltration automatically reduced to <determined rate> mL/hr. Patient comfort improving. Review recommended." The message generator may also send the patient a reassurance notification stating: "We've adjusted your treatment to improve your comfort. Your doctor is monitoring your progress remotely."

The apparatus 1402 may further support comprehensive diabetic foot assessment during dialysis sessions. In a non-limiting example, a patient with diabetes and chronic kidney disease may be scheduled for dialysis at 10:00 AM with concurrent podiatry and endocrinology consultations at 11:00 AM and 11:30 AM respectively. The input module 1404 may receive patient assignment data indicating the need for microvascular assessment of a healing foot ulcer. At 11:00 AM, the video communication control component 1418 may establish telemedicine connection with a remote podiatrist while a dialysis technician positions a handheld SFDI (spatial frequency domain imaging) microvascular assessment system over the patient's left foot ulcer, located on the plantar surface beneath the first metatarsal head. The apparatus 1402 may receive, from the SFDI system, hemoglobin biomarkers including, for example, an oxyhemoglobin concentration, a deoxyhemoglobin concentration, tissue oxygen saturation, and normalized hemoglobin index.

The SFDI system may include a structured light projection system including LED light sources at multiple wavelengths (e.g., 660 nm, 850 nm, 970 nm) and a digital micromirror device (DMD) or LCD projector for generating sinusoidal spatial frequency patterns; a CCD or CMOS camera for capturing reflected light images; and processing software implementing Monte Carlo-based light transport models, for example, to extract hemoglobin biomarkers including oxyhemoglobin concentration, deoxyhemoglobin concentration, tissue oxygen saturation, and hemoglobin index from the spatially-modulated reflectance data. The system projects patterns at multiple spatial frequencies and analyzes diffuse reflectance to separate absorption and scattering properties, calculating quantitative maps of tissue oxygenation and perfusion.

The image and parameter transmission component 1420 may transmit these measurements along with high-resolution color images showing any ulcer with surrounding erythema. The podiatrist, using the ultrasound or other imaging device annotation interface, may mark areas of concern and document observations including undermining at the medial ulcer margin extending beyond a predefined measurement. In addition, the apparatus 1402 may integrate tactile feedback system data from a smart glove interface worn by the podiatrist, allowing remote palpation that detects tissue firmness measurements (e.g., of 15 kPa) at the wound edge (normal skin baseline) versus (e.g., 8 kPa) in the surrounding inflamed tissue, indicating edema. Based on the compromised perfusion biomarkers, the appointment scheduling coordination component 1414 may automatically trigger scheduling of a concurrent vascular surgery consultation to assess for peripheral arterial disease, while the endocrinologist consultation at 11:30 AM may review the glucose control data of the patient transmitted from memory, which shows hemoglobin A1c and/or average blood glucose readings over the past 30 days. The output module 1408 may compile a comprehensive report integrating the microvascular assessment data, tactile examination findings, podiatric observations, vascular recommendations, and endocrine management adjustments, storing this multi-specialty assessment in the patient's medical record.

In some embodiments, the apparatus 1402 may coordinate blood sampling and point-of-care diagnostic testing during concurrent telemedicine sessions. For example, during a dialysis session scheduled with a concurrent nephrology consultation at 2:00 PM, the input module 1404 may receive notification at 1:45 PM that the blood sampling interface has collected samples for immediate analysis. A point-of-care diagnostic device communicatively coupled to the apparatus 1402 may perform real-time analysis and generate results within a predefined time period. The concurrent telemedicine management component 1406 may automatically transmit these results to the nephrologist's interface at 1:53 PM, seven minutes before the scheduled consultation, allowing the physician to review the data and formulate recommendations. When the telemedicine session initiates at 2:00 PM, the video communication control component 1418 may display the laboratory values on split-screen alongside the live video feed. The nephrologist may discuss any elevated or abnormal results and adjust prescription(s) and advice. The message generator may document these medication changes and automatically generate prescription notifications transmitted to the patient's pharmacy within minutes of consultation completion. The apparatus 1402 may store these test results and medication adjustments in memory configured for patient data storage, enabling longitudinal tracking of mineral metabolism parameters across successive dialysis sessions.

The apparatus 1402 may orchestrate complex multi-provider telemedicine sessions involving multiple specialties. In a non-limiting example, a patient with CKM syndrome may be scheduled for a 4-hour dialysis session from 8:00 AM to 12:00 PM with three concurrent specialist consultations: cardiology at 9:00 AM, endocrinology at 10:00 AM, and vascular surgery at 11:00 AM. The ranking engine communicatively coupled to the scheduling system may prioritize these appointments based on clinical urgency scoring indicating the cardiology consultation is highest priority due to recent ejection fraction decline, provider availability windows showing limited cardiology appointment slots within the next 14 days, and/or patient preference data from memory storage indicating morning appointments align better with documented patient energy levels and transportation availability. At 8:00 AM, when the dialysis session initiates, the patient assignment component 1410 may load the patient's profile including comorbidity data. The machine availability transmission component 1412 may have previously transmitted dialysis machine scheduling information to all three healthcare scheduling systems, confirming machine availability and session duration sufficient to accommodate all consultations. At 9:00 AM, the telemedicine session initiation component 1416 may automatically establish connection with the cardiologist, while the video communication control component 1418 may activate the camera positioned to capture the patient's upper body for assessment of jugular venous distension, peripheral edema visibility, and facial appearance. The cardiologist may review real-time dialysis parameters transmitted by the image and parameter transmission component 1420, including blood pressure readings, heart rate, and oxygen saturation. The system 100 may store patient data and retrieve such data to provide the cardiologist with historical weight data. During the consultation, the handheld imaging device may be positioned for the dialysis technician to capture video of lower extremities of the patient. The cardiologist may adjust diuretic regimen for the patient and recommend echocardiography to reassess cardiac function. At 10:00 AM, the apparatus 1402 may seamlessly transition to the endocrinology consultation. The appointment scheduling coordination component 1414 may have coordinated timing to allow a buffer between consultations for provider notes documentation. The endocrinologist may review blood glucose data from the patient's continuous glucose monitoring system, integrated through the input module 1404. The point-of-care diagnostic results showing HbA1c or other metrics may be displayed alongside the CGM data. The endocrinologist may adjust insulin dosing and prescribe a newer diabetes medication class (GLP-1 receptor agonist) that provides cardiovascular and renal benefits in addition to glucose control. At 11:00 AM, the vascular surgery consultation may commence. The image and parameter transmission component 1420 may transmit high-resolution ultrasound images of the arteriovenous fistula captured using the handheld imaging device, showing vessel diameter, depth, and flow characteristics. Additionally, images of peripheral pulses may be captured—showing diminished dorsalis pedis and posterior tibial pulses bilaterally. The vascular surgeon may assess both the dialysis access functionality and the peripheral arterial disease status, recommending arterial Doppler studies and consideration for lower extremity revascularization given the claudication symptoms reported by the patient. Throughout all three consultations, the message generator communicatively coupled to the scheduling system may create timestamped documentation of each provider's recommendations, generating a prescription update notification for the adjusted cardiac and diabetes medications sent to the pharmacy, orders for echocardiography, arterial Doppler studies, and follow-up laboratory testing transmitted to the scheduling system, and a patient education message summarizing all three consultations with specific action items for the patient and/or clinical staff. In addition, consultation summary reports may be generated and transmitted to a primary care physician associated with the patient consolidating all specialist recommendations. The output module 1408 may compile a comprehensive multidisciplinary assessment report stored in the patient's electronic medical record, including all transmitted images, real-time dialysis parameters captured during the 4-hour session, specialist recommendations, medication changes, and ordered diagnostic tests. This integrated approach, managed by the apparatus 1402, may enable the patient to receive care from three specialists during a single dialysis session, eliminating the need for three separate office visits that would have involved transportation, time off from work or family obligations, and additional clinic resources, while ensuring coordinated care delivery addressing the interrelated cardiovascular, metabolic, and renal complications of CKM syndrome.

Figure 15:
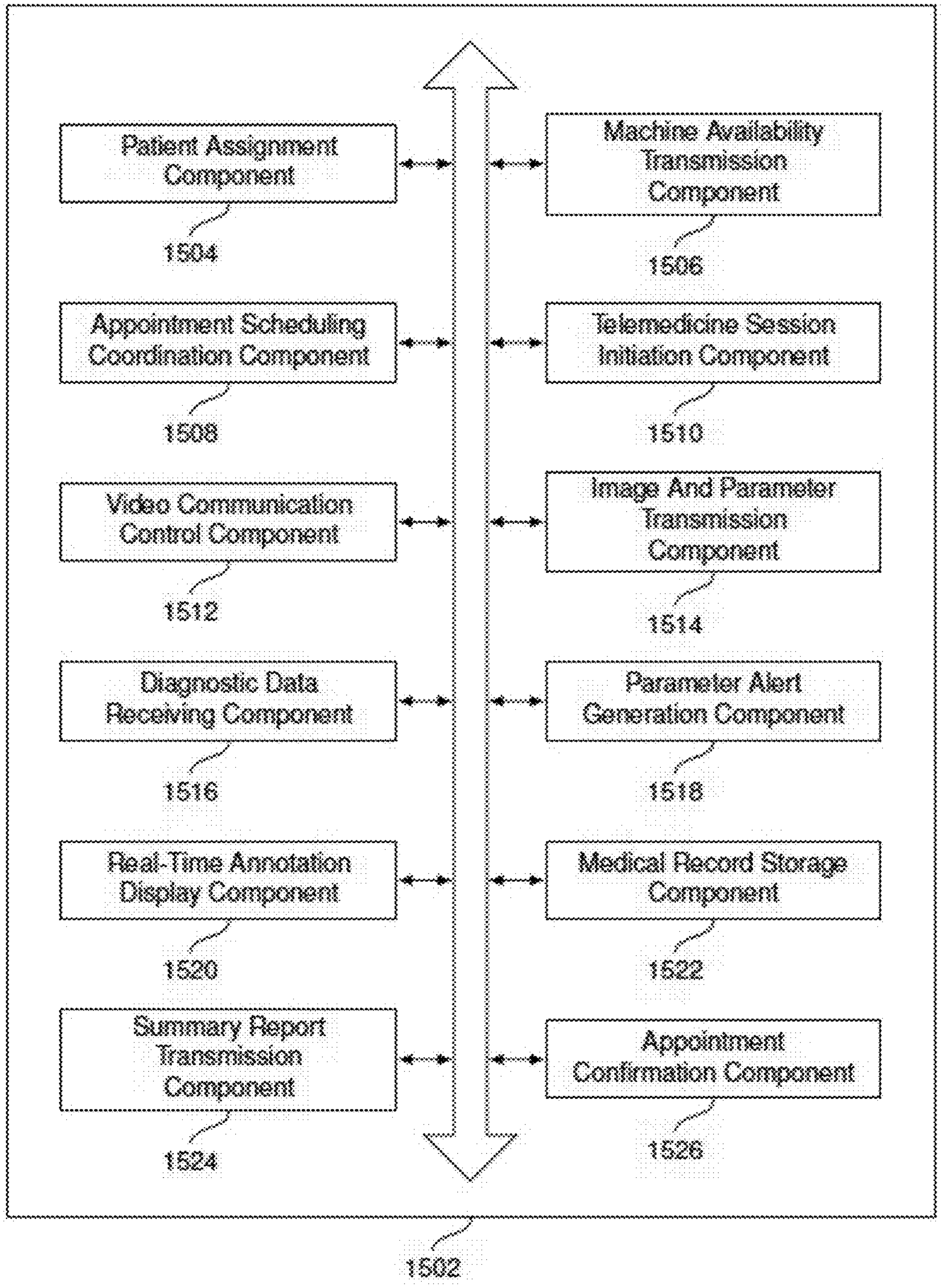
FIG. 15 is a block diagram of a concurrent telemedicine management component that supports dialysis machine capabilities with integrated telemedicine capabilities and real-time health monitoring.

FIG. 15 is a block diagram of a concurrent telemedicine management component that supports dialysis machine capabilities with integrated telemedicine capabilities and real-time health monitoring. The concurrent telemedicine management component 1502 may be an example of aspects of the concurrent telemedicine management component 1406 (FIG. 14). The concurrent telemedicine management component 1502 may represent an example means for performing various aspects of dialysis machine functions, integrated telemedicine capabilities, and real-time health monitoring. For example, the component 1502 may include one or more of a patient assignment component 1504, a machine availability transmission component 1506, an appointment scheduling coordination component 1508, a telemedicine session initiation component 1510, a video communication control component 1512, an image and parameter transmission component 1514, a diagnostic data receiving component 1516, a parameter alert generation component 1518, a real-time annotation display component 1520, a medical record storage component 1522, a summary report transmission component 1524, an appointment confirmation component 1526, and/or other components. Each of the components 1504-1526 may communicate, directly or indirectly, with one another (e.g., over one or more buses).

The patient assignment component 1504 may represent a means for receiving a patient assignment to a dialysis machine for a scheduled dialysis session. In some embodiments, the patient assignment component 1504 may receive input from a scheduling system to determine the specific dialysis machine assigned to the patient. The patient assignment component 1504 may include functionality to receive updates to the assignment based on changes in machine availability or patient preferences. In some embodiments, the patient assignment component 1504 may interface with a database to retrieve historical data about the prior dialysis sessions associated with the patient to inform the assignment process. The patient assignment component 1504 may receive notifications from a maintenance system (not shown) to exclude machines undergoing servicing from the assignment process.

The machine availability transmission component 1506 may represent a means for automatically transmitting dialysis machine availability information to one or more healthcare scheduling systems associated with at least one healthcare provider treating the assigned patient. In some embodiments, the machine availability transmission component 1506 may transmit real-time updates about machine status, including whether a machine is currently in use or idle. The component 1506 may include functionality to transmit information about scheduled maintenance or cleaning times for specific dialysis machines. In some embodiments, the machine availability transmission component 1506 may transmit data about machine location within a facility to assist healthcare scheduling systems in assigning patients to nearby machines.

The appointment scheduling coordination component 1508 may represent a means for coordinating concurrent appointment scheduling between the dialysis session and the at least one healthcare provider. In some embodiments, the appointment scheduling coordination component 1508 may determine overlapping time slots between the dialysis session and the availability of the healthcare provider. In some embodiments, the appointment scheduling coordination component 1508 may receive input from a scheduling system to identify potential conflicts in the proposed concurrent appointments. In some embodiments, the appointment scheduling coordination component 1508 may transmit notifications to the patient and healthcare provider about the confirmed concurrent appointment details.

The telemedicine session initiation component 1510 may represent a means for initiating the dialysis session for the assigned patient and, responsive to initiating the dialysis session, automatically establishing a telemedicine session with one or more confirmed healthcare providers, according to respective confirmed appointment times by the at least one healthcare provider. In some embodiments, the telemedicine session initiation component 1510 may determine the availability of video conferencing equipment integrated into the dialysis machine to establish the telemedicine session. In some embodiments, the telemedicine session initiation component 1510 may transmit a notification to a wearable device associated with the patient indicating the start of the telemedicine session. In some embodiments, the telemedicine session initiation component 1510 may receive input from the patient to confirm readiness for the telemedicine session before initiating communication with the healthcare provider.

In some embodiments, the telemedicine session initiation component 1510 may establish a secure connection to transmit real-time patient data from the dialysis machine to the healthcare provider during the telemedicine session. In some embodiments, the component 1510 may determine whether additional healthcare providers can join the telemedicine session based on their availability and clinical needs of the patient. In some embodiments, the telemedicine session initiation component 1510 may transmit reminders to the healthcare provider about the scheduled telemedicine session to ensure timely participation.

The video communication control component 1512 may represent a means for controlling at least one camera and a video monitor to enable concurrent telemedicine communication between the patient and the at least one healthcare provider during the dialysis session. In some embodiments, the video communication control component 1512 may adjust the camera angle to focus on specific areas of clinical interest, such as a vascular access site of the patient. In some embodiments, the component 1512 may allow the patient to manually reposition the camera using a touchscreen interface integrated into the dialysis machine. In some embodiments, the video communication control component 1512 may determine whether the video monitor can display multiple clinician feeds simultaneously to accommodate consultations with more than one healthcare provider. In some embodiments, the video communication control component 1512 may include functionality to adjust the brightness or resolution of the video monitor based on ambient lighting conditions in a dialysis room.

The image and parameter transmission component 1514 may represent a means for causing capture of high-resolution images from a handheld imaging device detachably coupled (or wirelessly coupled) to the dialysis machine, the high-resolution images captured during the telemedicine session and being associated with one or more patient-specific condition, transmitting the high-resolution images to the at least one healthcare provider during the telemedicine session, and causing transmission of real-time dialysis parameters from the dialysis machine to the at least one healthcare provider during the concurrent telemedicine session. In some embodiments, the image and parameter transmission component 1514 may determine whether the handheld imaging device is securely attached to the dialysis machine before initiating image capture. In some embodiments, the image and parameter transmission component 1514 may allow the handheld imaging device to capture images at multiple angles to accommodate different patient-specific conditions. In some embodiments, the component 1514 may include functionality to store the captured high-resolution images locally on the dialysis machine for later transmission.

The image and parameter transmission component 1514 may transmit the high-resolution images to the at least one healthcare provider during the telemedicine session. In some embodiments, the component 1514 may determine whether the transmitted images meet a predefined resolution threshold to ensure clinical usability. In some embodiments, the image and parameter transmission component 1514 may transmit metadata along with the high-resolution images, such as timestamps or patient identifiers, to assist the healthcare provider in interpreting the images. In some embodiments, the image and parameter transmission component 1514 may transmit the images over a secure connection to comply with privacy regulations.

The image and parameter transmission component 1514 may cause transmission of real-time dialysis parameters from the dialysis machine to the at least one healthcare provider during the concurrent telemedicine session. In some embodiments, the image and parameter transmission component 1514 may determine whether the dialysis parameters include blood pressure, heart rate, and fluid removal rates for real-time monitoring. In some embodiments, the image and parameter transmission component 1514 may transmit the dialysis parameters in a format compatible with the healthcare provider's electronic medical record system. In some embodiments, the image and parameter transmission component 1514 may include functionality to alert the healthcare provider if any transmitted dialysis parameters fall outside predefined clinical thresholds.

In some embodiments, the diagnostic data receiving component 1516 may represent a means for receiving patient-specific diagnostic data from an external wearable device and transmitting the diagnostic data to the at least one healthcare provider during the concurrent telemedicine session. In some embodiments, the component 1516 may determine whether the wearable device is securely paired with the system before initiating data transfer. In some embodiments, the diagnostic data receiving component 1516 may receive diagnostic data such as blood pressure, heart rate, or oxygen saturation levels from the wearable device. In some embodiments, the diagnostic data receiving component 1516 may include functionality to receive periodic updates from the wearable device to ensure real-time monitoring during the telemedicine session. In some embodiments, the component 1516 may determine whether the received diagnostic data meets predefined accuracy thresholds before transmitting it to the healthcare provider. In some embodiments, the diagnostic data receiving component 1516 may transmit metadata, such as timestamps or device identifiers, along with the diagnostic data to assist the healthcare provider in interpreting the information.

In some embodiments, the parameter alert generation component 1518 may represent a means for generating an alert to the at least one healthcare provider in response to detecting a dialysis parameter exceeding a predefined threshold during the concurrent telemedicine session. In some embodiments, the parameter alert generation component 1518 may determine whether the predefined threshold includes parameters such as blood pressure, heart rate, or fluid removal rate. In some embodiments, the component 1518 may transmit the alert through a secure communication channel to comply with privacy regulations. In some embodiments, the parameter alert generation component 1518 may include functionality to generate visual alerts on a monitor associated with the dialysis machine to notify the patient and healthcare provider simultaneously.

In some embodiments, the real-time annotation display component 1520 may represent a means for causing display of real-time annotations from the at least one healthcare provider on the video monitor during the concurrent telemedicine session. In some embodiments, the component 1520 may determine whether the annotations include text-based notes, graphical indicators, or both, to highlight specific areas of clinical interest. In some embodiments, the real-time annotation display component 1520 may allow the healthcare provider to use a stylus or touchscreen interface to input annotations directly onto the video feed. In some embodiments, the real-time annotation display component 1520 may include functionality to adjust the size, color, or opacity of the annotations to accommodate different lighting conditions or patient preferences.

In some embodiments, the medical record storage component 1522 may represent a means for storing the high-resolution images and real-time dialysis parameters in a secure electronic medical record system associated with the assigned patient. In some embodiments, the medical record storage component 1522 may determine whether the electronic medical record system meets predefined security protocols before initiating the storage process. In some embodiments, the medical record storage component 1522 may allow the high-resolution images to be tagged with metadata, such as timestamps or patient identifiers, to assist in organizing the stored records. In some embodiments, the medical record storage component 1522 may include functionality to encrypt the stored dialysis parameters to comply with privacy regulations.

In some embodiments, the summary report transmission component 1524 may represent a means for transmitting a summary report of the telemedicine session, including the high-resolution images and dialysis parameters, to a secondary healthcare provider associated with the assigned patient. In some embodiments, the summary report transmission component 1524 may determine whether the secondary healthcare provider's system is compatible with the format of the transmitted summary report. In some embodiments, the summary report transmission component 1524 may include functionality to transmit the summary report over a secure communication channel to comply with privacy regulations. In some embodiments, the summary report transmission component 1524 may allow the summary report to be segmented into separate files, such as one file for high-resolution images and another for dialysis parameters, to accommodate different data handling preferences of the secondary healthcare provider.

In some embodiments, the appointment confirmation component 1526 may represent a means for receiving appointment confirmation requests from the healthcare scheduling systems and may confirm appointment times that overlap with a portion of the dialysis session. In some embodiments, the appointment confirmation component 1526 may determine whether the requested appointment times align with the availability of the assigned dialysis machine. In some embodiments, the appointment confirmation component 1526 may receive input from the patient to confirm their preference for overlapping appointments during the dialysis session. In some embodiments, the appointment confirmation component 1526 may transmit notifications to the healthcare scheduling systems indicating the confirmed appointment times.

In a non-limiting example component 1502 may perform a complete patient care episode. For example, the patient assignment component 1504 may receive notification that a patient with diabetes and cardiovascular disease has been assigned to a particular dialysis machine for a scheduled Tuesday morning session. The machine availability transmission component 1506 may automatically query the machine's maintenance schedule, confirm operational status, and transmit availability information to healthcare scheduling systems associated with the patient's nephrologist, cardiologist, and podiatrist.

The appointment confirmation component 1526 may receive appointment confirmation requests from multiple healthcare scheduling systems and confirm that the nephrologist consultation can occur during the first hour of dialysis, the cardiologist consultation during the second hour, and the podiatry assessment during the third hour. The appointment scheduling coordination component 1508 may coordinate these confirmations, accounting for dialysis session duration, provider availability windows, and buffer time between consultations.

When the patient arrives for the dialysis session, the telemedicine session initiation component 1510 may initiate the dialysis treatment and automatically establish the first telemedicine connection with the nephrologist according to the confirmed appointment schedule. The video communication control component 1512 may activate the integrated camera system and position the video monitor at an optimal viewing angle for patient-provider interaction.

The diagnostic data receiving component 1516 may receive patient-specific diagnostic data from a wearable device associated with the patient (e.g., a continuous glucose monitoring device) showing glucose trends, variability patterns, and hypoglycemia alert history. Sequentially or simultaneously, the image and parameter transmission component 1514 may cause capture of high-resolution ultrasound images of the patient's arteriovenous fistula and transmit real-time dialysis parameters including blood pressure readings, fluid removal rates, and treatment progress metrics to the nephrologist's workstation.

During the consultation, the nephrologist may use the annotation interface to mark a region of the fistula showing characteristics consistent with developing stenosis. The real-time annotation display component 1520 may cause these annotations to appear simultaneously on both the nephrologist's remote workstation and the video monitor at the patient's dialysis station, enabling the nephrologist to visually communicate areas of clinical concern to the patient and dialysis staff.

As the dialysis session progresses, the parameter alert generation component 1518 may continuously monitor transmitted parameters and detect that the patient's blood pressure has declined below a predefined threshold. The component 1518 may generate an automated alert transmitted to the attending dialysis nurse/clinician and to the cardiologist scheduled for the upcoming consultation, providing advance notice of a hemodynamic parameter requiring evaluation.

When the second telemedicine session begins, the telemedicine session initiation component 1510 may transition from the nephrology consultation to the cardiology consultation, with the video communication control component 1512 maintaining camera positioning while the image and parameter transmission component 1514 adjusts the data stream to emphasize cardiovascular parameters including heart rate, rhythm analysis, and blood pressure trends throughout the dialysis session.

Following the cardiology consultation, the telemedicine session initiation component 1510 may establish the third concurrent session with the podiatrist. The video communication control component 1512 may reposition the camera to focus on the patient's lower extremities or other requested body portion, while a dialysis technician (or user or clinician) uses the handheld imaging device to capture detailed images of a healing diabetic foot ulcer. The image and parameter transmission component 1514 may transmit these high-resolution images along with measurements indicating wound dimensions, surrounding tissue characteristics, and healing progression markers.

Throughout all consultations, the medical record storage component 1522 may continuously store the captured high-resolution images, real-time dialysis parameters, diagnostic data from the wearable device, clinical annotations from all three healthcare providers, and treatment recommendations in a secure electronic medical record system associated with the patient. Upon completion of the dialysis session and all concurrent telemedicine consultations, the summary report transmission component 1524 may compile and transmit comprehensive summary reports to multiple recipients: a detailed clinical summary to the patient's primary care physician documenting all specialist consultations and recommendations, a medication reconciliation report to the patient's pharmacy reflecting prescription adjustments made during the consultations, and a patient-friendly summary to the patient's personal health record application explaining the outcomes of each consultation and listing specific follow-up actions.

The message generator within the concurrent telemedicine management component 1502 may generate and transmit appointment confirmation messages to the patient confirming the scheduled follow-up appointments resulting from the consultations, reminder messages about new medication instructions, and educational content about wound care techniques discussed during the podiatry consultation. This coordinated workflow, managed through the integrated operation of all components within the concurrent telemedicine management component 1502, may enable comprehensive, multi-specialty care delivery during a single dialysis session, with all clinical data captured, annotated, transmitted, stored, and shared among the care team members without requesting that the patient attend separate office visits at multiple locations.

The concurrent telemedicine management component 1502 may be implemented in conjunction with a comprehensive dialysis system architecture that integrates telemedicine capabilities directly into the dialysis treatment infrastructure. The dialysis system may include a dialysis machine having an integrated hemodialysis circuit configured to perform dialysis treatment on a patient, where the hemodialysis circuit includes blood circulation pathways, dialysate delivery systems, and ultrafiltration control mechanisms that remove excess fluid and metabolic waste products from the patient's blood during treatment sessions.

The dialysis system may further include a telemedicine communication module integrated with the dialysis machine to enable remote clinical consultations during dialysis treatment. The telemedicine communication module may include multiple components working in coordination to facilitate bidirectional communication between patients undergoing dialysis and remote healthcare providers. Specifically, the telemedicine communication module may include at least one high-definition camera mounted to the dialysis machine and configured with pan-tilt-zoom capability, enabling dynamic adjustment of camera positioning to capture different viewing angles and focal distances during telemedicine consultations. The camera may be mounted on an adjustable arm attached to the dialysis machine housing, allowing positioning to capture the patient's face and upper body during conversational consultations, or repositioning to focus on specific anatomical areas such as vascular access sites during clinical examinations. The pan-tilt-zoom functionality may be controlled remotely by healthcare providers through the telemedicine interface, or locally by dialysis staff using touchscreen controls, providing flexibility in camera operation to optimize viewing during different consultation types.

The telemedicine communication module may include a video monitor integrated into a control panel of the dialysis machine and configured to display video feeds from remote healthcare providers. The video monitor may be a touchscreen display device positioned at an ergonomic viewing angle for patients in reclined dialysis treatment positions, with display dimensions sufficient for comfortable viewing during multi-hour treatment sessions. The video monitor may be capable of displaying multiple video streams simultaneously, enabling consultations involving multiple healthcare providers or picture-in-picture configurations showing both the remote provider's video feed and locally captured images from the handheld imaging device. The integration of the video monitor into the dialysis machine control panel may provide patients with unified interface access to both dialysis treatment monitoring information and telemedicine consultation displays, eliminating the need for separate external display devices and reducing equipment clutter at the dialysis treatment station.

The telemedicine communication module may include a bidirectional audio-video communication interface configured to establish encrypted video connections with remote workstations. The bidirectional audio-video communication interface may include network connectivity hardware such as Ethernet ports or wireless network adapters, encryption processing circuitry implementing secure communication protocols to protect patient health information during transmission, audio input components including noise-canceling microphones positioned to capture patient speech while filtering ambient dialysis clinic sounds, and audio output components including speakers with adjustable volume settings to accommodate patients with varying hearing capabilities. The bidirectional nature of the interface may enable simultaneous transmission of patient video and audio from the dialysis station to the remote healthcare provider's workstation, while receiving healthcare provider video and audio streams for display and playback at the dialysis station, creating real-time interactive communication comparable to in-person consultations.

The dialysis system may include a docking station physically attached to the dialysis machine and configured to receive a handheld imaging device. The docking station may be mounted to a side panel or surface of the dialysis machine housing, providing a dedicated storage location for the handheld imaging device when not in use during telemedicine consultations. The docking station may include charging contacts configured to engage with corresponding contacts on the handheld imaging device when the device is inserted into the docking station, enabling battery recharging between uses to ensure the device maintains adequate power capacity for clinical imaging procedures. The docking station may include data communication pins arranged in a connector interface configured to mate with a corresponding connector on the handheld imaging device, establishing wired data communication pathways when the device is docked. The data communication interface may support high-speed data transfer enabling the docked handheld imaging device to synchronize captured images with the dialysis machine's storage systems, upload device firmware updates, and download patient-specific imaging protocols or settings.

The dialysis system may include a handheld imaging device mechanically and electrically coupleable to the docking station. The handheld imaging device may be a portable medical imaging instrument designed for bedside clinical use by dialysis technicians, nurses, or clinicians during telemedicine consultations. The handheld imaging device may include an ultrasound transducer configured to emit acoustic waves into patient tissue and detect reflected echoes, enabling visualization of subsurface anatomical structures such as blood vessels, soft tissues, and fluid collections. The ultrasound transducer may be a linear array transducer suitable for vascular imaging applications, with frequency characteristics selected to provide adequate penetration depth for accessing arteriovenous fistulas, grafts, or catheter positions while maintaining sufficient resolution for detailed structural assessment. The handheld imaging device may include image processing circuitry configured to receive raw echo signals from the ultrasound transducer, apply signal processing algorithms to enhance image quality, construct two-dimensional or three-dimensional image representations from the processed signals, and render the images for display on an integrated screen on the handheld device and for transmission to external display systems. The image processing circuitry may implement multiple imaging modes including B-mode imaging for anatomical visualization, color Doppler imaging for blood flow detection and direction assessment, pulsed-wave Doppler imaging for velocity measurement, and power Doppler imaging for sensitive detection of low-velocity flow. The handheld imaging device may include a wireless communication module configured to transmit captured images to the dialysis machine, the telemedicine system, and remote healthcare provider workstations without physical cable connections during device operation, providing operational flexibility for technicians positioning the device during patient examinations.

The concurrent telemedicine management component 1502 may operate in conjunction with the scheduling system 102 that includes structural hardware and software components to manage appointment coordination between dialysis treatment sessions and remote healthcare provider consultations. The scheduling system 102 may include a processor 178, which may be a microprocessor, central processing unit, or application-specific integrated circuit to execute programmed instructions and perform computational operations, as described elsewhere herein. The scheduling system may include memory storing executable instructions that, when executed by the processor, cause the processor to perform specific scheduling and coordination functions supporting concurrent telemedicine consultation delivery.

For example, the processor 178 may maintain a machine availability database tracking operational status of the dialysis machine. The machine availability database may store data records indicating scheduled dialysis treatment sessions, machine maintenance windows, quality assurance testing periods, cleaning and disinfection timeframes, and equipment malfunction or out-of-service periods. The database maintenance operations may include receiving input from dialysis clinic staff regarding scheduled maintenance activities, automatically detecting machine operational status through diagnostic interfaces with the dialysis machine control systems, recording treatment session start and end times as sessions are initiated and completed, and updating availability status in real-time as machine conditions change. The maintained database may provide the foundational data supporting automated scheduling coordination by enabling the system to identify time windows when the dialysis machine is available for patient treatment and concurrent telemedicine consultations.

The processor may transmit availability data to external healthcare scheduling systems through application programming interface (API) connections. The API connections may be established through network interfaces supporting standard communication protocols such as HTTPS, RESTful API architectures, or HL7 FHIR healthcare data exchange standards. The transmitted availability data may be formatted as structured messages containing machine identification information, location details specifying the clinic facility and treatment station, date and time availability windows, session duration capacity, and integrated equipment capabilities such as telemedicine infrastructure and handheld imaging device availability. The transmission operations may occur automatically in response to triggering events such as a patient being assigned to the dialysis machine for a scheduled treatment session, at scheduled intervals such as daily overnight synchronization operations, or in response to queries received from external healthcare scheduling systems seeking available appointment slots for specific patients.

The processor may receive appointment confirmation messages from the external healthcare scheduling systems through the API connections. The appointment confirmation messages may be structured data transmissions containing healthcare provider identification, confirmed appointment date and time, estimated consultation duration, patient identification to match the appointment with the scheduled dialysis session, and consultation type information indicating the medical specialty and purpose of the concurrent consultation. The reception operations may include parsing the received messages to extract relevant data fields, validating that the confirmed appointment times fall within available dialysis session windows, checking for scheduling conflicts with other confirmed appointments, and generating acknowledgment responses confirming successful receipt and processing of the appointment confirmations.

The processor may store confirmed appointment data in a session calendar organizing confirmed appointments in temporal relationship to scheduled dialysis treatment sessions, associating each confirmed telemedicine consultation appointment with the corresponding dialysis session during which the consultation will occur. The stored data may include linkages between patient identifiers, dialysis machine assignments, treatment session times, confirmed healthcare provider appointments, and related clinical information supporting consultation preparation such as relevant medical history, recent laboratory results, or specific clinical concerns prompting the consultation.

The processor may automatically initiate telemedicine connections at scheduled appointment times. The automatic initiation operations may include monitoring current time against stored appointment times in the session calendar, detecting when the current time matches or approaches a scheduled appointment time, retrieving stored connection parameters for the healthcare provider associated with the scheduled appointment including network addresses and authentication credentials, invoking the bidirectional audio-video communication interface to establish an encrypted video connection to the healthcare provider's remote workstation, transmitting session initiation requests or call notifications to the healthcare provider's system, and coordinating with the video communication control component 1512 to activate the camera and configure the video monitor for the beginning consultation.

The dialysis system may include a data transmission module configured to capture dialysis parameter values from dialysis machine sensors and transmit the parameter values through secure network connection during active telemedicine sessions. The data transmission module may include interface circuitry connected to various sensors integrated into the dialysis machine, including blood pressure sensors measuring arterial pressure in the patient's vascular system at regular intervals during treatment, heart rate sensors detecting cardiac rhythm and rate through pulse oximetry or electrocardiogram monitoring, oxygen saturation sensors measuring peripheral blood oxygen levels, blood flow rate sensors measuring the volumetric flow of blood through the dialysis circuit, dialysate flow rate sensors measuring dialysis solution delivery, ultrafiltration rate sensors measuring the rate of fluid removal from the patient, cumulative volume sensors tracking total fluid removed during the session, temperature sensors monitoring dialysate temperature, and conductivity sensors measuring dialysate electrolyte concentration. The data transmission module may include data acquisition circuitry that reads sensor values through electrical interfaces, analog-to-digital converters that transform analog sensor signals into digital data representations, processing logic that formats the captured parameter values into structured data packets, and network communication interfaces that transmit the formatted data packets through secure encrypted network connections to remote healthcare provider workstations during active telemedicine consultation sessions. The transmission may occur continuously or at regular intervals throughout the consultation, providing healthcare providers with real-time visibility into the patient's treatment status and physiological responses during dialysis.

The concurrent telemedicine management component 1502 may coordinate its various functional components with the hardware systems described above to deliver integrated telemedicine consultation services. The patient assignment component 1504 may interface with the scheduling system to receive patient assignment data when a patient is scheduled for treatment on the dialysis machine. The machine availability transmission component 1506 may interface with the scheduling system processor to trigger transmission of availability data to external healthcare scheduling systems when patient assignments occur. The appointment scheduling coordination component 1508 may interface with the scheduling system to manage the reception and processing of appointment confirmation messages. The telemedicine session initiation component 1510 may interface with the scheduling system processor to receive triggers for automatic telemedicine connection establishment at scheduled times. The video communication control component 1512 may interface with the telemedicine communication module to control camera positioning, video monitor display, and audio-video communication functionality. The image and parameter transmission component 1514 may interface with both the handheld imaging device to receive captured images and the data transmission module to receive real-time dialysis parameters, coordinating transmission of both data types to remote healthcare providers during consultations.

The dialysis system may further include a vascular access monitoring system communicatively coupled to the scheduling system processor to enable automated detection of vascular access complications and coordination of appropriate specialist consultations. The vascular access monitoring system may include pressure transducers positioned on arterial and venous lines of the dialysis machine, where these pressure transducers measure pressure at a selectable sampling rate, providing continuous pressure monitoring throughout dialysis treatment sessions. The measured pressures may provide clinically relevant information about vascular access function, where abnormal pressure readings may indicate access dysfunction such as stenosis, thrombosis, or inadequate access maturation.

The vascular access monitoring system may include a blood flow sensor measuring volumetric flow rate. The blood flow sensor may be an ultrasonic flow sensor, magnetic flow sensor, or other non-invasive flow measurement device positioned on the blood circuit tubing to detect blood movement through the dialysis circuit. The measured flow rate may indicate the effectiveness of blood circulation through the dialysis machine, where inadequate flow rates may reflect vascular access problems limiting blood withdrawal from the patient, while flow rates within expected ranges indicate proper access function supporting adequate dialysis treatment delivery.

The vascular access monitoring system may include a monitoring processor configured to analyze the measured pressure and flow data to assess vascular access function. The monitoring processor may be a dedicated microprocessor, microcontroller, or processing logic implemented within the dialysis machine control systems, configured to execute specific analytical algorithms related to vascular access assessment. The monitoring processor may be configured to calculate pressure-flow relationships from the measured pressures and flow rates, where these relationships characterize how pressure measurements correlate with achieved blood flow through the access. Normal vascular access function typically demonstrates predictable pressure-flow relationships, where specific pressure differentials correspond to expected flow rates based on access type, patient vascular characteristics, and dialysis machine pump settings. The monitoring processor may apply mathematical functions or lookup tables to calculate expected pressure-flow relationships and compare them to measured values.

The monitoring processor may compare calculated relationships to baseline patient-specific values stored in memory. The memory storage may contain historical pressure and flow data from the patient's previous dialysis sessions, establishing baseline normal values representing typical access function for this specific patient. The comparison operations may calculate deviations between current calculated pressure-flow relationships and the stored baseline values, identifying when current measurements differ significantly from the patient's established normal patterns. This patient-specific comparison approach may provide greater sensitivity for detecting access dysfunction compared to population-based thresholds, since individual patients may have different baseline vascular characteristics affecting pressure and flow measurements.

The monitoring processor may generate a dysfunction score based on deviation from baseline. The dysfunction score may be a numerical value or categorical classification quantifying the likelihood or severity of vascular access dysfunction based on the magnitude of deviation between current measurements and baseline values. The scoring algorithm may weight different types of deviations differently based on their clinical significance, such as assigning higher dysfunction scores to progressive increases in venous pressure over multiple sessions compared to isolated single-session pressure elevations. The dysfunction score may be calculated using rule-based algorithms implementing clinical decision logic, statistical methods calculating standard deviations from baseline means, or machine learning models trained on historical access monitoring data with known outcomes.

The monitoring processor may be configured to output an alert signal when the dysfunction score exceeds a threshold value stored in memory. The threshold value may be a predetermined numerical cutoff selected based on clinical experience or validation studies to balance sensitivity for detecting true access dysfunction against specificity for avoiding false alarms from benign measurement variations. When the calculated dysfunction score exceeds the stored threshold, the monitoring processor may generate an alert signal transmitted through electrical signaling, data message transmission, or other communication mechanisms to notify relevant system components and clinical personnel of the detected potential access dysfunction that would benefit from evaluation.

The processor may receive the alert signal and may initiate automated scheduling coordination to arrange appropriate follow-up evaluation. The processor may query availability databases of vascular surgery providers, where these queries may be transmitted through API connections to external healthcare scheduling systems associated with vascular surgeons or interventionalists who treat dialysis access complications. The queries may include patient identification information, clinical urgency indicators based on the dysfunction score severity, and desired timeframe for consultation such as requesting appointments within the next seven to fourteen days for moderate dysfunction scores or within the next predefined time period for severe dysfunction scores indicating high risk of imminent access failure.

The processor may be configured to transmit appointment request messages over a network interface when the alert signal is received. The appointment request messages may be structured communications sent to identified vascular surgery provider scheduling systems, proposing specific appointment times that align with the patient's scheduled dialysis sessions to enable concurrent telemedicine consultation during dialysis treatment, or alternatively requesting in-person clinic appointments if the dysfunction severity or suggested interventions necessitate evaluation in a vascular surgery office or procedure suite. The transmitted messages may include relevant clinical data supporting the consultation request, such as trending graphs of venous pressure measurements showing progressive increases over recent sessions, current dysfunction scores, and relevant patient history including access type, creation date, and any previous access complications or interventions.

This comprehensive structural and functional architecture enables the concurrent telemedicine management component 1502 to operate within an integrated dialysis system that combines treatment delivery infrastructure with telemedicine communication capabilities, automated scheduling coordination, real-time patient monitoring, and proactive clinical decision support.

In some embodiments, the system 1502 may represent a system for enabling healthcare provider consultations during dialysis. The system may include a video communication interface positioned proximate to a patient receiving dialysis treatment and configured to establish video connections with remote healthcare providers. The system may include an imaging device configured to capture images of patient conditions and transmit images to the remote healthcare providers during the video connections. In such a system, the dialysis treatment parameters may be transmitted to the remote healthcare providers in coordination with the video connections.

Figure 16:
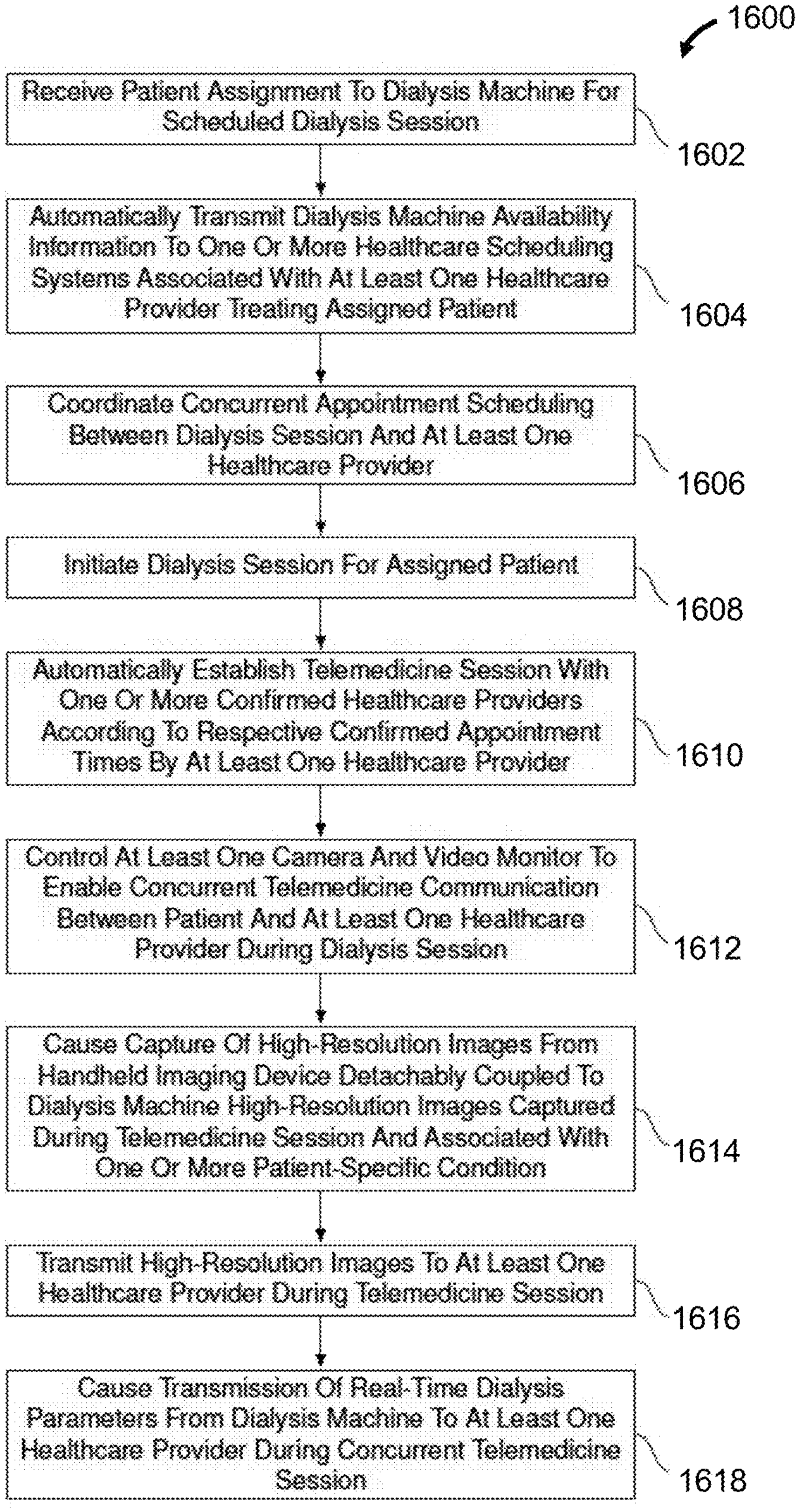
FIG. 16 is a flow diagram illustrating a process that supports dialysis machine capabilities with integrated telemedicine capabilities and real-time health monitoring.

FIG. 16 is a flow diagram illustrating a process 1600 that supports dialysis machine capabilities with integrated telemedicine capabilities and real-time health monitoring. The complete process 1600 may demonstrate a comprehensive integrated workflow that transforms dialysis treatment from an isolated procedure into a coordinated care opportunity. By enabling concurrent specialist consultations during dialysis sessions, capturing and transmitting high-resolution diagnostic images, analyzing treatment parameters through machine learning algorithms, and ensuring care team communication through automated reporting, the process 1600 may achieve multiple clinical benefits including reduced patient travel burden, improved access to specialist expertise, earlier detection of access complications, optimized treatment parameter management, and enhanced care coordination across multiple providers. The process 1600 may be particularly beneficial for patients with complex medical conditions utilizing multidisciplinary care, patients in rural or underserved areas with limited access to specialty expertise, and patients with transportation barriers that make attending multiple separate appointments challenging. By bringing specialist consultations to the patient during already-scheduled dialysis sessions, the process 1600 may improve both clinical outcomes through timelier interventions and patient quality of life through reduced healthcare-related time and travel burdens.

The operations of the methods described herein may be implemented by one or more of a device, an apparatus, a system (e.g., a networked computing system), and/or components thereof as described herein. For example, the operations of the method 1600 may be performed by a concurrent telemedicine management component as described with reference to systems 100, 102, 1100, 1400, and/or 1500. In some examples, one or more components of a device, apparatus, and/or system may execute a set of computer-readable instructions to control the functional elements of the component(s) to perform the described functions. Additionally or alternatively, the one or more components of a device, apparatus, and/or system may perform aspects of the described functions using special-purpose hardware.

At block 1602, the process 1600 may include receiving a patient assignment to a dialysis machine for a scheduled dialysis session. The operations of block 1602 may be performed in accordance with examples as disclosed herein. In some examples, aspects of the operations of 1602 may be performed by a patient assignment component 1504 (FIG. 15). For example, the patient assignment component may receive notification that a patient in need of vascular access evaluation has been assigned to a particular dialysis machine for a Wednesday afternoon session scheduled from 1:00 PM to 5:00 PM. The patient assignment may include metadata indicating the patient has an arteriovenous fistula created eight weeks prior and should have a maturation assessment before transitioning from temporary catheter access.

At block 1604, the process 1600 may include automatically transmitting dialysis machine availability information to one or more healthcare scheduling systems associated with at least one healthcare provider treating the assigned patient. The operations of block 1604 may be performed in accordance with examples as disclosed herein. In some examples, aspects of the operations of 1604 may be performed by the machine availability transmission component 1506 (FIG. 15). For example, the system 100, 1100, and/or scheduling engine 112 may automatically transmit dialysis machine availability information to healthcare scheduling systems associated with the patient's nephrologist and vascular surgeon. The transmitted information may include the confirmed four-hour dialysis session window, machine location within the dialysis clinic, integrated telemedicine equipment availability, and handheld ultrasound imaging device attachment confirmation. The transmission may occur within seconds of the patient assignment, enabling the healthcare scheduling systems to identify the Wednesday 2:30 PM to 3:15 PM time window as optimal for concurrent vascular surgery consultation based on surgeon availability and typical fistula examination duration requirements.

At block 1606, the process 1600 may include coordinating concurrent appointment scheduling between the dialysis session and the at least one healthcare provider. The operations of block 1606 may be performed by the appointment scheduling coordination component 1508 (FIG. 15). For example, the 100, 1100, and/or scheduling engine 112 may coordinate concurrent appointment scheduling by receiving availability responses from both healthcare scheduling systems. The nephrologist's scheduling system may confirm availability for a brief check-in consultation at 1:15 PM (fifteen minutes after dialysis initiation to allow for treatment stabilization), while the vascular surgeon's system may confirm availability for the comprehensive fistula assessment at 2:30 PM. The coordination process may account for the sequential nature of these consultations, ensuring adequate time for the nephrologist to review overall patient status before the vascular surgeon performs detailed access evaluation.

At block 1608, the process 1600 may include initiating the dialysis session for the assigned patient. The operations of block 1608 may be performed by the telemedicine session initiation component 1510 (FIG. 15). For example, when the patient arrives at 12:45 PM and the dialysis session initiates at 1:00 PM using the temporary catheter access, the system may begin monitoring session parameters and preparing for the scheduled telemedicine consultations. The initiation process may include verifying camera and video monitor functionality, confirming handheld ultrasound device attachment to the dialysis machine docking station, and loading the patient's electronic medical record data including previous fistula imaging from the surgical creation procedure eight weeks prior.

At block 1610, the process 1600 may include, responsive to initiating the dialysis session, automatically establishing a telemedicine session with one or more confirmed healthcare providers, according to respective confirmed appointment times by the at least one healthcare provider. The operations of block 1610 may be performed by the appointment confirmation component 1526 (FIG. 15). For example, responsive to initiating the dialysis session, the system may automatically establish the first telemedicine session with the nephrologist at 1:15 PM according to the confirmed appointment time. The nephrologist may review current treatment parameters and confirm the patient is tolerating the dialysis session appropriately. At 2:30 PM, the system may automatically establish the second telemedicine session with the vascular surgeon according to the confirmed appointment schedule. The transition between consultations may be seamless, with the system maintaining continuous parameter monitoring while switching healthcare provider connections.

At block 1612, the process 1600 may include controlling at least one camera and a video monitor to enable concurrent telemedicine communication between the patient and the at least one healthcare provider during the dialysis session. The operations of block 1612 may be performed by a video communication control component 1512 (FIG. 15). For example, the system may control the integrated camera system and video monitor throughout both consultations. During the nephrologist consultation, the camera may be positioned to capture the patient's upper body for general assessment and conversation. When the vascular surgeon consultation begins at 2:30 PM, the system may automatically reposition the camera to focus on the patient's left arm where the arteriovenous fistula is located. The video monitor may display the surgeon's video feed, allowing bidirectional visual communication while the dialysis technician assists with fistula examination positioning.

At block 1614, the process 1600 may include causing capture of high-resolution images from a handheld imaging device detachably coupled (or wirelessly coupled) to the dialysis machine, the high-resolution images captured during the telemedicine session and being associated with one or more patient-specific condition. The operations of block 1614 may be performed by an image and parameter transmission component 1514 as described with reference to FIG. 15. For example, during the vascular surgeon consultation, the system may cause the handheld ultrasound imaging device to capture high-resolution images of the arteriovenous fistula. A trained dialysis technician may position the ultrasound probe at multiple locations along the fistula length, capturing images showing: the anastomosis site where the artery connects to the vein, the venous outflow tract extending from the anastomosis toward the central circulation, vessel diameter measurements at standardized locations, blood flow velocity waveforms using ultrasound capabilities, and depth measurements from the skin surface to the vessel center. The high-resolution images may be captured in real-time as the vascular surgeon provides verbal guidance to the technician regarding probe positioning and image optimization. These patient-specific images may be directly relevant to determining fistula maturation status and suitability for dialysis access use.

At block 1616, the process 1600 may include transmitting the high-resolution images to the at least one healthcare provider during the telemedicine session. The operations of block 1616 may be performed by an image and parameter transmission component 1514 (FIG. 15). For example, the system may transmit the high-resolution ultrasound images to the vascular surgeon's workstation during the telemedicine session with minimal latency. The transmission may occur continuously as images are captured, enabling the surgeon to provide real-time feedback on image quality and request additional views or measurements. The surgeon may view the transmitted images on a high-resolution medical-grade display at the remote location, with image quality sufficient for clinical decision-making regarding fistula maturation status. During the consultation, the surgeon may use an annotation interface to mark specific anatomical features on the transmitted images, such as identifying the optimal cannulation zone for future dialysis needle placement or highlighting areas that would benefit from monitoring for potential stenosis development.

At block 1618, the process 1600 may include causing transmission of real-time dialysis parameters from the dialysis machine to the at least one healthcare provider during the concurrent telemedicine session. The operations of block 1618 may be performed by an image and parameter transmission component 1514 (FIG. 15). For example, the system may cause transmission of real-time dialysis parameters from the dialysis machine and transmission of the images to the vascular surgeon during the concurrent telemedicine session. The transmitted parameters may include current blood pressure readings, heart rate, oxygen saturation, treatment time elapsed, cumulative fluid removed, and ultrafiltration rate. These parameters may provide the surgeon with context about the patient's hemodynamic stability and overall dialysis tolerance, which may be relevant factors when determining the timeline for transitioning from catheter to fistula access. The parameter transmission may continue throughout the consultation, with the surgeon able to monitor any changes in patient status during the examination.

In operation, following the image and parameter transmission at blocks 1614-1618, the process 1600 may include receiving from the vascular surgeon one or more clinical assessments based on the high-resolution images. The surgeon may provide a fistula maturation assessment indicating that the arteriovenous fistula has achieved adequate maturation parameters including sufficient vessel diameter, appropriate flow rates, and acceptable depth from the skin surface. Based on this assessment, the surgeon may recommend transitioning from catheter to fistula access for the patient's next dialysis session, or alternatively, continuing catheter use for an additional period if maturation characteristics suggest inadequate development. The received assessment may also include a vascular access diagnosis addressing the current functional status of both the temporary catheter and the maturing fistula, documenting blood flow adequacy and absence of complications such as aneurysm formation, stenosis, or thrombosis. This comprehensive evaluation may inform a patient dialysis profile recommendation specifying the timeline for access transition, needle gauge recommendations for initial fistula cannulation, target blood flow rates, and monitoring protocols to ensure continued fistula function.

The system may implement a machine learning model that analyzes the plurality of dialysis parameters transmitted during the session and captured in the patient's historical treatment records, including blood pressure trends, ultrafiltration rates and patient tolerance, interdialytic weight gains, and documented complications. Based on this analysis, the model may predict patient complications that could occur during future dialysis sessions, such as elevated risk for muscle cramps due to historical patterns of rapid ultrafiltration, hypotension risk when larger interdialytic weight gains suggest aggressive fluid removal, and fluid overload risk based on patterns of inconsistent interdialytic weight gains and dietary non-adherence indicators. The model may automatically generate recommendations for adjusting dialysis machine parameters to preemptively prevent the predicted complications, including implementing modified ultrafiltration profiles that remove fluid more gradually, setting automated alerts if blood pressure declines below patient-specific thresholds, adjusting dialysate sodium concentration to improve patient comfort, and extending treatment duration when larger fluid volumes are to be removed. The machine learning model may generate a customized treatment profile incorporating these parameter adjustments specifically tailored to the patient's physiological responses and complication risk profile. This customized treatment profile may be stored in the patient record within the electronic medical record system, where it becomes the template for future dialysis sessions and may be continuously refined as the model analyzes outcomes from subsequent treatments.

Following completion of the telemedicine consultations during the dialysis session, the system may automatically compile and transmit a comprehensive summary report to secondary healthcare providers associated with the patient, such as the patient's primary care physician who manages the patient's diabetes and cardiovascular conditions. The transmitted summary report may include the high-resolution ultrasound images with embedded annotations marking clinically significant features, a complete set of dialysis parameters recorded throughout the treatment session, documentation of both telemedicine consultations including the nephrologist's assessment and the vascular surgeon's fistula maturation assessment with specific recommendations, and the customized treatment profile generated by the machine learning model including predicted complication risks and recommended parameter adjustments. The summary report transmission may enable comprehensive care coordination, ensuring secondary providers are informed about the patient's dialysis progress, vascular access status, and treatment modifications. The system may also transmit tailored versions of the summary report to other members of the patient care team, such as diabetes educators who may receive information about fluid management and dietary adherence, or home health clinicians who monitor catheter exit sites.

Figure 17:
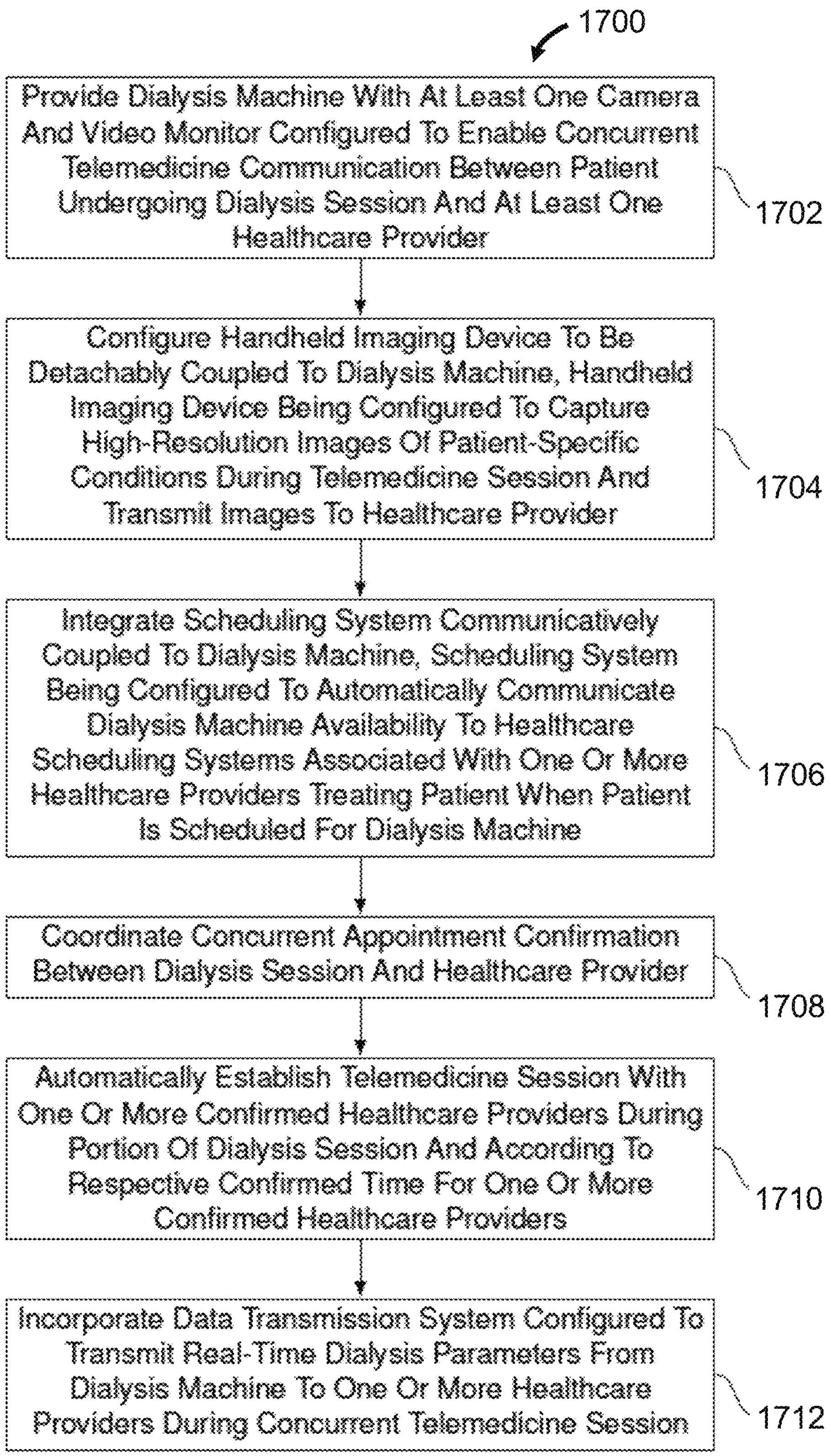
FIG. 17 is a flow diagram illustrating a process 1700 for scheduling and establishing telemedicine sessions during dialysis machine sessions.

FIG. 17 is a flow diagram illustrating a process 1700 for scheduling and establishing telemedicine sessions during dialysis machine sessions. The complete process 1700 implementation may transform a standard dialysis station into a comprehensive telemedicine-enabled treatment environment, where patients can receive specialized medical consultations without leaving the dialysis chair or traveling to additional appointments. For example, a patient who previously would have involved three separate office visits to see their cardiologist, podiatrist, and nephrologist in different medical buildings on different days may instead receive all three consultations during their already-scheduled dialysis sessions over the course of a single week. The process 1700 may be particularly valuable for patients with limited mobility who find travel to multiple appointments burdensome, patients in rural areas who drive significant distances to reach specialist offices, elderly patients who rely on family members or medical transportation services for healthcare visits, and patients whose work schedules make attending multiple daytime appointments difficult. By integrating telemedicine capabilities directly into the dialysis treatment environment and automating the scheduling and connection processes, the process 1700 may improve patient access to multi-specialty care, enhance care coordination among providers treating complex patients with multiple comorbidities, reduce patient time burden and transportation costs, and enable more frequent specialist monitoring without requiring additional clinic visits. The systematic approach described in process 1700, from initial equipment provision through automated session establishment and real-time data transmission, may provide a comprehensive framework for deploying telemedicine capabilities in dialysis facilities of various sizes and configurations, supporting both large dialysis organizations operating multiple facilities and smaller independent dialysis clinics seeking to enhance care delivery capabilities.

At block 1702, the process 1700 may include providing a dialysis machine with at least one camera and a video monitor configured to enable concurrent telemedicine communication between a patient undergoing a dialysis session and at least one healthcare provider. Providing the dialysis machine with integrated telemedicine capabilities may include installing or configuring at least one high-definition camera and a video monitor at each dialysis treatment station. For example, a dialysis clinic may equip a dialysis station with a pan-tilt-zoom camera mounted on an adjustable arm attached to the dialysis machine housing, positioned to capture the patient's upper body and face during consultations while allowing remote adjustment of camera angle and zoom level by healthcare providers. The video monitor may be a touchscreen display integrated into the dialysis machine control panel, sized appropriately for patient viewing during treatment sessions (such as a display measuring between fifteen and twenty-four inches diagonally), and positioned at an ergonomic viewing angle for patients in reclined treatment positions. The camera and video monitor may be communicatively coupled to the dialysis machine through wired connections integrated into the machine's electronics enclosure, or alternatively through secure wireless connections using encrypted protocols to protect patient privacy. The configuration may enable bidirectional audio and video communication, allowing both the patient and the remote healthcare provider to see and hear each other in real-time during concurrent telemedicine sessions. The system may include noise-cancellation microphones to filter ambient dialysis clinic sounds, ensuring clear audio communication despite the operational noise from multiple dialysis machines, and speakers with adjustable volume to accommodate patients with varying hearing capabilities.

At block 1704, the process 1700 may include configuring a handheld imaging device to be detachably coupled (or wirelessly coupled) to the dialysis machine, the handheld imaging device being configured to capture high-resolution images of patient-specific conditions during the telemedicine session and transmit the images to the healthcare provider. Configuring the handheld imaging device may enable dialysis technicians or other clinicians to quickly retrieve the handheld device during telemedicine consultations, position it for capturing high-resolution images of patient-specific conditions such as arteriovenous fistulas or catheter exit sites, and view real-time imaging feedback on an integrated display screen on the handheld device itself. The device may automatically establish secure wireless communication with the dialysis machine upon removal from the docking station, enabling seamless image transmission to both the dialysis machine video monitor for patient and bedside staff viewing, and to the remote healthcare provider's workstation for clinical evaluation. The handheld imaging device may support multiple imaging modes including B-mode ultrasound for anatomical visualization, color Doppler for blood flow assessment, and pulsed-wave Doppler for velocity measurements, providing comprehensive vascular access evaluation capabilities. The configuration may also include annotation tools accessible through touchscreen controls on the handheld device, allowing clinicians to mark regions of interest, measure vessel diameters, calculate flow rates, and document findings directly on captured images during the telemedicine session.

At block 1706, the process 1700 may include integrating a scheduling system communicatively coupled to the dialysis machine, the scheduling system being configured to automatically communicate dialysis machine availability to healthcare scheduling systems associated with one or more healthcare providers treating the patient when the patient is scheduled for the dialysis machine. Integrating the scheduling system may include establishing bidirectional communication between the dialysis machine and external healthcare scheduling systems through secure application programming interfaces (APIs) or health information exchange protocols. For example, when a patient is assigned to dialysis machine Station 3B for a scheduled Monday, Wednesday, Friday treatment regimen, the scheduling system may automatically query the dialysis machine's availability calendar and confirm that the machine has completed maintenance, passed quality assurance testing, and had no conflicting patient assignments during the requested time slots. The scheduling system may then automatically communicate this confirmed dialysis machine availability to healthcare scheduling systems associated with the patient's treating physicians, which may include the patient's nephrologist, cardiologist, endocrinologist, vascular surgeon, and primary care physician.

At block 1708, the process 1700 may include coordinating concurrent appointment confirmation between the dialysis session and the healthcare provider. Coordinating concurrent appointment confirmation may include the scheduling system managing a multi-party confirmation workflow among the patient, the dialysis machine scheduling, and multiple healthcare provider scheduling systems. In a non-limiting example, when the scheduling system identifies that a patient with diabetes and cardiovascular disease is scheduled for dialysis on Tuesday from 2:00 PM to 6:00 PM, the system may send appointment availability notifications to the healthcare scheduling systems for the patient's cardiologist and podiatrist. The cardiologist's scheduling system may respond that the physician is available for a telemedicine consultation from 3:00 PM to 3:30 PM, while the podiatrist's scheduling system may indicate availability from 4:15 PM to 4:45 PM. The scheduling system may then send a confirmation request to the patient through the patient's preferred communication channel (such as a mobile application, text message, or email), presenting the proposed concurrent appointment times and requesting acceptance or modification. When the patient confirms acceptance of both concurrent appointments, the scheduling system may send final confirmation messages to all parties, update the dialysis machine's appointment calendar to reserve the telemedicine equipment during the confirmed consultation times, and generate appointment reminders to be delivered at appropriate intervals before the scheduled session. The coordination process may also account for appointment dependencies, such as ensuring adequate spacing between sequential consultations to allow time for each healthcare provider to complete their evaluation and documentation, and preventing double-booking scenarios where multiple providers might attempt to schedule overlapping consultation times.

At block 1710, the process 1700 may include automatically establishing a telemedicine session with one or more confirmed healthcare providers during a portion of the dialysis session and according to a respective confirmed time for the one or more confirmed healthcare providers. Automatically establishing the telemedicine sessions may include the system detecting dialysis treatment initiation and subsequently connecting with confirmed healthcare providers at their respective scheduled appointment times. For example, when the patient arrives for the Tuesday 2:00 PM dialysis session and treatment begins, the system may monitor the elapsed session time and automatically initiate the first telemedicine connection at 3:00 PM to establish communication with the cardiologist. The automatic establishment process may include multiple steps executed by the system: authenticating the healthcare provider's credentials to ensure secure access, testing audio and video connectivity to verify proper equipment function, adjusting camera positioning to optimize patient visibility for the specific consultation type, loading relevant patient medical record data onto the healthcare provider's telemedicine interface, and displaying connection status notifications on both the dialysis clinic's video monitor and the provider's remote workstation. At 3:00 PM, the system may automatically place a video call to the cardiologist's telemedicine workstation, and when the provider answers the call, establish the bidirectional audio-video connection. The patient may receive a notification on the dialysis machine's video monitor stating that their cardiology consultation is beginning, and the video feed may transition from displaying entertainment or educational content to showing the cardiologist's video. Upon completion of the cardiology consultation at approximately 3:30 PM, the system may automatically terminate that telemedicine session, return the video monitor to its previous content, and prepare for the next scheduled consultation. At 4:15 PM, the system may repeat the automatic establishment process for the podiatry consultation, connecting with the podiatrist according to the confirmed appointment schedule. This automatic establishment eliminates the need for dialysis staff to manually initiate video calls or coordinate connection logistics, reducing staff workload while ensuring reliable consultation delivery.

At block 1712, the process 1700 may include incorporating a data transmission system configured to transmit real-time dialysis parameters from the dialysis machine to one or more of the healthcare providers during the concurrent telemedicine session. Incorporating the data transmission system may include configuring continuous streaming of real-time dialysis parameters from the dialysis machine's monitoring systems to the healthcare provider's telemedicine interface throughout the concurrent consultation. In the example consultation scenario, when the cardiologist connects at 3:00 PM, the data transmission system may immediately begin sending current treatment parameters including the patient's blood pressure measured by the dialysis machine's integrated blood pressure monitoring system (such as readings captured every fifteen to thirty minutes during treatment), heart rate detected through pulse oximetry sensors attached to the patient, oxygen saturation percentage indicating respiratory function, blood flow rate through the dialysis circuit showing the volume of blood being processed per minute, dialysate flow rate indicating the volume of dialysis solution being used, ultrafiltration rate showing the rate of fluid removal from the patient, cumulative fluid volume removed since treatment initiation, treatment time elapsed and remaining, and venous and arterial pressure measurements within the dialysis circuit. These parameters may be displayed on the cardiologist's telemedicine workstation in a structured format, such as a sidebar panel adjacent to the video feed showing current values with trend indicators, or as graphical charts displaying parameter progression over the course of the dialysis session. The real-time transmission may enable the cardiologist to assess the patient's hemodynamic response to dialysis treatment, evaluate fluid removal tolerance, and make informed recommendations about cardiac medication adjustments, target dry weight modifications, or ultrafiltration rate changes based on observed treatment parameters. Similarly, when the podiatrist connects at 4:15 PM, the data transmission system may continue streaming the same parameters, which may provide the podiatrist with relevant context about the patient's cardiovascular stability and treatment tolerance during the foot examination. The data transmission system may also support bi-directional communication, allowing healthcare providers to request additional parameters or measurements, such as asking the dialysis staff to capture an electrocardiogram reading or measure standing blood pressure for comparison to seated treatment values.

The systems described herein may generate requisite warnings to protect the information contained in data accessed and/or stored by such systems in compliance with the Health Insurance Portability and Accountability Act (HIPPA). Accordingly, the systems and methods described herein provide compliance with HIPPA, and other privacy requirements regarding patient medical data, or other personal information. For example, the processes 500, 600, 700, 800, 900, and 1000 are executed in such a fashion to be HIPPA compliant and requisite warnings are provided to protect the information contained in system 102 in compliance with HIPPA.

The systems and methods of the implementations described herein and/or variations thereof can be embodied and/or implemented at least in part as a machine configured to receive a computer-readable medium (or computer program product) storing computer-readable instruction. The instructions are executed by computer-executable components integrated with the system and one or more portions of the hardware processor 178 communicatively coupled computing device. The computer-readable medium (or computer program product) can be stored on any suitable computer-readable media (e.g., memory 180) such as RAMs, ROMs, flash memory, EEPROMs, optical devices (e.g., CD or DVD), hard drives, floppy drives, or any suitable device. The computer-executable component can be a general or application-specific hardware processor, but any suitable dedicated hardware or hardware/firmware combination can alternatively or additionally execute the instructions.

A computer program product can be tangibly embodied in an information carrier. The computer program product may also contain instructions that, when executed, perform one or more methods and/or computer-implemented methods described herein. The information carrier may be a computer- or machine-readable medium, such as the memory 180, or other storage associated with system 102 and/or wearable device 132 and/or processors 178. In general, the scheduling engine 112, communication engine 114, and optimizer engine 116 and their respective modules, generators, or detectors may each be executed to carry out the steps and algorithms described herein using one or more processors 178 and one or more memory 180.

References in the specification to "one embodiment," "an embodiment," "an illustrative embodiment," "some embodiments," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used in the description and claims, the singular form "a", "an" and "the" include both singular and plural references unless the context clearly dictates otherwise. For example, the term "signal" may include, and is contemplated to include, a plurality of signals. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5 percent, 1 percent or 0.1 percent. All numerical ranges provided herein are inclusive of the stated start and end numbers. The term "substantially" indicates mostly (i.e., greater than 50%) or essentially all of a device, substance, or composition.

The term "horizontal" as used herein is defined as a plane parallel to the conventional plane or surface of an element, regardless of its orientation. The term "vertical" refers to a direction perpendicular to the horizontal as just defined. Terms, such as "on", "above", "below", "bottom", "top", "side" (as in "sidewall"), "higher", "lower", "over", and "under", are defined with respect to the horizontal plane.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Implementations defined by each of these transitional terms are within the scope of this disclosure.

The examples and illustrations included herein show, by way of illustration and not of limitation, specific implementations in which the subject matter may be practiced. Other implementations may be utilized and derived therefrom, such that structural and logical substitutions and changes may be made without departing from the scope of this disclosure. Such implementations of the inventive subject matter may be referred to herein individually or collectively by the term "invention" merely for convenience and without intending to voluntarily limit the scope of this application to any single invention or inventive concept, if more than one is in fact disclosed. Thus, although specific implementations have been illustrated and described herein, any arrangement calculated to achieve the same purpose may be substituted for the specific implementations shown. This disclosure is intended to cover any and all adaptations or variations of various implementations. Combinations of the above implementations, and other implementations not specifically described herein, will be apparent to those of skill in the art upon reviewing the above description.

What is claimed is:

1. A dialysis system with integrated concurrent appointment and patient assessment capabilities, comprising:
- a dialysis machine;
- at least one camera and a video monitor communicatively coupled to the dialysis machine and configured to enable concurrent telemedicine communication between a patient undergoing a dialysis session and at least one healthcare provider remote from the dialysis machine;
- a handheld imaging device coupled to the dialysis machine, the handheld imaging device configured to capture high-resolution images of patient-specific conditions during a telemedicine session;
- a scheduling system communicatively coupled to the dialysis machine and configured to:
  - automatically communicate dialysis machine availability to a healthcare scheduling system associated with the at least one healthcare provider,
  - coordinate concurrent appointment confirmations amongst the patient, the dialysis machine availability, and the at least one healthcare provider, and
  - automatically establish the telemedicine session during a portion of the dialysis session according to a respective confirmed time between the patient and the at least one healthcare provider; and
- a data transmission system configured to transmit, from the dialysis machine to the at least one healthcare provider and during the concurrent telemedicine session, one or more real time: dialysis parameters and the captured images; and
- a spatial frequency domain imaging (SFDI) microvascular assessment system communicatively coupled to the dialysis machine and configured to:
  - perform non-contact, noninvasive microvascular assessment of a foot of the patient during the dialysis session;
  - receive a plurality of hemoglobin biomarkers and a recommendation from the SFDI microvascular assessment system; and
  - trigger, based on the recommendation, scheduling of concurrent specialist appointments when the plurality of hemoglobin biomarkers indicate compromised tissue oxygenation or perfusion.

2. The dialysis system of claim 1, further comprising at least one processor configured to:
- receive, from a vascular access monitoring system, measurements of real-time blood flow parameters and machine pressures for the patient during the dialysis session;
- receive, from the vascular access monitoring system and based on the measurements, an assessment of arteriovenous fistula vascular access during the dialysis session;
- trigger scheduling of a vascular appointment when a predefined vascular access threshold is exceeded.

3. The dialysis system of claim 1, further comprising at least one processor configured to:
- trigger an arteriovenous fistula maturation assessment system in communication with the dialysis system to monitor fistula development parameters during the dialysis session;
- in response to receiving, from the arteriovenous fistula maturation assessment system and based on the monitoring, an indication that the fistula is mature, coordinate with the scheduling system to schedule a vascular appointment with a vascular healthcare provider.

4. The dialysis system of claim 1, further comprising at least one processor configured to:
- trigger a hematocrit detection device to monitor fluid levels of the patient in real-time during the dialysis session;
- analyze fluid removal patterns for at least a portion of the dialysis session; and
- trigger automatic adjustment of dialysis machine parameters to prevent or reduce cramping or nausea for the patient based on the monitored fluid levels and on patterns associated with the monitored fluid levels.

5. The dialysis system of claim 1, wherein the at least one healthcare provider comprises one or more of: a nephrology provider, a cardiology provider, an endocrinology provider, a vascular surgery provider, and a podiatry provider.

6. The dialysis system of claim 1, wherein the patient-specific conditions comprise at least one of: an arteriovenous fistula and a diabetic foot ulcer.

7. The dialysis system of claim 1, wherein the dialysis parameters comprise blood pressure, heart rate, and oxygen saturation.

8. The dialysis system of claim 1, further comprising: a blood sampling interface configured to collect blood samples during the dialysis session.

9. The dialysis system of claim 8, wherein the blood sampling interface is communicatively coupled to a point-of-care diagnostic device configured to:
- perform real-time analysis of blood samples collected during the dialysis session;
- generate analyte results related to the concurrent telemedicine session; and
- transmit diagnostic results to the at least one healthcare provider during the telemedicine session.

10. The dialysis system of claim 1, further comprising: a ranking engine communicatively coupled to the scheduling system, the ranking engine configured to prioritize concurrent telemedicine sessions based on a comparing of a predefined patient preference, clinician availability, and dialysis machine availability.

11. The dialysis system of claim 1, wherein the handheld imaging device is an ultrasound device communicatively coupled to an interface configured to enable clinicians to annotate captured images with patient-specific observations and transmit the annotated images to the scheduling system for integration into a profile associated with the patient.

12. The dialysis system of claim 1, further comprising: a message generator communicatively coupled to the scheduling system, the message generator configured to:
- notify the patient and the at least one healthcare provider of appointment confirmations,
- reschedule one or more appointments for the patient, and
- provide updates on dialysis machine availability.

13. The dialysis system of claim 1, further comprising memory configured to store patient data, including fluid loads, weight, and lifestyle metrics, and to transmit the stored patient data to the scheduling system for analysis by the scheduling system.

14. The dialysis system of claim 1, further comprising:
- a tactile feedback system including a smart glove interface configured to:
  - provide tactile feedback to the at least one healthcare provider during remote tissue examination;
  - enable remote manipulation and assessment of patient tissues; and
  - enhance diagnostic capabilities during the concurrent telemedicine session.

15. A computer-implemented method for providing concurrent healthcare appointments during dialysis treatment, the method comprising:

detecting a patient assignment to a dialysis machine for a scheduled dialysis session;

automatically transmitting dialysis machine scheduling information to one or more healthcare scheduling systems associated with a plurality of healthcare providers remote to a dialysis clinic scheduled to provide the dialysis session;

coordinating concurrent appointment scheduling between the scheduled dialysis session and at least one healthcare provider in the plurality of healthcare providers;

automatically establishing a telemedicine session between a patient and the at least one healthcare provider according to the coordinated appointment scheduling at a time window within the dialysis session;

controlling at least one imaging device coupled to the dialysis machine to enable concurrent telemedicine communication between the patient and the at least one healthcare provider during the dialysis session, the controlling comprising:

causing capture of high resolution images from the at least one imaging device, the high resolution images captured during the telemedicine session and being associated with one or more patient-specific condition;

causing transmission of the high resolution images to the at least one healthcare provider during the telemedicine session; and receiving, based on the high resolution images, one or more of: a fistula maturation assessment, a vascular access diagnosis, and a patient dialysis profile recommendation; and performing, using a spatial frequency domain imaging (SFDI) microvascular assessment system communicatively coupled to the dialysis machine, non-contact, noninvasive microvascular assessment of a foot of the patient during the dialysis session;

receiving, from the SFDI microvascular assessment system, a plurality of hemoglobin biomarkers and a recommendation; and triggering, based on the recommendation, scheduling of concurrent specialist appointments when the plurality of hemoglobin biomarkers indicate compromised tissue oxygenation or perfusion.

16. The computer-implemented method of claim 15, wherein the received one or more of: a fistula maturation assessment, a vascular access diagnosis, and a patient dialysis profile recommendation are generated by a machine learning model and an input provided by the at least one healthcare provider, the machine learning model being configured to:

analyze a plurality of dialysis parameters associated with the patient;

predict, based on the plurality of dialysis parameters, patient complications;

automatically generating a recommendation for adjusting dialysis machine parameters including ultrafiltration profiles to preemptively prevent the predicted complications;

generating a customized treatment profile according to the adjusted dialysis machine parameters; and storing the customized treatment profile in a patient record.

17. The computer-implemented method of claim 16, further comprising: transmitting a summary report of the telemedicine session, including the high resolution images and the plurality of dialysis parameters, to a secondary healthcare provider associated with the patient.

18. The computer-implemented method of claim 16, wherein the patient complications include one or more of: muscle cramps, low blood pressure, and fluid overload.

19. A method of treatment comprising:

scheduling a patient for a session of a dialysis treatment on a dialysis machine equipped with integrated telemedicine capabilities;

coordinating concurrent therapeutic consultations for the patient during the dialysis session with a healthcare provider remote to a dialysis clinic housing the dialysis machine, the coordinating comprising automatically transmitting dialysis machine scheduling information to healthcare scheduling systems associated with the healthcare provider;

providing concurrent telemedicine care by the healthcare provider during the dialysis session by:

automatically establishing a telemedicine session between the patient and the healthcare provider at a predetermined time window within the dialysis session, enabling real-time clinical assessment through controlling at least one imaging device coupled to the dialysis machine to capture high resolution images of patient-specific conditions during the telemedicine session, transmitting the high resolution images to the healthcare provider for immediate clinical evaluation, and receiving therapeutic assessments from the healthcare provider based on the high resolution images, the assessments comprising one or more of: a vascular access diagnosis with treatment recommendations, a fistula maturation assessment with management guidance, and a personalized dialysis profile recommendation;

implementing therapeutic interventions based on the received therapeutic assessments to treat the patient;

performing, using a spatial frequency domain imaging (SFDI) microvascular assessment system communicatively coupled to the dialysis machine, non-contact, noninvasive microvascular assessment of a foot of the patient during the dialysis session;

receiving, from the SFDI microvascular assessment system, a plurality of hemoglobin biomarkers and a recommendation; and triggering, based on the recommendation, scheduling of concurrent specialist appointments when the plurality of hemoglobin biomarkers indicate compromised tissue oxygenation or perfusion.

20. The method of treatment of claim 19, wherein implementing the therapeutic interventions comprises:

automatically adjusting dialysis machine parameters to optimize treatment delivery according to the received therapeutic assessments;

generating a customized treatment profile according to the adjusted dialysis machine parameters; and storing the customized treatment profile in a patient record.

* * * * *